US012582635B2

(12) United States Patent
DeCrescenzo et al.

(10) Patent No.: US 12,582,635 B2
(45) Date of Patent: Mar. 24, 2026

(54) COMPOSITIONS AND METHODS FOR TREATING CANCER WITH ATYPICAL BRAF MUTATIONS

(71) Applicant: BIOMED VALLEY DISCOVERIES, INC., Kansas City, MO (US)

(72) Inventors: Gary DeCrescenzo, Parkville, MO (US); Dean Welsch, Parkville, MO (US); Saurabh Saha, Wellesley Hills, MA (US)

(73) Assignee: Biomed Valley Discoveries, Inc., Kansas City, MO (US)

( * ) Notice: Subject to any disclaimer, the term of this patent is extended or adjusted under 35 U.S.C. 154(b) by 796 days.

(21) Appl. No.: 16/613,480

(22) PCT Filed: May 15, 2018

(86) PCT No.: PCT/US2018/032755
§ 371 (c)(1),
(2) Date: Nov. 14, 2019

(87) PCT Pub. No.: WO2018/213302
PCT Pub. Date: Nov. 22, 2018

(65) Prior Publication Data

US 2021/0085663 A1 Mar. 25, 2021

Related U.S. Application Data

(60) Provisional application No. 62/506,995, filed on May 16, 2017.

(51) Int. Cl.

| | |
|---|---|
| ***A61K 31/122*** | (2006.01) |
| ***A61K 31/131*** | (2006.01) |
| ***A61K 31/166*** | (2006.01) |
| ***A61K 31/167*** | (2006.01) |
| ***A61K 31/175*** | (2006.01) |
| ***A61K 31/18*** | (2006.01) |
| ***A61K 31/196*** | (2006.01) |

(Continued)

(52) U.S. Cl.
CPC ........ *A61K 31/4439* (2013.01); *A61K 31/122* (2013.01); *A61K 31/131* (2013.01); *A61K 31/166* (2013.01); *A61K 31/167* (2013.01); *A61K 31/175* (2013.01); *A61K 31/18* (2013.01); *A61K 31/196* (2013.01); *A61K 31/198* (2013.01); *A61K 31/202* (2013.01); *A61K 31/325* (2013.01); *A61K 31/343* (2013.01); *A61K 31/365* (2013.01); *A61K 31/4045* (2013.01); *A61K 31/4164* (2013.01); *A61K 31/4168* (2013.01); *A61K 31/4184* (2013.01); *A61K 31/437* (2013.01); *A61K 31/44* (2013.01); *A61K 31/444* (2013.01); *A61K 31/4985* (2013.01); *A61K 31/506* (2013.01); *A61K 31/513* (2013.01); *A61K 31/517* (2013.01); *A61K 31/519* (2013.01); *A61K 31/53* (2013.01); *A61K 31/5377* (2013.01); *A61K 31/675* (2013.01); *A61K 31/7028* (2013.01); *A61K 33/243* (2019.01); *A61K 35/74* (2013.01); *A61K 38/193* (2013.01); *A61K 38/195* (2013.01); *A61K 38/2013* (2013.01); *A61K 38/2046* (2013.01); *A61K 38/208* (2013.01); *A61K 38/21* (2013.01); *A61K 38/45* (2013.01); *A61K 38/4886* (2013.01); *A61K 39/3955* (2013.01); *A61K 45/06* (2013.01); *A61K 51/00* (2013.01); *A61P 35/00* (2018.01); *C12N 15/1135* (2013.01); *C12Q 1/6886* (2013.01); *C12Q 2600/106* (2013.01); *C12Q 2600/156* (2013.01)

(58) Field of Classification Search
CPC .. A61K 33/243; A61K 31/122; A61K 31/131; A61K 31/166; A61K 31/167; A61K 31/175; A61K 31/18; A61K 31/196; A61K 31/198; A61K 31/202; A61K 31/4439; A61P 35/00
See application file for complete search history.

(56) References Cited

U.S. PATENT DOCUMENTS

| | | | |
|---|---|---|---|
| 2014/0045843 | A1 | 2/2014 | Schafer et al. |
| 2016/0310476 | A1 | 10/2016 | Saha et al. |
| 2016/0317519 | A1 | 11/2016 | Saha et al. |

FOREIGN PATENT DOCUMENTS

| | | |
|---|---|---|
| CN | 104780976 | 7/2015 |
| CN | 104837491 | 8/2015 |

(Continued)

OTHER PUBLICATIONS

Germann et al. ("Abstract 4693: The selective ERK inhibitor BVD-523 is active in models of MAPK pathway-dependent cancers, including those with intrinsic and acquired drug resistance." Cancer Res (2015) 75 (15_Supplement): 4693.https://doi.org/10.1158/1538-7445.AM2015-4693). (Year: 2015).*

(Continued)

*Primary Examiner* — James H Alstrum-Acevedo
*Assistant Examiner* — Chris E Simmons
(74) *Attorney, Agent, or Firm* — Bryan Cave Leighton Paisner LLP

(57) ABSTRACT

The present invention provides, inter alia, methods, pharmaceutical compositions, and kits for treating or ameliorating the effects of a cancer in a subject, which harbors an atypical BRAF mutation (i.e. a non-V600E/K BRAF mutation), comprising an ERK inhibitor. Also provided are methods for identifying a subject having an atypical BRAF mutant cancer who would benefit from therapy comprising an ERK inhibitor.

30 Claims, 4 Drawing Sheets

Specification includes a Sequence Listing.

(51) Int. Cl.

| | |
|---|---|
| *A61K 31/198* | (2006.01) |
| *A61K 31/202* | (2006.01) |
| *A61K 31/325* | (2006.01) |
| *A61K 31/343* | (2006.01) |
| *A61K 31/365* | (2006.01) |
| *A61K 31/4045* | (2006.01) |
| *A61K 31/4164* | (2006.01) |
| *A61K 31/4168* | (2006.01) |
| *A61K 31/4184* | (2006.01) |
| *A61K 31/437* | (2006.01) |
| *A61K 31/44* | (2006.01) |
| *A61K 31/4439* | (2006.01) |
| *A61K 31/444* | (2006.01) |
| *A61K 31/4985* | (2006.01) |
| *A61K 31/506* | (2006.01) |
| *A61K 31/513* | (2006.01) |
| *A61K 31/517* | (2006.01) |
| *A61K 31/519* | (2006.01) |
| *A61K 31/53* | (2006.01) |
| *A61K 31/5377* | (2006.01) |
| *A61K 31/675* | (2006.01) |
| *A61K 31/7028* | (2006.01) |
| *A61K 33/243* | (2019.01) |
| *A61K 35/74* | (2015.01) |
| *A61K 38/19* | (2006.01) |
| *A61K 38/20* | (2006.01) |
| *A61K 38/21* | (2006.01) |
| *A61K 38/45* | (2006.01) |
| *A61K 38/48* | (2006.01) |
| *A61K 39/395* | (2006.01) |
| *A61K 45/06* | (2006.01) |
| *A61K 51/00* | (2006.01) |
| *A61P 35/00* | (2006.01) |
| *A61P 35/02* | (2006.01) |
| *A61P 35/04* | (2006.01) |
| *C12N 15/113* | (2010.01) |
| *C12Q 1/6886* | (2018.01) |

(56) References Cited

FOREIGN PATENT DOCUMENTS

| | | | | |
|---|---|---|---|---|
| CN | 106211755 | 12/2016 | | |
| JP | 2016515586 | 5/2016 | | |
| JP | 2017500320 | 1/2017 | | |
| JP | 2017502017 | 1/2017 | | |
| WO | 2015095838 | 6/2015 | | |
| WO | WO-2015095842 A2 * | 6/2015 | | A61K 31/4439 |
| WO | 2016008853 | 1/2016 | | |
| WO | 2017007941 A2 | 1/2017 | | |

OTHER PUBLICATIONS

Noeparast et al. ("Non-V600 BRAF mutations recurrently found in lung cancer predict sensitivity to the combination of Trametinib and Dabrafenib." Oncotarget, vol. 8, (No. 36), pp. 60094-60108. Published Aug. 26, 2016). (Year: 2016).*

Yao et al., ("BRAF Mutants Evade ERK-Dependent Feedback by Different Mechanisms that Determine Their Sensitivity to Pharmacologic Inhibition." Cancer Cell (2015); 28, 370-383 Sep. 14, 2015 ª2015 Elsevier Inc. http://dx.doi.org/10.1016/j.ccell.2015.08.001.) (Year: 2015).*

Murugan et al. ("Classical V600E and other non-hotspot BRAF mutations in adult differentiated thyroid cancer." J Transl Med. Jul. 7, 2016;14(1):204. doi: 10.1186/s12967-016-0958-x. PMID: 27387551; PMCID: PMC4936197.) (Year: 2016).*

Siroy, et al. "Beyond Braf V600: Clinical Mutation Panel Testing by Next-Generation Sequencing in Advanced Melanoma," Journal of Investigative Dermatology, Sep. 25, 2014, vol. 135.

Basile, et al. "Inhibition of Mutant BRAF Splice Variant Signaling by Next Generation, Selective RAF Inhibitors," Pigment Cell Melanoma Res, May 2014; 27(3): 479-484.

Saha, et la. "A Novel PI3K Gamma Isoform Selective Small Molecule Kinase Inhibitor Demonstrates Single Agent Anti-Tumor Activity and Enhanced Combination Activity with Checkpoint Blockade in Syngeneic Mouse Models of Cancer," AACR-NCI-EORTC International Conference on Molecular Targets and Cancer Therapeutics, Boston MA, Nov. 5, 2015 Retrieved from the Internet: https://biomed-valley.com/wp-content/uploads/pdf/BioMedValleyDiscoveries2015-AACR-NCI-EORTC-Poster.pdf on Feb. 21, 2020.

International Search Report for PCT/US2018/032755 Dated Mar. 8, 2018.

Absalan F., Ronaghi M. (2007) Molecular Inversion Probe Assay. In: Bergman N.H. (eds) Comparative Genomics. Methods In Molecular Biology™, vol. 396. Humana Press.

Arcila, et al. "MAP2K1 (MEK1) mutations define a distinct subset of lung adenocarcinoma associated with smoking," Clin Cancer Res 2015;21:1935-43.

Aronov, et al. "Flipped out: structure-guided design of selective pyrazolylpyrrole ERK inhibitors," J Med Chem 2007;50:1280-7.

Aronov, et al. "Structure-guided design of potent and selective pyrimidylpyrrole inhibitors of extracellular signal-regulated kinase (ERK) using conformational control," J Med Chem 2009;52:6362-8.

Arrington, et al. "Prognostic and predictive roles of KRAS mutation in colorectal cancer," Int J Mol Sci 2012;13:12153-68.

Cargnello, et al. "Activation and function of the MAPKs and their substrates, the MAPK-activated protein kinases," Microbiol Mol Biol Rev 2011;75:50-83.

Carlino, et al. "Preexisting MEK1P124 mutations diminish response to BRAF inhibitors in metastatic melanoma patients," Clin Cancer Res 2015;21:98-105.

Chapman, et al. "Improved survival with vemurafenib in melanoma with BRAF V600E mutation," N Engl J Med 2011;364:2507-16.

Corcoran, et al. "BRAF gene amplification can promote acquired resistance to MEK inhibitors in cancer cells harboring the BRAF V600E mutation," Sci Signal (2010);3(149): ra84.

Dai, et al. "STAT3 mediates resistance to MEK inhibitor through microRNA miR-17," Cancer Res (2011);71:3658-3668.

Davies, et al. "Mutations of the BRAF gene in human cancer," Nature 2002;417:949-54.

Deschenes-Simard, et al. "ERKs in cancer: friends or foes?," Cancer Res 2014;74:412-9.

Dobrzycka, et al. "Mutations in the KRAS gene in ovarian tumors," Folia Histochem Cytobiol 2009;47:221-4.

Emery, et al. "MEK1 mutations confer resistance to MEK and B-RAF inhibition," PNAS (2009); 106(48):20411-6.

Fernandez-Medarde, et al. "Ras in cancer and developmental diseases," Genes Cancer 2011;2:344-58.

Flaherty, et al. "Combined BRAF and MEK inhibition in melanoma with BRAF V600 mutations," N Engl J Med 2012;367:1694-703.

Goetz, et al. "ERK mutations confer resistance to mitogen-activated protein kinase pathway inhibitors," Cancer Res 2014;74:7079-89.

Gollob, et al. "Role of Raf kinase in cancer: therapeutic potential of targeting the Raf/MEK/ERK signal transduction pathway," Semin Oncol 2006;33 :392-406.

Greger, et al. "Combinations of BRAF, MEK, and PI3K/mTOR inhibitors overcome acquired resistance to the BRAF inhibitor GSK2118436 dabrafenib, mediated by NRAS or MEK mutations." Molecular cancer therapeutics 11.4 (2012):909-920.

Groenendijk, et al. "Drug resistance to targeted therapies: deja vu all over again," Mol Oncol 2014;8:1067-83.

Hall, et al. "BRAF mutations: signaling, epidemiology, and clinical experience in multiple malignancies," Cancer Control 2014;21:221-30.

Hardenbol, et al. "Multiplexed genotyping with sequence-tagged molecular inversion probes," Nat. Biotechnol. 2003, No. 21 , p. 673-678.

(56) References Cited

OTHER PUBLICATIONS

Hatzivassiliou, et al. "RAF inhibitors prime wild-type RAF to activate the MAPK pathway and enhance growth." Nature 464.7287 (2010): 431-435.
Hatzivassiliou, et al. "ERK inhibition overcomes acquired resistance to MEK inhibitors," Mol Cancer Ther 2012;11:1143-54.
Hauschild, et al. "Dabrafenib in BRAF-mutated metastatic melanoma: a multicentre, open-label, phase 3 randomised controlled trial," Lancet 2012; 380:358-65.
Hayes, et al. "Long-Term ERK Inhibition in KRAS-Mutant Pancreatic Cancer Is Associated with MYC Degradation and Senescence-like Growth Suppression," Cancer Cell 2016;29:75-89.
Hezel, et al. "Phase II study of gemcitabine, oxaliplatin in combination with panitumumab in KRAS wild-type unresectable or metastatic biliary tract and gallbladder cancer," Br J Cancer 2014;111:430-6.
Jha, et al. "Dissecting therapeutic resistance to ERK inhibition," Mol Cancer Ther 2016;15:548-59.
Johannessen, et al. "COT/MAP3K8 drives resistance to RAF inhibition through MAP kinase pathway reactivation," Nature (2010);468(7326):968-972.
Johnson, et al. "Acquired BRAF inhibitor resistance: A multicenter meta-analysis of the spectrum and frequencies, clinical behaviour, and phenotypic associations of resistance mechanisms," Eur J Cancer 2015;51:2792-9.
Kanda, et al. "Presence of somatic Mutations in most early-stage pancreatic intraepithelial neoplasia," Gastroenterology 2012;142:730-733.
Khattak, et al. "Targeted therapy and immunotherapy in advanced melanoma: an evolving paradigm," Ther Adv Med Oncol 2013;5:105-18.
King, et al. "Dabrafenib; preclinical characterization, increased efficacy when combined with trametinib, while BRAF/MEK tool combination reduced skin lesions." PloS one 8.7 (2013): e67583.
Larkin, et al. "Combined vemurafenib and cobimetinib in BRAF-mutated melanoma," N Engl J Med 2014;371:1867-76.
Little, et al., "Amplification of the Driving Oncogene, KRAS or BRAF, Underpins Acquired Resistance to MEK1/2 Inhibitors in Colorectal Cancer Cells," Sci. Signal. 4, ral7 (2011).
Liu, et al. "BRAF V600E maintains proliferation, transformation, and tumorigenicity of BRAF-mutant papillary thyroid cancer cells." Journal of Clinical Endocrinology & Metabolism 92.6 (2007): 2264-2271.
Liu, et al. "Computational design, chemical synthesis, and biological evaluation of a novel ERK inhibitor (BL-EI001) with apoptosis-inducing mechanisms in breast cancer," Oncotarget 2015;6:6762-75.
Long, et al. "Increased MAPK reactivation in early resistance to dabrafenib/trametinib combination therapy of BRAF-mutant metastatic melanoma," Nat Commun 2014;5:5694.
Long, et al. "Dabrafenib and trametinib versus dabrafenib and placebo for Va1600 BRAF-mutant melanoma: a multicentre, double-blind, phase 3 randomised controlled trial," Lancet 2015;386:444-51.
Manandhar, et al. "Small-molecule inhibitors of the Rcelp CaaX protease," J Biomol Screen. 2007;12(7):983-993.
Massey, et al. "Multiplying therapies and reducing toxicity in metastatic melanoma," Cancer Biol Ther 2015;16:1014-8.
Maurer, et al. "Small-molecule ligands bind to a distinct pocket in Ras and inhibit SOS-mediated nucleotide exchange activity," PNAS. 2012;109(14):5299-304.
McArthur, et al. "Safety and efficacy of vemurafenib in BRAFv600E and BRAFv600K mutation-positive melanoma (BRIM-3): extended follow-up of a phase 3, randomised, open-label study," Lancet Oncol 2014;15:323-32.
Mittal, et al. "The acetyltransferase activity of the bacterial toxin YopJ of Yersinia is activated by eukaryotic host cell inositol hexakisphosphate" Journal of Biological Chemistry 285.26 (2010): 19927-19934.
Morris, et al. "Discovery of a novel ERK inhibitor with activity in models of acquired resistance to BRAF and MEK inhibitors," Cancer Discov 2013;3:742-50.
Nazarian, et al. Melanomas acquire resistance to B-RAF (V600E) inhibition by RTK or N-RAS2010; 468(7326):973-977.
Wong, et al. "Antitumor activity of the ERK inhibitor SCH722984 against BRAF mutant, NRAS mutant and wild-type melanoma," Mol Cancer 13, 194 (2014). https://doi.org/10.1186/1476-4598-13-194.
Notice of Reasons for Refusal for JP Patent Application No. 2019-563125 dated May 24, 2022 (Original and Translated).
Tissot, et al."Clinical characteristics and outcome of patients with lung cancer harboring BRAF mutations," Lung Cancer Jan. 2016;91:23-8. doi: 10.1016/j.lungcan.2015.11.006. Epub Nov. 15, 2015.
CN Application No. 201880040655.8 Office Action dated Jun. 3, 2021.
Baik, et al. "Targeting BRAF-Mutant Non-Small Cell Lung Cancer: From Molecular Profiling to Rationally Designed Therapy", The Oncologist, vol. 22, No. 7, May 9, 2017.
Germann, et al. "Abstract 4693: The selective ERK inhibitor BUD-523 is active in models of MAPK pathway-dependent cancers, including those with intrinsic and acquired drug resistance", Proceedings of the 106th Annual Meeting of the American Association for Cancer Research, AACR; Cancer Res, vol. 75, No. 15 Suppl., Aug. 22, 2015 (Aug. 22, 2015).
Yao, et al. "BRAF Mutants Evade ERK-Dependent Feedback by Different Mechanisms that Determine Their Sensitivity to Pharmacologic Inhibition", Cancer Cell, Cell Press, US, vol. 28, No. 3, Sep. 3, 2015.
Extended European Search Report for 18801345.2 dated Mar. 1, 2021.
Nikolaev, et al. "Exome sequencing identifies recurrent somatic MAP2K1 and MAP2K2 mutations in melanoma," Nat Genet 2012;44:133-9.
Nilsson, et al. "Padlock probes: circularizing oligonucleotides for localized DNA detection," Science. 1994, No. 265, p. 2085-2088.
O'Hara, et al. "The genomics and genetics of endometrial cancer," Adv Genomics Genet 2012;2012:33-47.
Ojesina, et al. "Landscape of genomic alterations in cervical carcinomas," Nature 2014;506:371-5.
Ota et al., "Single nucleotide polymorphism detection by polymerase chain reaction-restriction fragment length polymorphism," Nat Protoc. 2007;2(11).2857-64.
Paraiso, et al. "Recovery of phospho-ERK activity allows melanoma cells to escape from BRAF inhibitor therapy," Br J Cancer 2010;102:1724-30.
Patgirl, et al. "An orthosteric inhibitor of the Ras-Sos interaction," Nat Chem Biol. 2011;7:585-587.
Pennycuick, et al. "Routine EGFR and KRAS mutation analysis using COLD-PCR in non-small cell lung cancer," Int J Clin Pract 2012;66:748-52.
Poulikakos, et al. "RAF inhibitor resistance is mediated by dimerization of aberrantly spliced BRAF(V600E)," Nature 2011;480:387-90.
Queirolo, et al. "Combined BRAF and MEK inhibition for the treatment of BRAF-mutated metastatic melanoma," Cancer Treat Rev 2015;41:519-26.
Rasola, et al. "Activation of mitochondrial ERK protects cancer cells from death through inhibition of the permeability transition," Proc Natl Acad Sci USA 2010;107:726-31.
Rizos, et al. "BRAF inhibitor resistance mechanisms in metastatic melanoma: spectrum and clinical impact," Clin Cancer Res 2014;20:1965-77.
Robert, et al. "Improved overall survival in melanoma with combined dabrafenib and trametinib," N Engl J Med 2015;372:30-9.
Romeo, et al. "Regulation and function of the RSK family of protein kinases," Biochem J 2012;441:553-69.
Rudolph, et al. "Slow inhibition and conformation selective properties of extracellular signal-regulated kinase 1 and 2 inhibitors," Biochemistry 2015;54:22-31.
Schubbert, et al. "Hyperactive Ras in developmental disorders and cancer," Nat Rev Cancer 2007;7:295-308.

(56) References Cited

OTHER PUBLICATIONS

Shaul, et al. "The MEK/ERK cascade: from signaling specificity to diverse functions," Biochim Biophys Acta 2007;1773:1213-26.
Shi, et al. "Acquired resistance and clonal evolution in melanoma during BRAF inhibitor therapy," Cancer Discov 2014;4:80-93.
Shima, et al. "In silico discovery of small-molecule Ras inhibitors that display antitumor activity by blocking the Ras-effector interaction," PNAS. 2013 ; 110(20): 8182-7.
Sun, et al. "Intrinsic resistance to MEK inhibition in KRAS mutant lung and colon cancer through transcriptional induction of ERBB3," Cell Rep 2014;7:86-93.
Trunzer, et al. "Pharmacodynamic effects and mechanisms of resistance to vemurafenib in patients with metastatic melanoma," J Clin Oncol 2013;31:1767-74.
Villanueva, et al. "Acquired resistance to BRAF inhibitors mediated by a RAF kinase switch in melanoma can be overcome by cotargeting MEK and IGF-1R/PI3K," Cancer Cell. 2010;18:683-695.
Wagle, et al. "Dissecting therapeutic resistance to RAF inhibition in melanoma by tumor genomic profiling," Journal of Clinical Oncology 2011;29(22):3085-3096.
Wagle, et al. "MAP kinase pathway alterations in BRAF-mutant melanoma patients with acquired resistance to combined RAF/MEK inhibition," Cancer Discov 2014;4:61-8.
Wainstein, et al. "The dynamic subcellular localization of ERK: mechanisms of translocation and role in various organelles," Curr Opin Cell Biol 2016;39:15-20.
Wang, et al. "Identification of the MEK1(F129L) activating mutation as a potential mechanism of acquired resistance to MEK inhibition in human cancers carrying the B-RAF V600E mutation," Cancer Res (2011);71(16):5535-45.
Yang, et al. "Genomics of Drug Sensitivity in Cancer (GDSC): a resource for therapeutic biomarker discovery in cancer cells," Nucleic Acids Res 2013;41:D955-D961.
Yao, et al. "BRAF Mutants Evade ERK-Dependent Feedback by Different Mechanisms that Determine Their Sensitivity to Pharmacologic Inhibition," Cancer Cell 2015;28:370-83.
Yohe, "Molecular genetic markers in acute myeloid leukemia," J Clin Med 2015;4:460-78.
Porter, et al. "Inhibition of the CaaX proteases Rcelp and Ste24p by peptidyl (acyloxy)methyl ketones," Biochim Biophys Acta. 2007;1773 (6): 853-862.

* cited by examiner

COMPOSITIONS AND METHODS FOR TREATING CANCER WITH ATYPICAL BRAF MUTATIONS

CROSS REFERENCE TO RELATED APPLICATIONS

The present application is the National Stage of International Application No. PCT/US2018/032755, filed on May 15, 2018, which claims benefit to U.S. Provisional Application No. 62/506,995, filed on May 16, 2017. The entire contents of the above applications are incorporated by reference as if recited in full herein.

FIELD OF THE DISCLOSURE

The present disclosure relates to methods, kits, and pharmaceutical compositions for treating or ameliorating the effects of a cancer with atypical genetic mutations using one or more anti-cancer agents.

INCORPORATION BY REFERENCE OF SEQUENCE LISTING

This application contains references to amino acids and/or nucleic acid sequences that have been filed concurrently herewith as sequence listing text file "1065272.000583-seq.txt", file size of 254,245 bytes, created on Sep. 11, 2025. The aforementioned sequence listing is hereby incorporated by reference in its entirety pursuant to 37 C.F.R. § 1.52(e) (5).

BACKGROUND OF THE INVENTION

Mitogen-activated protein kinase (MAPK) or RAS/RAF/MEK/ERK signaling is responsible for several cell signaling pathways involved in control of proliferation, differentiation, and apoptosis. The MAPK cell signaling pathway is found to be disrupted in human cancers, often due to activating mutations of the KRAS, NRAS, or BRAF genes. Selective BRAF inhibitors, such as vemurafenib and dabrafenib, have been developed to target BRAF mutant tumors. For example, vemurafenib is approved for unresectable or metastatic melanomas with BRAF V600E mutation, and detection of the BRAF V600E mutation has become the standard of care for predicting response to vemurafenib, dabrafenib, and trametinib treatment.

While the V600E mutation is the most common BRAF mutation observed in many tumor types, over 100 other mutations within exons 11 and 15 of the BRAF gene have been reported by the Catalog of Somatic Mutations in Cancer (COSMIC) database. The clinical importance of BRAF mutations outside of the V600 codon is largely unknown.

In view of the foregoing, there is a need for novel therapeutic agents that would target the MAPK pathway in cell types harboring BRAF mutations other than V600E. The present application is directed to meeting these and other needs.

SUMMARY OF THE INVENTION

According to one aspect, the present disclosure provides a method for treating or ameliorating the effects of a cancer in a subject harboring a non-V600E/K BRAF mutation, the method comprising administering to the subject an effective amount of an ERK inhibitor or a pharmaceutically acceptable salt thereof.

According to some embodiments, the ERK inhibitor is selected from the group consisting of BVD-523, SCH-722984 (Merck & Co.), SCH-772984 (Merck & Co.), SCH-900353 (MK-8353) (Merck & Co.), LY3214996 (Lilly), AEZS-140 (Aeterna Zentaris), AEZS-131 (Aeterna Zentaris), AEZS-136 (Aeterna Zentaris), LTT-462 (Novartis), RG-7842 (Genentech), CC-90003 (Celgene), KIN-4050 (Kinentia), and combinations thereof.

According to some embodiments, the ERK inhibitor is BVD-523.

According to some embodiments, the non-V600E/K BRAF mutation is a kinase-activated mutation, a kinase-impaired mutation, or a kinase-unknown mutation, and According to some embodiments, the kinase-activated mutation is selected from the group consisting of R462I, I463S, G464E, G464R, G464V, G466A, G469A, N581S, E586K, F595L, L597Q, L597R, L597S, L597V, A598V, T599E, V600R, K601E, S602D, A728V, and combinations thereof.

According to some embodiments, the kinase-impaired mutation is selected from the group consisting of G466E, G466R, G466V, Y472C, K483M, D594A, D594E, D594G, D594H, D594N, D594V, G596R, T599A, S602A, and combinations thereof.

According to some embodiments, the kinase-unknown mutation is selected from the group consisting of T440I, S467L, G469E, G469R, G469S, G469V, L584F, L588F, V600_K601 delinsE, S605I, Q609L, E611Q, and combinations thereof.

According to some embodiments, the non-V600E/K BRAF mutation is selected from the group consisting of D594, G469, K601E, L597, T599 duplication, L485W, F247L, G466V, BRAF fusion, BRAF-AGAP3 rearrangement, BRAF exon 15 slice variant, and combinations thereof.

According to some embodiments, the subject is a mammal.

According to some embodiments, the mammal is selected from the group consisting of humans, primates, farm animals, and domestic animals.

According to some embodiments, the mammal is a human.

According to some embodiments, the cancer is a solid tumor cancer or a hematologic cancer.

According to some embodiments, the cancer is selected from the group consisting of glioblastoma, melanoma, cholangio carcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer.

According to some embodiments, the cancer is selected from the group consisting of small intestine cancer, non-small cell lung cancer, gallbladder cancer, and squamous cell cancer.

According to some embodiments, the method further comprises administering to the subject at least one additional therapeutic agent selected from the group consisting of an MEK inhibitor, a RAF inhibitor, an HDAC inhibitor, and combinations thereof.

According to some embodiments, the MEK inhibitor is selected from the group consisting of anthrax toxin, antroquinonol (Golden Biotechnology), ARRY-142886 (6-(4-bromo-2-chloro-phenylamino)-7-fluoro-3-methyl-3H-benzoimidazole-5-c-arboxylic acid (2-hydroxy-ethoxy)-amide) (Array BioPharma), ARRY-438162 (Array BioPharma) binimetinib (MEK162, ARRY-1662), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxphenyl)-oxanaphthalen-4-one) (Pfizer), PD 184352 (CI-1040) (Pfizer), PD-0325901 (Pfizer), PD318088 (Pfizer), PD334581 (Pfizer), 6-methoxy-7-(3-morpholin-4-yl-propoxy)-4-(4-phenoxy-phenylamino)-quinoline-3-carbonitrile, 4-[3-chloro-4-(1-methyl-1H-imidazol-2-ylsulfanyl)-phenylamino]-6-methoxy-7-(3-morpholin-4-yl-propoxy)-quinoline-3-carbonitrile, pimasertib (Santhera Pharmaceuticals), RDEA119 (Ardea Biosciences/Bayer), refametinib (AstraZeneca), RG422 (Chugai Pharmaceutical Co.), R0092210 (Roche), R04987655 (Hoffmann-La Roche), R05126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio) butadiene) (Sigma), WX-554 (Wilex), YopJ polypeptide (Mittal et al., 2010), pharmaceutically acceptable salts thereof, and combinations thereof.

According to some embodiments, the RAF inhibitor is selected from the group consisting of AAL881 (Novartis), AB-024 (Ambit Biosciences), ARQ-736 (ArQule), ARQ-761 (ArQule), AZ628 (Axon Medchem BV), BAY 43-9006 sorafenib, BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca (SEQ ID NO: 45)) and 523 (cctatcgttagagtcttcctg (SEQ ID NO: 46)) (Liu et al., 2007), CHIR-265 (Novartis), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LXH254 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), PLX3603 (Daiichi Sankyo), PLX8394 (Daiichi Sankyo), RAF-265 (Novartis), RAF-365 (Novartis), REDX0535 (RedX Pharma Plc), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

According to some embodiments, the HDAC inhibitor is selected from the group consisting of Abexinostat (PCI-24781), Givinostat, Entinostat, Vorinostat, CI-994, CUDC-101, Entinostat, BML-210, M344, NVP-LAQ824, Panobinostat, Pracinosat (SB939), Mocetinostat, Resminostat, Romidepsin, Belinostat, pharmaceutically acceptable salts thereof, and combinations thereof.

According to some embodiments, the method further comprises administering to the subject at least one additional therapeutic agent selected from the group consisting of an antibody, antibody fragment, antibody conjugate, a cytotoxic agent, a toxin, a radionuclide, an immunomodulator, a photoactive therapeutic agent, a radiosensitizing agent, a hormone, an anti-angiogenesis agent, and combinations thereof.

According to some embodiments, the antibody, fragment thereof, or conjugate thereof is selected from the group consisting of rituximab (Rituxan), Brentuximab Vedotin (Adcetriz), Ado-trastuzumab emtansine (Kadcyla) Cetuximab (Erbitux), bevacizumab (Avastin), Ibritumomab (Zevalin), vedolizumab (Entyvio), Ipilimumab (Yervoy), Nivolumab (Opdivo), pembrolizumab (Keytruda), Alemtuzamab atezolizumab (Tecentriq), avelumab (Bavencio), durvalumab (Imfinzi), B-701, Ofatumumab, Obinutuzumab (Gazyva) Panitumumab, plozalizumab, BI-754091, OREG-103, COM-701, BI-754111, and combinations thereof.

According to some embodiments, the cytotoxic agent is selected from the group consisting of cyclophosphamide, mechlorethamine, uramustine, melphalan, chlorambucil, ifosfamide, carmustine, lomustine, streptozocin, busulfan, temozolomide, cisplatin, carboplatin, oxaliplatin, nedaplatin, satraplatin, triplatin tetranitrate, doxorubicin, daunorubicin, idarubicin, mitoxantrone, methotrexate, pemetrexed, 6-mercaptopurine, dacarbazine, fludarabine, 5-fluorouracil, arabinosylcytosine, capecitabine, gemcitabine, decitabine, vinca alkaloids, paclitaxel (Taxol), docetaxel (Taxotere), ixabepilone (Ixempra), actinomycin, anthracyclines, valrubicin, epirubicin, bleomycin, plicamycin, mitomycin, pharmaceutically acceptable salts thereof, prodrugs, and combinations thereof.

According to some embodiments, the toxin is diphtheria toxin or portions thereof.

According to some embodiments, the radionuclide is selected from the group consisting of I-125, At-211, Lu-177, Cu-67, I-131, Sm-153, Re-186, P-32, Re-188, In-114m, Y-90, and combinations thereof.

According to some embodiments, the immunomodulator is selected from the group consisting of granulocyte colony-stimulating factor (G-CSF), LAG-3, IMP-321, JCAR-014, ASLAN-002 (BMS-777607), interferons, imiquimod and cellular membrane fractions from bacteria, IL-2, IL-7, IL-12, CCL3, CCL26, CXCL7, synthetic cytosine phosphate-guanosine (CpG), immune-checkpoint inhibitors, and combinations thereof.

According to some embodiments, the radiosensitizing agent is selected from the group consisting of misonidazole, metronidazole, tirapazamine, trans sodium crocetinate, and combinations thereof.

According to some embodiments, the hormone is selected from the group consisting of prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, calcidiol, tamoxifen (Nolvadex), anastrozole (Arimidex), letrozole (Femara), fulvestrant (Faslodex), and combinations thereof.

According to some embodiments, the anti-angiogenesis agent is selected from the group consisting of 2-methoxyestradiol, angiostatin, bevacizumab, cartilage-derived angiogenesis inhibitory factor, endostatin, IFN-alpha, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

According to some embodiments, the additional therapeutic agent is an inhibitor of the PI3K/Akt pathway.

According to some embodiments, the inhibitor of the PI3K/Akt pathway is selected from the group consisting of A-674563 (CAS #552325-73-2), AGL 2263, AMG-319 (Amgen, Thousand Oaks, CA), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, CA), BML-257 (CAS #32387-96-5), BVD-723, CAL-120 (Gilead Sciences, Foster City, CA), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, MA), perifosine, PHT-427 (CAS #1191951-57-1), P13 kinase delta inhibitor, Merck KGaA (Merck & Co., Whitehouse Station, NJ), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, CA), PI3-delta inhibitors, Cellzome (Cellzome AG, Heidelberg, Germany), PI3-delta inhibitors, Intellikine (Intellikine Inc., La Jolla, CA), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, NY), SF-1126 (Semafore Pharmaceuticals, Indianapolis, IN), SH-5, SH-6, Tetrahydro Curcumin, TG100-115 (Targegen Inc., San Diego, CA), Triciribine, X-339 (Xcovery, West Palm Beach, FL), XL-499 (Evotech, Hamburg, Germany), pharmaceutically acceptable salts thereof, and combinations thereof.

According to one aspect, the present disclosure provides a method for treating or ameliorating the effects of a cancer in a subject comprising: (a) identifying a subject with a cancer harboring a non-V600E/K BRAF mutation; and (b) administering to the subject an effective amount of an ERK inhibitor or a pharmaceutically acceptable salt thereof.

According to some embodiments, the ERK inhibitor is selected from the group consisting of BVD-523, SCH-722984 (Merck & Co.), SCH-772984 (Merck & Co.), SCH-900353 (MK-8353) (Merck & Co.), LY3214996 (Lilly), AEZS-140 (Aeterna Zentaris), AEZS-131 (Aeterna Zentaris), AEZS-136 (Aeterna Zentaris), LTT-462 (Novartis), RG-7842 (Genentech), CC-90003 (Celgene), KIN-4050 (Kinentia), and combinations thereof.

According to some embodiments, the ERK inhibitor is BVD-523.

According to some embodiments, the non-V600E/K BRAF mutation is a kinase-activated mutation, a kinase-impaired mutation, or a kinase-unknown mutation, and combinations thereof.

According to some embodiments, the kinase-activated mutation is selected from the group consisting of R462I, I463S, G464E, G464R, G464V, G466A, G469A, N581S, E586K, F595L, L597Q, L597R, L597S, L597V, A598V, T599E, V600R, K601E, S602D, A728V, and combinations thereof.

According to some embodiments, the kinase-impaired mutation is selected from the group consisting of G466E, G466R, G466V, Y472C, K483M, D594A, D594E, D594G, D594H, D594N, D594V, G596R, T599A, S602A, and combinations thereof.

According to some embodiments, the kinase-unknown mutation is selected from the group consisting of T440I, S467L, G469E, G469R, G469S, G469V, L584F, L588F, V600_K601delinsE, S605I, Q609L, E611Q, and combinations thereof.

According to some embodiments, the subject is a mammal.

According to some embodiments, the mammal is selected from the group consisting of humans, primates, farm animals, and domestic animals.

According to some embodiments, the mammal is a human.

According to some embodiments, the cancer is a solid tumor cancer or a hematologic cancer.

According to some embodiments, the cancer is selected from the group consisting of glioblastoma, melanoma, cholangio carcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer.

According to some embodiments, the cancer is selected from the group consisting of small intestine cancer, non-small cell lung cancer, gallbladder cancer, and squamous cell cancer.

According to some embodiments, the method further comprises (i) obtaining a biological sample from the subject; and (ii) screening the sample to determine whether the subject has a non-V600E/K BRAF mutation.

According to some embodiments, the method further comprises administering to the subject at least one additional therapeutic agent selected from the group consisting of an MEK inhibitor, a RAF inhibitor, an HDAC inhibitor, and combinations thereof.

According to some embodiments, the MEK inhibitor is selected from the group consisting of anthrax toxin, antroquinonol (Golden Biotechnology), ARRY-142886 (6-(4-bromo-2-chloro-phenylamino)-7-fluoro-3-methyl-3H-benzoimidazole-5-c-arboxylic acid (2-hydroxy-ethoxy)-amide) (Array BioPharma), ARRY-438162 (Array BioPharma) binimetinib (MEK162, ARRY-1662), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxphenyl)-oxanaphthalen-4-one) (Pfizer), PD 184352 (CI-1040) (Pfizer), PD-0325901 (Pfizer), PD318088 (Pfizer), PD334581 (Pfizer), 6-methoxy-7-(3-morpholin-4-yl-propoxy)-4-(4-phenoxy-phenylamino)-quinoline-3-carbonitrile, 4-[3-chloro-4-(1-methyl-1H-imidazol-2-ylsulfanyl)-phenylamino]-6-methoxy-7-(3-morpholin-4-yl-propoxy)-quinoline-3-carbonitrile, pimasertib (Santhera Pharmaceuticals), RDEA119 (Ardea Biosciences/Bayer), refametinib (AstraZeneca), RG422 (Chugai Pharmaceutical Co.), R0092210 (Roche), R04987655 (Hoffmann-La Roche), R05126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio) butadiene) (Sigma), WX-554 (Wilex), YopJ polypeptide (Mittal et al., 2010), pharmaceutically acceptable salts thereof, and combinations thereof.

According to some embodiments, the RAF inhibitor is selected from the group consisting of AAL881 (Novartis), AB-024 (Ambit Biosciences), ARQ-736 (ArQule), ARQ-761 (ArQule), AZ628 (Axon Medchem BV), BAY 43-9006 sorafenib, BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca (SEQ ID NO: 45)) and 523 (cctatcgttagagtcttcctg (SEQ ID NO: 46)) (Liu et al., 2007), CHIR-265 (Novartis), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LXH254 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), PLX3603 (Daiichi Sankyo), PLX8394 (Daiichi Sankyo), RAF-265 (Novartis), RAF-365 (Novartis), REDX0535 (RedX Pharma Plc), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

According to some embodiments, the HDAC inhibitor is selected from the group consisting of Abexinostat (PCI-24781), Givinostat, Entinostat, Vorinostat, CI-994, CUDC-101 Entinostat, BML-210, M344, NVP-LAQ824, Panobinostat, Pracinosat (SB939), Mocetinostat, Resminostat, Romidepsin, Belinostat, pharmaceutically acceptable salts thereof, and combinations thereof.

According to some embodiments, the method further comprises administering at least one additional therapeutic agent selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

According to some embodiments, the antibody, fragment thereof, or conjugate thereof is selected from the group consisting of rituximab (Rituxan), Brentuximab Vedotin (Adcetriz), Ado-trastuzumab emtansine (Kadcyla) Cetuximab (Erbitux), bevacizumab (Avastin), Ibritumomab (Zevalin), vedolizumab (Entyvio), Ipilimumab (Yervoy), Nivolumab (Opdivo), pembrolizumab (Keytruda), Alemtuzamab atezolizumab (Tecentriq), avelumab (Bavencio), durvalumab (Imfinzi), B-701, Ofatumumab, Obinutuzumab (Gazyva) Panitumumab, plozalizumab, BI-754091, OREG-103, COM-701, BI-754111, and combinations thereof.

According to some embodiments, the cytotoxic agent is selected from the group consisting of cyclophosphamide, mechlorethamine, uramustine, melphalan, chlorambucil, ifosfamide, carmustine, lomustine, streptozocin, busulfan, temozolomide, cisplatin, carboplatin, oxaliplatin, nedaplatin, satraplatin, triplatin tetranitrate, doxorubicin, daunorubicin, idarubicin, mitoxantrone, methotrexate, pemetrexed, 6-mercaptopurine, dacarbazine, fludarabine, 5-fluorouracil, arabinosylcytosine, capecitabine, gemcitabine, decitabine, vinca alkaloids, paclitaxel (Taxol), docetaxel (Taxotere), ixabepilone (Ixempra), actinomycin, anthracyclines, valrubicin, epirubicin, bleomycin, plicamycin, mitomycin, pharmaceutically acceptable salts thereof, prodrugs, and combinations thereof.

According to some embodiments, the toxin is diphtheria toxin or portions thereof.

According to some embodiments, the radionuclide is selected from the group consisting of I-125, At-211, Lu-177, Cu-67, I-131, Sm-153, Re-186, P-32, Re-188, In-114m, Y-90, and combinations thereof.

According to some embodiments, the immunomodulator is selected from the group consisting of granulocyte colony-stimulating factor (G-CSF), LAG-3, IMP-321, JCAR-014, ASLAN-002 (BMS-777607), interferons, imiquimod and cellular membrane fractions from bacteria, IL-2, IL-7, IL-12, CCL3, CCL26, CXCL7, synthetic cytosine phosphate-guanosine (CpG), immune-checkpoint inhibitors, and combinations thereof.

According to some embodiments, the radiosensitizing agent is selected from the group consisting of misonidazole, metronidazole, tirapazamine, trans sodium crocetinate, and combinations thereof.

According to some embodiments, the hormone is selected from the group consisting of prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, calcidiol, tamoxifen (Nolvadex), anastrozole (Arimidex), letrozole (Femara), fulvestrant (Faslodex), and combinations thereof.

According to some embodiments, the anti-angiogenesis agent is selected from the group consisting of 2-methoxyestradiol, angiostatin, bevacizumab, cartilage-derived angiogenesis inhibitory factor, endostatin, IFN-alpha, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

According to some embodiments, the additional therapeutic agent is an inhibitor of the PI3K/Akt pathway.

According to some embodiments, the inhibitor of the PI3K/Akt pathway is selected from the group consisting of A-674563 (CAS #552325-73-2), AGL 2263, AMG-319 (Amgen, Thousand Oaks, CA), AS-041164 (5-benzo[1,3] dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, CA), BML-257 (CAS #32387-96-5), BVD-723, CAL-120 (Gilead Sciences, Foster City, CA), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, MA), perifosine, PHT-427 (CAS #1191951-57-1), PI3 kinase delta inhibitor, Merck KGaA (Merck & Co., Whitehouse Station, NJ), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, CA), PI3-delta inhibitors, Cellzome (Cellzome AG, Heidelberg, Germany), PI3-delta inhibitors, Intellikine (Intellikine Inc., La Jolla, CA), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, NY), SF-1126 (Semafore Pharmaceuticals, Indianapolis, IN), SH-5, SH-6, Tetrahydro Curcumin, TG100-115 (Targegen Inc., San Diego, CA), Triciribine, X-339 (Xcovery, West Palm Beach, FL), XL-499 (Evotech, Hamburg, Germany), pharmaceutically acceptable salts thereof, and combinations thereof.

According to one aspect, the present disclosure provides a method for identifying a subject having cancer who would benefit from therapy with an ERK inhibitor or a pharmaceutically acceptable salt thereof, the method comprising: (a) obtaining a biological sample from the subject; and (b) screening the sample to determine whether the subject has a non-V600E/K BRAF mutation, wherein the presence of the non-V600E/K BRAF mutation confirms that the subject would benefit from therapy with an ERK inhibitor or a pharmaceutically acceptable salt thereof.

According to some embodiments, the ERK inhibitor is selected from the group consisting of BVD-523, SCH-722984 (Merck & Co.), SCH-772984 (Merck & Co.), SCH-900353 (MK-8353) (Merck & Co.), LY3214996 (Lilly), AEZS-140 (Aeterna Zentaris), AEZS-131 (Aeterna Zentaris), AEZS-136 (Aeterna Zentaris), LTT-462 (Novartis), RG-7842 (Genentech), CC-90003 (Celgene), KIN-4050 (Kinentia), and combinations thereof.

According to some embodiments, the ERK inhibitor is BVD-523.

According to some embodiments, the non-V600E/K BRAF mutation is a kinase-activated mutation, a kinase-impaired mutation, or a kinase-unknown mutation, and combinations thereof.

According to some embodiments, the kinase-activated mutation is selected from the group consisting of R462I, I463S, G464E, G464R, G464V, G466A, G469A, N581S, E586K, F595L, L597Q, L597R, L597S, L597V, A598V, T599E, V600R, K601E, S602D, A728V, and combinations thereof.

According to some embodiments, the kinase-impaired mutation is selected from the group consisting of G466E, G466R, G466V, Y472C, K483M, D594A, D594E, D594G, D594H, D594N, D594V, G596R, T599A, S602A, and combinations thereof.

According to some embodiments, the kinase-unknown mutation is selected from the group consisting of T440I, S467L, G469E, G469R, G469S, G469V, L584F, L588F, V600_K601delinsE, S605I, Q609L, E611Q, and combinations thereof.

According to some embodiments, the subject is a mammal.

According to some embodiments, the mammal is selected from the group consisting of humans, primates, farm animals, and domestic animals.

According to some embodiments, the mammal is a human.

According to some embodiments, the cancer is a solid tumor cancer or a hematologic cancer.

According to some embodiments, the cancer is selected from the group consisting of glioblastoma, melanoma, cholangio carcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer.

According to some embodiments, the cancer is selected from the group consisting of small intestine cancer, non-small cell lung cancer, gallbladder cancer, and squamous cell cancer.

According to some embodiments, the method further comprises administering an ERK inhibitor or a pharmaceutically acceptable salt thereof to a subject having a non-V600E/K BRAF mutation.

According to some embodiments, the method further comprises administering to the subject at least one additional therapeutic agent selected from the group consisting of an MEK inhibitor, a RAF inhibitor, an HDAC inhibitor, and combinations thereof.

According to some embodiments, the MEK inhibitor is selected from the group consisting of anthrax toxin, antroquinonol (Golden Biotechnology), ARRY-142886 (6-(4-bromo-2-chloro-phenylamino)-7-fluoro-3-methyl-3H-benzoimidazole-5-c-arboxylic acid (2-hydroxy-ethoxy)-amide) (Array BioPharma), ARRY-438162 (Array BioPharma) binimetinib (MEK162, ARRY-1662), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxphenyl)-oxanaphthalen-4-one) (Pfizer), PD 184352 (CI-1040) (Pfizer), PD-0325901 (Pfizer), PD318088 (Pfizer), PD334581 (Pfizer), 6-methoxy-7-(3-morpholin-4-yl-propoxy)-4-(4-phenoxy-phenylamino)-quinoline-3-carbonitrile, 4-[3-chloro-4-(1-methyl-1H-imidazol-2-ylsulfanyl)-phenylamino]-6-methoxy-7-(3-morpholin-4-yl-propoxy)-quinoline-3-carbonitrile, pimasertib (Santhera Pharmaceuticals), RDEA119 (Ardea Biosciences/Bayer), refametinib (AstraZeneca), RG422 (Chugai Pharmaceutical Co.), R0092210 (Roche), R04987655 (Hoffmann-La Roche), R05126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio) butadiene) (Sigma), WX-554 (Wilex), YopJ polypeptide (Mittal et al., 2010), pharmaceutically acceptable salts thereof, and combinations thereof.

According to some embodiments, the RAF inhibitor is selected from the group consisting of AAL881 (Novartis), AB-024 (Ambit Biosciences), ARQ-736 (ArQule), ARQ-761 (ArQule), AZ628 (Axon Medchem BV), BAY 43-9006 sorafenib, BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca (SEQ ID NO: 45)) and 523 (cctatcgttagagtcttcctg (SEQ ID NO: 46)) (Liu et al., 2007), CHIR-265 (Novartis), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LXH254 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), PLX3603 (Daiichi Sankyo), PLX8394 (Daiichi Sankyo), RAF-265 (Novartis), RAF-365 (Novartis), REDX0535 (RedX Pharma Plc), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

According to some embodiments, the HDAC inhibitor is selected from the group consisting of Abexinostat (PCI-24781), Givinostat, Entinostat, Vorinostat, CI-994, CUDC-101 Entinostat, BML-210, M344, NVP-LAQ824, Panobinostat, Pracinosat (SB939), Mocetinostat, Resminostat, Romidepsin, Belinostat, pharmaceutically acceptable salts thereof, and combinations thereof.

According to some embodiments, the method further comprises administering to the subject having a non-V600E/K BRAF mutation at least one additional therapeutic agent selected from the group consisting of an antibody, an antibody fragment, an antibody conjugate, a cytotoxic agent, a toxin, a radionuclide, an immunomodulator, a photoactive therapeutic agent, a radiosensitizing agent, a hormone, an anti-angiogenesis agent, and combinations thereof.

According to some embodiments, the antibody or fragment thereof is selected from the group consisting of rituximab (Rituxan), Brentuximab Vedotin (Adcetriz), Ado-trastuzumab emtansine (Kadcyla) Cetuximab (Erbitux), bevacizumab (Avastin), Ibritumomab (Zevalin), vedolizumab (Entyvio), Ipilimumab (Yervoy), Nivolumab (Opdivo), pembrolizumab (Keytruda), Alemtuzamab atezolizumab (Tecentriq), avelumab (Bavencio), durvalumab (Imfinzi), B-701, Ofatumumab, Obinutuzumab (Gazyva) Panitumumab, plozalizumab, BI-754091, OREG-103, COM-701, BI-754111, and combinations thereof.

According to some embodiments, the cytotoxic agent is selected from the group consisting of cyclophosphamide, mechlorethamine, uramustine, melphalan, chlorambucil, ifosfamide, carmustine, lomustine, streptozocin, busulfan, temozolomide, cisplatin, carboplatin, oxaliplatin, nedaplatin, satraplatin, triplatin tetranitrate, doxorubicin, daunorubicin, idarubicin, mitoxantrone, methotrexate, pemetrexed, 6-mercaptopurine, dacarbazine, fludarabine, 5-fluorouracil, arabinosylcytosine, capecitabine, gemcitabine, decitabine, vinca alkaloids, paclitaxel (Taxol), docetaxel (Taxotere), ixabepilone (Ixempra), actinomycin, anthracyclines, valrubicin, epirubicin, bleomycin, plicamycin, mitomycin, pharmaceutically acceptable salts thereof, prodrugs, and combinations thereof.

According to some embodiments, the toxin is diphtheria toxin or portions thereof.

According to some embodiments, the radionuclide is selected from the group consisting of I-125, At-211, Lu-177, Cu-67, I-131, Sm-153, Re-186, P-32, Re-188, In-114m, Y-90, and combinations thereof.

According to some embodiments, the immunomodulator is selected from the group consisting of granulocyte colony-stimulating factor (G-CSF), LAG-3, IMP-321, JCAR-014, ASLAN-002 (BMS-777607), interferons, imiquimod and cellular membrane fractions from bacteria, IL-2, IL-7, IL-12, CCL3, CCL26, CXCL7, synthetic cytosine phosphate-guanosine (CpG), immune-checkpoint inhibitors, and combinations thereof.

According to some embodiments, the radiosensitizing agent is selected from the group consisting of misonidazole, metronidazole, tirapazamine, trans sodium crocetinate, and According to some embodiments, the hormone is selected from the group consisting of prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, calcidiol, tamoxifen (Nolvadex), anastrozole (Arimidex), letrozole (Femara), fulvestrant (Faslodex), and combinations thereof.

According to some embodiments, the anti-angiogenesis agent is selected from the group consisting of 2-methoxyestradiol, angiostatin, bevacizumab, cartilage-derived angiogenesis inhibitory factor, endostatin, IFN-alpha, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

According to some embodiments, the additional therapeutic agent is an inhibitor of the PI3K/Akt pathway.

According to some embodiments, the inhibitor of the PI3K/Akt pathway is selected from the group consisting of A-674563 (CAS #552325-73-2), AGL 2263, AMG-319 (Amgen, Thousand Oaks, CA), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, CA), BML-257 (CAS #32387-96-5), BVD-723, CAL-120 (Gilead Sciences, Foster City, CA), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, MA), perifosine, PHT-427 (CAS #1191951-57-1), PI3 kinase delta inhibitor, Merck KGaA (Merck & Co., Whitehouse Station, NJ), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, CA), PI3-delta inhibitors, Cellzome (Cellzome AG, Heidelberg, Germany), PI3-delta inhibitors, Intellikine (Intellikine Inc., La Jolla, CA), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, NY), SF-1126 (Semafore Pharmaceuticals, Indianapolis, IN), SH-5, SH-6, Tetrahydro Curcumin, TG100-115 (Targegen Inc., San Diego, CA), Triciribine, X-339 (Xcovery, West Palm Beach, FL), XL-499 (Evotech, Hamburg, Germany), pharmaceutically acceptable salts thereof, and combinations thereof.

According to one aspect, the present disclosure provides a pharmaceutical composition for treating or ameliorating the effects of a cancer in a subject harboring a non-V600E/K BRAF mutation, the composition comprising a pharmaceutically acceptable carrier or diluent and an effective amount of an ERK inhibitor or a pharmaceutically acceptable salt thereof.

According to some embodiments, the ERK inhibitor is selected from the group consisting of BVD-523, SCH-722984 (Merck & Co.), SCH-772984 (Merck & Co.), SCH-900353 (MK-8353) (Merck & Co.), LY3214996 (Lilly), LY3214996 (Lilly), AEZS-140 (Aeterna Zentaris), AEZS-131 (Aeterna Zentaris), AEZS-136 (Aeterna Zentaris), LTT-462 (Novartis), RG-7842 (Genentech), CC-90003 (Celgene), KIN-4050 (Kinentia), and combinations thereof.

According to some embodiments, the ERK inhibitor is BVD-523.

According to some embodiments, the non-V600E/K BRAF mutation is a kinase-activated mutation, a kinase-impaired mutation, or a kinase-unknown mutation, and According to some embodiments, the kinase-activated mutation is selected from the group consisting of R462I, I463S, G464E, G464R, G464V, G466A, G469A, N581S, E586K, F595L, L597Q, L597R, L597S, L597V, A598V, T599E, V600R, K601E, S602D, A728V, and combinations thereof.

According to some embodiments, the kinase-impaired mutation is selected from the group consisting of G466E, G466R, G466V, Y472C, K483M, D594A, D594E, D594G, D594H, D594N, D594V, G596R, T599A, S602A, and combinations thereof.

According to some embodiments, the kinase-unknown mutation is selected from the group consisting of T440I, S467L, G469E, G469R, G469S, G469V, L584F, L588F, V600_K601 delinsE, S605I, Q609L, E611Q, and combinations thereof.

According to some embodiments, the subject is a mammal.

According to some embodiments, the mammal is selected from the group consisting of humans, primates, farm animals, and domestic animals.

According to some embodiments, the mammal is a human.

According to some embodiments, the cancer is a solid tumor cancer or a hematologic cancer.

According to some embodiments, the cancer is selected from the group consisting of glioblastoma, melanoma, cholangio carcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer.

According to some embodiments, the cancer is selected from the group consisting of small intestine cancer, non-small cell lung cancer, gallbladder cancer, and squamous cell cancer.

According to some embodiments, the composition is administered to the subject orally or by injection.

According to some embodiments, the composition is administered to the subject as a tablet.

According to some embodiments, the pharmaceutical composition comprises at least one additional therapeutic agent selected from the group consisting of an MEK inhibitor, a RAF inhibitor, an HDAC inhibitor, and combinations thereof.

According to some embodiments, the MEK inhibitor is selected from the group consisting of anthrax toxin, antroquinonol (Golden Biotechnology), ARRY-142886 (6-(4-bromo-2-chloro-phenylamino)-7-fluoro-3-methyl-3H-benzoimidazole-5-c-arboxylic acid (2-hydroxy-ethoxy)-amide) (Array BioPharma), ARRY-438162 (Array BioPharma) binimetinib (MEK162, ARRY-1662), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxphenyl)-oxanaphthalen-4-one) (Pfizer), PD 184352 (CI-1040) (Pfizer), PD-0325901 (Pfizer), PD318088 (Pfizer), PD334581 (Pfizer), 6-methoxy-7-(3-morpholin-4-yl-propoxy)-4-(4-phenoxy-phenylamino)-quinoline-3-carbonitrile, 4-[3-chloro-4-(1-methyl-1H-imidazol-2-ylsulfanyl)-phenylamino]-6-methoxy-7-(3-morpholin-4-yl-propoxy)-quinoline-3-carbonitrile, pimasertib (Santhera Pharmaceuticals), RDEA119 (Ardea Biosciences/Bayer), refametinib (AstraZeneca), RG422 (Chugai Pharmaceutical Co.), R0092210 (Roche), R04987655 (Hoffmann-La Roche), R05126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio) butadiene) (Sigma), WX-554 (Wilex), YopJ polypeptide (Mittal et al., 2010), pharmaceutically acceptable salts thereof, and combinations thereof.

According to some embodiments, the RAF inhibitor is selected from the group consisting of AAL881 (Novartis), AB-024 (Ambit Biosciences), ARQ-736 (ArQule), ARQ-761 (ArQule), AZ628 (Axon Medchem BV), BAY 43-9006 sorafenib, BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca (SEQ ID NO: 45)) and 523 (cctatcgttagagtcttcctg (SEQ ID NO: 46)) (Liu et al., 2007), CHIR-265 (Novartis), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LXH254 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), PLX3603 (Daiichi Sankyo), PLX8394 (Daiichi Sankyo), RAF-265 (Novartis), RAF-365 (Novartis), REDX0535 (RedX Pharma Plc), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

According to some embodiments, the HDAC inhibitor is selected from the group consisting of Abexinostat (PCI-24781), Givinostat, Entinostat, Vorinostat, CI-994, CUDC-101 Entinostat, BML-210, M344, NVP-LAQ824, Panobinostat, Pracinosat (SB939), Mocetinostat, Resminostat, Romidepsin, Belinostat, pharmaceutically acceptable salts thereof, and combinations thereof.

According to some embodiments, the pharmaceutical composition further comprises at least one additional therapeutic agent selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

According to some embodiments, the antibody, fragment thereof, or conjugate thereof is selected from the group consisting of rituximab (Rituxan), Brentuximab Vedotin (Adcetriz), Ado-trastuzumab emtansine (Kadcyla) Cetuximab (Erbitux), bevacizumab (Avastin), Ibritumomab (Zevalin), vedolizumab (Entyvio), Ipilimumab (Yervoy), Nivolumab (Opdivo), pembrolizumab (Keytruda), Alemtuzamab atezolizumab (Tecentriq), avelumab (Bavencio), durvalumab (Imfinzi), B-701, Ofatumumab, Obinutuzumab (Gazyva) Panitumumab, plozalizumab, BI-754091, OREG-103, COM-701, BI-754111, and combinations thereof.

According to some embodiments, the cytotoxic agent is selected from the group consisting of cyclophosphamide, mechlorethamine, uramustine, melphalan, chlorambucil, ifosfamide, carmustine, lomustine, streptozocin, busulfan, temozolomide, cisplatin, carboplatin, oxaliplatin, nedaplatin, satraplatin, triplatin tetranitrate, doxorubicin, daunorubicin, idarubicin, mitoxantrone, methotrexate, pemetrexed, 6-mercaptopurine, dacarbazine, fludarabine, 5-fluorouracil, arabinosylcytosine, capecitabine, gemcitabine, decitabine, vinca alkaloids, paclitaxel (Taxol), docetaxel (Taxotere), ixabepilone (Ixempra), actinomycin, anthracyclines, valrubicin, epirubicin, bleomycin, plicamycin, mitomycin, pharmaceutically acceptable salts thereof, prodrugs, and combinations thereof.

According to some embodiments, the toxin is diphtheria toxin or portions thereof.

According to some embodiments, the radionuclide is selected from the group consisting of I-125, At-211, Lu-177, Cu-67, I-131, Sm-153, Re-186, P-32, Re-188, In-114m, Y-90, and combinations thereof.

According to some embodiments, the immunomodulator is selected from the group consisting of granulocyte colony-stimulating factor (G-CSF), LAG-3, IMP-321, JCAR-014, ASLAN-002 (BMS-777607), interferons, imiquimod and cellular membrane fractions from bacteria, IL-2, IL-7, IL-12, CCL3, CCL26, CXCL7, synthetic cytosine phosphate-guanosine (CpG), immune-checkpoint inhibitors, and combinations thereof.

According to some embodiments, the radiosensitizing agent is selected from the group consisting of misonidazole, metronidazole, tirapazamine, trans sodium crocetinate, and combinations thereof.

According to some embodiments, the hormone is selected from the group consisting of prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, calcidiol, tamoxifen (Nolvadex), anastrozole (Arimidex), letrozole (Femara), fulvestrant (Faslodex), and combinations thereof.

According to some embodiments, the anti-angiogenesis agent is selected from the group consisting of 2-methoxyestradiol, angiostatin, bevacizumab, cartilage-derived angiogenesis inhibitory factor, endostatin, IFN-alpha, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

According to some embodiments, the additional therapeutic agent is an inhibitor of the PI3K/Akt pathway.

According to some embodiments, the inhibitor of the PI3K/Akt pathway is selected from the group consisting of A-674563 (CAS #552325-73-2), AGL 2263, AMG-319 (Amgen, Thousand Oaks, CA), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, CA), BML-257 (CAS #32387-96-5), BVD-723, CAL-120 (Gilead Sciences, Foster City, CA), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, MA), perifosine, PHT-427 (CAS #1191951-57-1), P13 kinase delta inhibitor, Merck KGAA (Merck & Co., Whitehouse Station, NJ), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, CA), PI3-delta inhibitors, Cellzome (Cellzome AG, Heidelberg, Germany), PI3-delta inhibitors, Intellikine (Intellikine Inc., La Jolla, CA), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, NY), SF-1126 (Semafore Pharmaceuticals, Indianapolis, IN), SH-5, SH-6, Tetrahydro Curcumin, TG100-115 (Targegen Inc., San Diego, CA), Triciribine, X-339 (Xcovery, West Palm Beach, FL), XL-499 (Evotech, Hamburg, Germany), pharmaceutically acceptable salts thereof, and combinations thereof.

According to some embodiments, the pharmaceutical composition is in a unit dosage form comprising both the ERK inhibitor and the additional therapeutic agent.

According to some embodiments, the pharmaceutical composition the ERK inhibitor is in a first unit dosage form and the additional therapeutic agent is in a second unit dosage form, separate from the first.

According to some embodiments, the ERK inhibitor and the additional therapeutic agent are co-administered to the subject.

According to some embodiments, the ERK inhibitor and the additional therapeutic agent are administered to the subject serially.

According to some embodiments, the ERK inhibitor is administered to the subject prior to or subsequent to administration of the additional therapeutic agent.

According to one aspect, the present disclosure provides a method for treating or ameliorating the effects of a cancer in a subject harboring a non-V600E/K BRAF mutation, the method comprising administering to the subject an effective amount of BVD-523 or a pharmaceutically acceptable salt thereof.

According to one aspect, the present disclosure provides a method for treating or ameliorating the effects of a cancer in a subject comprising: (a) identifying a subject with a cancer harboring a non-V600E/K BRAF mutation; and (b) administering to the subject an effective amount of BVD-523 or a pharmaceutically acceptable salt thereof.

According to one aspect, the present disclosure provides a method for identifying a subject having cancer who would benefit from therapy with BVD-523 or a pharmaceutically acceptable salt thereof, the method comprising: (a) obtaining a biological sample from the subject; and (b) screening the sample to determine whether the subject has a non-V600E/K BRAF mutation, wherein the presence of the non-V600E/K BRAF mutation confirms that the subject would benefit from therapy with BVD-523 or a pharmaceutically acceptable salt thereof.

According to one aspect, the present disclosure provides a pharmaceutical composition for treating or ameliorating the effects of a cancer in a subject harboring a non-V600E/K BRAF mutation, the composition comprising a pharmaceutically acceptable carrier or diluent and an effective amount of BVD-523 or a pharmaceutically acceptable salt thereof.

According to one aspect, the present disclosure provides a kit for treating or ameliorating the effects of a cancer in a subject harboring a non-V600E/K BRAF mutation, the kit comprising a pharmaceutical composition disclosed herein, packaged together with instructions for its use.

According to some embodiments, the RAF inhibitor is selected from the group consisting of erlotinib (Tarceva), gefitinib (Iressa), imatinib mesylate (Gleevec), lapatinib (Tyverb), sunitinib malate (Sutent), pharmaceutically acceptable salts thereof, and combinations thereof.

According to some embodiments, the RAF inhibitor is selected from the group consisting of LXH254 (Novartis), PLX3603 (Daiichi Sankyo), PLX8394 (Daiichi Sankyo), REDX0535 (RedX Pharma Plc), pharmaceutically acceptable salts thereof, and combinations thereof.

According to some embodiments, the HDAC inhibitor is selected from the group consisting of Vorinostat, Panobinostat, Romidepsin, Belinostat, pharmaceutically acceptable salts thereof, and combinations thereof.

According to some embodiments, the antibody, fragment thereof, or conjugate thereof is selected from the group consisting of rituximab (Rituxan), Brentuximab Vedotin (Adcetriz), Ado-trastuzumab emtansine (Kadcyla), Ipilimumab (Yervoy), Nivolumab (Opdivo), pembrolizumab (Keytruda), Alemtuzamab atezolizumab (Tecentriq), durvalumab (Imfinzi), Ofatumumab, Obinutuzumab (Gazyva), Panitumumab, and combinations thereof.

According to some embodiments, the inhibitor of the PI3K/Akt pathway is BVD-723.

BRIEF DESCRIPTION OF THE DRAWINGS

As shown in FIG. 3, all 28 patients are included as represented by the horizontal bars, one for each subject. The duration of treatment for each subject in each group is illustrated from the top (longest treatment duration) to bottom (least treatment duration) of the groups. The horizontal axis represents the duration, in days, that the patient was on the study. FIG. 3 also shows the type of response achieved for each patient according to RECIST v1.1 (diamond=partial response; circle=stable disease; vertical bar=progressive disease; triangle=not evaluated).

DETAILED DESCRIPTION OF THE INVENTION

Figure 1:
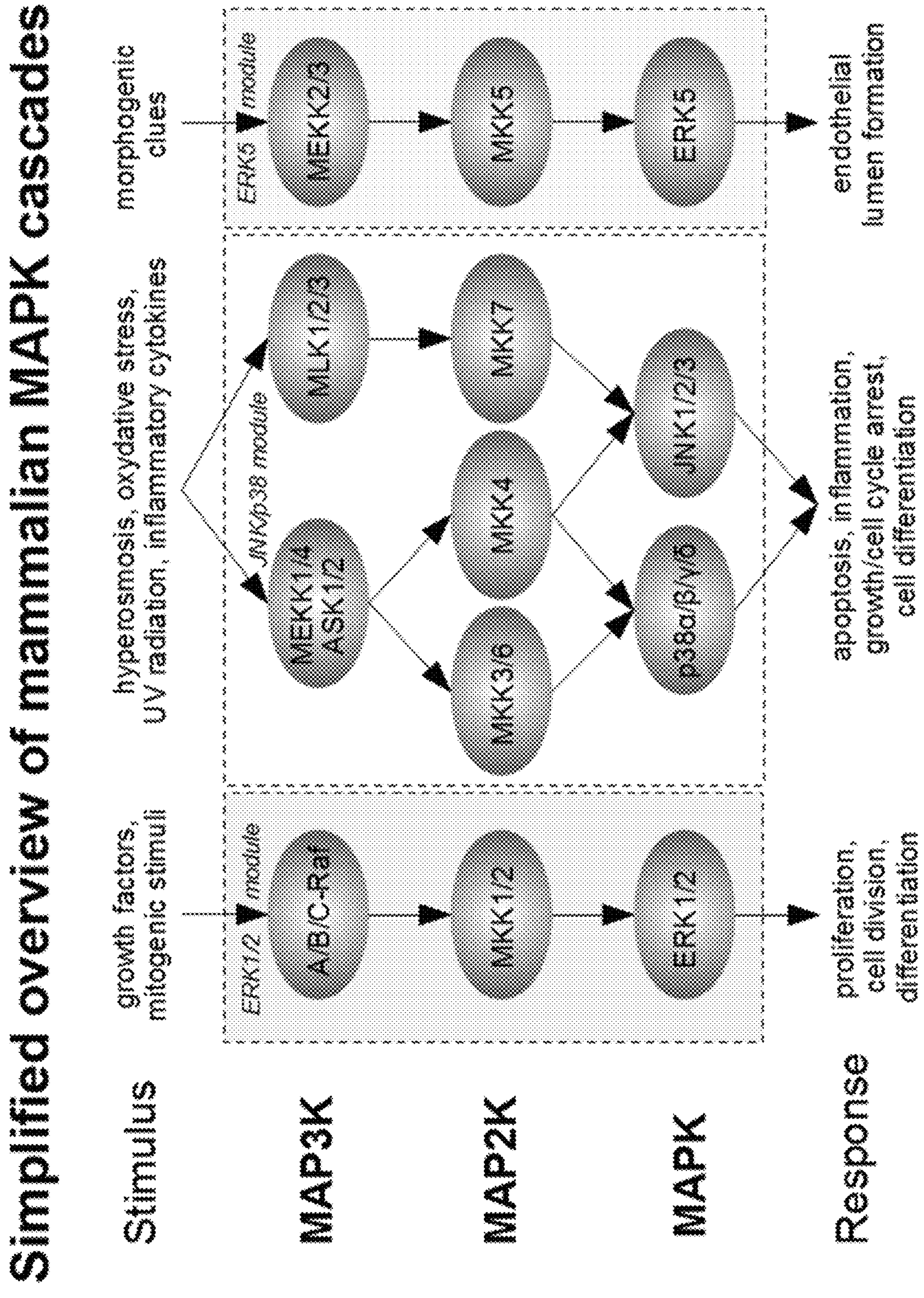
FIG. 1 shows a schematic of the mitogen-activated protein kinases (MAPK) pathway.

According to one aspect, the present disclosure provides a method for treating or ameliorating the effects of a cancer in a subject harboring a non-V600E/K BRAF mutation comprising administering to the subject an effective amount of ERK inhibitor or a pharmaceutically acceptable salt thereof.

As used herein, the terms "V600E/K BRAF mutation", as it related to cancer in a subject, and grammatical variations thereof, means a cancer cell that comprises a nonsynonymous substitution mutation in the gene encoding human BRAF (SEQ ID NO:2) that causes the amino acid valine (V) at amino acid position 600 of BRAF to be substituted by glutamic acid (E) or lysine (K). As used herein, the terms "harboring a non-V600E/K BRAF mutation", as it relates to a cancer in a subject, and grammatical variations thereof, means that a cancer cell comprises a somatic cell mutation that is not a V600E/K BRAF mutation. As used herein, all BRAF mutations are based on the human wild-type sequence (SEQ ID NO: 2). Orthologs thereof from other species are also contemplated herein.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

As used herein, the term an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound or composition according to the invention will be that amount of the composition, which is the lowest dose effective to produce the desired effect. The effective dose of a compound or composition of the present invention may be administered as two, three, four, five, six or more sub-doses, administered separately at appropriate intervals throughout the day.

According to some embodiments, the ERK inhibitor is selected from the group consisting of BVD-523, SCH-722984 (Merck & Co.), SCH-772984 (Merck & Co.), SCH-900353 (MK-8353) (Merck & Co.), LY3214996 (Lilly), AEZS-140 (Aeterna Zentaris), AEZS-131 (Aeterna Zentaris), AEZS-136 (Aeterna Zentaris), LTT-462 (Novartis), RG-7842 (Genentech), CC-90003 (Celgene), KIN-4050 (Kinentia), and combinations thereof. According to some embodiments, the ERK inhibitor is BVD-523.

In the present invention, BVD-523 is a compound according to formula (I):

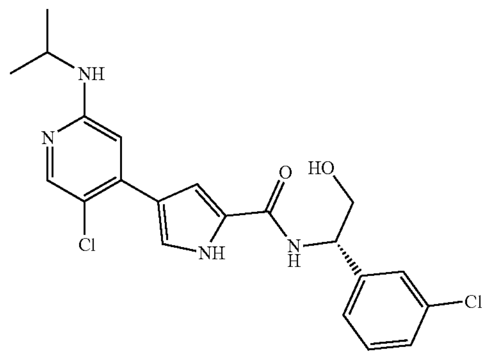 [SMILES: CC(C)Nc1cc(-c2c[nH]c(C(=O)N[C@H](CO)c3cccc(Cl)c3)c2)c(Cl)cn1]

and pharmaceutically acceptable salts thereof. BVD-523 is a highly potent, selective, reversible, ATP-competitive ERK1/2 inhibitor. BVD-523 may be synthesized according to the methods disclosed in, e.g., U.S. Pat. No. 7,354,939, which is incorporated by reference. Enantiomers and racemic mixtures of both enantiomers of BVD-523 are also contemplated within the scope of the present invention. BVD-523 is an ERK1/2 inhibitor with a mechanism of action that is believed to be, e.g., unique and distinct from certain other ERK1/2 inhibitors, such as SCH772984. For example, other ERK1/2 inhibitors, such as SCH772984, inhibit autophosphorylation of ERK (Morris et al., 2013), whereas BVD-523 allows for the autophosphorylation of ERK while still inhibiting ERK.

According to some embodiments, the subject's cancer has a somatic mutation in the BRAF gene. As used herein, "somatic mutation" means a change occurring in any cell that is not destined to become a germ cell. The mutation may be, e.g., a substitution, deletion, insertion, or a fusion. Table 1 below shows a distribution overview of BRAF mutations, as shown in the Sanger database.

TABLE 1

Distribution overview of BRAF mutations

| Mutation Type | Mutant samples | Percentage |
|---|---|---|
| Substitution nonsense | 23 | 0.07 |
| Substitution missense | 32955 | 99.07 |
| Substitution synonymous | 80 | 0.24 |
| Insertion inframe | 25 | 0.08 |
| Insertion frameshift | 1 | 0.00 |
| Deletion inframe | 13 | 0.04 |
| Deletion frameshift | 5 | 0.02 |
| Complex | 39 | 0.12 |
| Other | 172 | 0.52 |
| Total | 33263 | 100 |

BRAF mutations are found in approximately 66% melanoma (Davies et al., 2002; Brose et al., 2002; Hocket et al., 2007), and a relatively lower percentage in other cancers, 36% thyroid tumors and 10% colon cancers (Xu et al., 2003; Fransen et al., 2004). The most prevalent BRAF mutation occurs at amino acid 600 of the human wild-type protein kinase (SEQ ID NO:2) by substituting valine with glutamic acid resulting in the mutant B-RafV600E, which accounts for about 80% of BRAF mutations (Davies et al., 2002; Hocker et al., 2007). B-RafV600E kinase domain has 500-fold higher kinase activity compared to the basal activity of wild-type B-Raf (Wan et al., 2004). Of the other BRAF mutations identified in melanoma, V600K and V600D/R are also common and represent 16% and 3% of all BRAF mutations, respectively (Long et al., 2011). In addition to melanoma, BRAF mutations are also common in many other cancers including papillary thyroid carcinoma, ovarian carcinoma, and colorectal carcinoma. (Wellbrock et al., 2004). In one study, BRAF splice variants (splicing out exons 14 and 15) were found in 5/24 (21%) colorectal cancers cell lines (Seth et al., 2009).

Table 2 below from the Sanger database shows the distribution and frequency of BRAF mutations in human tumors.

TABLE 2

| Primary Tissue | Unique Mutated Samples | Total Unique Samples | % Mutated |
|---|---|---|---|
| NS | 1071 | 1788 | 59.90 |
| Adrenal gland | 3 | 155 | 1.94 |
| Autonomic ganglia | 3 | 703 | 0.43 |
| Biliary tract | 36 | 684 | 5.26 |
| Bone | 5 | 284 | 1.76 |
| Breast | 27 | 2297 | 1.18 |
| Central nervous system | 206 | 3297 | 6.25 |
| Cervix | 6 | 473 | 1.27 |
| Endometrium | 40 | 2510 | 1.59 |
| Eye | 70 | 732 | 9.56 |
| Fallopian tube | 0 | 2 | 0 |
| Gastrointestinal tract (site indeterminate) | 5 | 514 | 0.97 |
| Genital tract | 4 | 54 | 7.41 |
| Haematopoietic and lymphoid tissue | 507 | 5388 | 9.41 |
| Kidney | 34 | 959 | 3.55 |
| Large intestine | 8301 | 67530 | 12.29 |
| Liver | 18 | 618 | 2.91 |
| Lung | 293 | 11249 | 2.60 |
| Meninges | 0 | 74 | 0 |
| Oesophagus | 5 | 927 | 0.54 |
| Ovary | 312 | 3922 | 7.96 |
| Pancreas | 16 | 1089 | 1.47 |
| Parathyroid | 0 | 20 | 0 |
| Penis | 0 | 28 | 0 |
| Peritoneum | 0 | 37 | 0 |
| Pituitary | 1 | 115 | 0.87 |
| Placenta | 0 | 2 | 0 |
| Pleura | 3 | 148 | 2.03 |

TABLE 2-continued

| Primary Tissue | Unique Mutated Samples | Total Unique Samples | % Mutated |
|---|---|---|---|
| Prostate | 25 | 1483 | 1.69 |
| Salivary gland | 1 | 131 | 0.76 |
| Skin | 7245 | 16943 | 42.76 |
| Small intestine | 12 | 251 | 4.78 |
| Soft tissue | 45 | 2160 | 2.08 |
| Stomach | 11 | 1473 | 0.75 |
| Testis | 7 | 251 | 2.79 |
| Thymus | 0 | 50 | 0 |
| Thyroid | 14929 | 38002 | 39.28 |
| Upper aerodigestive tract | 14 | 1352 | 1.04 |
| Urinary tract | 8 | 612 | 1.31 |
| Vagina | 0 | 1 | 0 |
| Vuvla | 0 | 3 | 0 |
| Total | 33263 | 168311 | 19.76 |

Table 3 below shows select nucleic acid and amino acid sequences of BRAF. These sequences may be used in methods for identifying subjects with a mutant BRAF genotype (such as in the methods set forth below).

TABLE 3

| SEQ ID NO | Nucleic acid or polypeptide | Organism | Other information |
|---|---|---|---|
| 1 | nucleic acid | human | |
| 2 | polypeptide | human | |
| 3 | nucleic acid | rat (*Rattus norvegicus*) | |
| 4 | polypeptide | rat (*Rattus norvegicus*) | |
| 5 | nucleic acid | mouse, *Mus musculus* | |
| 6 | polypeptide | mouse, *Mus musculus* | |
| 7 | nucleic acid | rabbit, *Oryctolagus cuniculus* | |
| 8 | polypeptide | rabbit, *Oryctolagus cuniculus* | |
| 9 | nucleic acid | guinea pig, *Cavia porcellus* | |
| 10 | polypeptide | guinea pig, *Cavia porcellus* | |
| 11 | nucleic acid | dog, *Canis lups familiaris* | variant x1 |
| 12 | polypeptide | dog, *Canis lups familiaris* | variant x1 |
| 13 | nucleic acid | dog, *Canis lups familiaris* | variant x2 |
| 14 | polypeptide | dog, *Canis lups familiaris* | variant x2 |
| 15 | nucleic acid | cat, *Felis catus* | |
| 16 | polypeptide | cat, *Felis catus* | |
| 17 | nucleic acid | cow, *Bos taurus* | variant X1 |
| 18 | polypeptide | cow, *Bos taurus* | variant X1 |
| 19 | nucleic acid | cow, *Bos taurus* | variant X2 |
| 20 | polypeptide | cow, *Bos taurus* | variant X2 |
| 21 | nucleic acid | cow, *Bos taurus* | variant X3 |
| 22 | polypeptide | cow, *Bos taurus* | variant X3 |
| 23 | nucleic acid | cow, *Bos taurus* | variant X4 |
| 24 | polypeptide | cow, *Bos taurus* | variant X4 |
| 25 | nucleic acid | cow, *Bos taurus* | variant X5 |
| 26 | polypeptide | cow, *Bos taurus* | variant X5 |
| 27 | nucleic acid | cow, *Bos taurus* | variant X6 |
| 28 | polypeptide | cow, *Bos taurus* | variant X6 |
| 29 | nucleic acid | cow, *Bos taurus* | variant X7 |
| 30 | polypeptide | cow, *Bos taurus* | variant X7 |
| 31 | nucleic acid | cow, *Bos taurus* | variant X8 |
| 32 | polypeptide | cow, *Bos taurus* | variant X8 |
| 33 | nucleic acid | cow, *Bos taurus* | variant X9 |
| 34 | polypeptide | cow, *Bos taurus* | variant X9 |
| 35 | nucleic acid | cow, *Bos taurus* | variant X10 |
| 36 | polypeptide | cow, *Bos taurus* | variant X10 |
| 37 | nucleic acid | cow, *Bos taurus* | variant X11 |
| 38 | polypeptide | cow, *Bos taurus* | variant X11 |
| 39 | nucleic acid | cow, *Bos taurus* | variant 2 |
| 40 | polypeptide | cow, *Bos taurus* | variant 2 |
| 41 | nucleic acid | horse, *Equus caballus* | |
| 42 | polypeptide | horse, *Equus caballus* | |
| 43 | nucleic acid | chicken, *Gallus gallus* | |
| 44 | polypeptide | chicken, *Gallus gallus* | |

Methods for identifying mutations in nucleic acids, such as the above identified BRAF genes, are known in the art. Nucleic acids may be obtained from biological samples. In the present invention, biological samples include, but are not limited to, blood, plasma, urine, skin, saliva, and biopsies. Biological samples are obtained from a subject by routine procedures and methods which are known in the art.

Non-limiting examples of methods for identifying mutations include PCR, sequencing, hybrid capture, in-solution capture, molecular inversion probes, fluorescent in situ hybridization (FISH) assays, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

The PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in, e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) methods are known in the art and are disclosed in e.g., Absalan et al., 2008. Such methods use MIP molecules, which are special "padlock" probes (Nilsson et al., 1994) for genotyping. A MIP molecule is a linear oligonucleotide that contains specific regions, universal sequences, restriction sites and a Tag (index) sequence (16-22 bp). In such methods, a MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of a Tag-cTag duplex, a signal is detected.

According to some embodiments, the non-V600E/K BRAF mutation is a kinase-activated mutation, a kinase-impaired mutation, a kinase-unknown mutation, and combinations thereof. As used herein, the term “kinase-activated mutation”, and grammatical variations thereof, means that a mutation causes elevation of the kinase activity of the mutated kinase relative to the wild-type kinase. As used herein, the term “kinase-impaired mutation”, and grammatical variations thereof, means that a mutation causes a decrease in the kinase activity of the mutated kinase relative to the wild-type kinase. As used herein, the term “kinase-unknown mutation”, and grammatical variations thereof, means that the activity of the mutant kinase is not known or that the activity of the mutated kinase is approximately equivalent to the kinase activity of the wild-type kinase. (See Zheng, G., et al., Clinical detection and categorization of uncommon and concomitant mutations involving BRAF, BMC Cancer, (2015) 15:779, incorporated by reference herein in its entirety)

According to some embodiments, the BRAF kinase-activated mutation is selected from the group consisting of R462I, I463S, G464E, G464R, G464V, G466A, G469A, N581S, E586K, F595L, L597Q, L597R, L597S, L597V, A598V, T599E, V600R, K601E, S602D, A728V, and combinations thereof. According to some embodiments, the BRAF kinase-impaired mutation is selected from the group consisting of G466E, G466R, G466V, Y472C, K483M, D594A, D594E, D594G, D594H, D594N, D594V, G596R, T599A, S602A, and combinations thereof. According to some embodiments, the BRAF kinase-unknown mutation is selected from the group consisting of T440I, S467L, G469E, G469R, G469S, G469V, L584F, L588F, V600_K601delinsE, S605I, Q609L, E611Q, and combinations thereof. As used herein all BRAF mutations are based on the human wild-type sequence (SEQ ID NO: 2). Orthologs thereof from other species are also contemplated herein.

In the present invention, the method and composition for treating non-V600E/K BRAF mutations are effective against disease states that harbor a single mutation and one or more mutations. Indeed, any single mutations or any combination of mutations disclosed herein (or hereinafter identified) may be treated with the compositions or according to the methods of the present invention (e.g., any combination of non-V600E/K mutation or any combination of non-V600E/K mutation with a V600E/K mutation).

According to some embodiments, the non-V600E/K BRAF mutation is selected from the group consisting of D594, G469, K601E, L597, T599 duplication, L485W, F247L, G466V, BRAF fusion, BRAF-AGAP3 rearrangement, BRAF exon 15 slice variant, and As used herein, the notation for the amino acid substitution mutation comprises the closed format of: wild-type amino acid; position; substituted amino acid (e.g., K601E). As used herein, the notation for amino acid substitution also comprises the open ended format of: wild-type amino acid; position (e.g., G469). As used herein, the open ended notation comprises substitutions of any amino acid. For example, the G469 mutation discloses a substitution of glycine at position 469 by any of amino acids A, R, N, D, C, Q, E, H, I, L, K, M, F, P, S, T, W, Y, V. Also as used herein, the closed notation comprises substitutions by any amino acid, and preferably the stated substituted amino acid. For example, the K601E mutation discloses a substitution of lysine at position 601 by any of amino acids A, R, N, D, C, Q, E, G, H, I, L, M, F, P, S, T, W, Y, V, and more preferably by amino acid E. The use of a closed notation, as used herein, should not be construed as limiting the disclosure to the specifically stated amino acid substitution.

According to some embodiments, the subject comprising the cancer harboring the non-V600E/K BRAF mutation is a mammal. According to some embodiments, the mammal is selected from the group consisting of humans, primates, farm animals, and domestic animals. According to some embodiments, the mammal is a human.

According to some aspects, the present disclosure provides both solid and hematologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver tumor/cancer, lung tumor/cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi’s sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms’ tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

According to some embodiments, the subject’s cancer is selected from the group consisting of glioblastoma, melanoma, cholangio carcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer. Preferably, the cancer is selected from the group consisting of small intestine cancer, non-small cell lung cancer, gallbladder cancer, and squamous cell cancer.

According to some aspects, the present disclosure provides administering to the subject at least one additional mitogen-activated protein kinase (MAPK) pathway inhibitor. According to some embodiments, the at least one additional therapeutic agent is selected from the group consisting of an MEK inhibitor, a RAF inhibitor, an HDAC inhibitor, an ERK inhibitor, and combinations thereof.

As used herein, a "mitogen-activated protein kinase (MAPK) pathway inhibitor" is any substance that modulates, for example reduces, the activity, expression or phosphorylation of proteins in the MAPK pathway that result in a reduction of cell growth or an increase in cell death.

An overview of the mammalian MAPK cascades is shown in FIG. 1. The details of the MAPK pathways are reviewed in e.g., Akinleye et al., 2013. Briefly, with respect to the ERK1/2 module in FIG. 1 (light purple box), the MAPK 1/2 signaling cascade is activated by ligand binding to receptor tyrosine kinases (RTK). The activated receptors recruit and phosphorylate adaptor proteins Grb2 and SOS, which then interact with membrane-bound GTPase Ras and cause its activation. In its activated GTP-bound form, Ras recruits and activates Raf kinases (A-Raf, B-Raf, and C-Raf/RaF-1). The activated Raf kinases activate MAPK 1/2 (MKK1/2), which in turn catalyzes the phosphorylation of threonine and tyrosine residues in the activation sequence Thr-Glu-Tyr of ERK1/2. With respect to the JNK/p38 module (yellow box in FIG. 1), upstream kinases, MAP3Ks, such as MEKK1/4, ASK1/2, and MLK1/2/3, activate MAP2K3/6 (MKK3/6), MAP2K4 (MKK4), and MAP2K7 (MKK7). These MAP2Ks then activate JNK protein kinases, including JNK1, JNK2, and JNK3, as well as p38 α/β/γ/Δ. To execute their functions, JNKs activate several transcription factors, including c-Jun, ATF-2, NF-ATc1, HSF-1 and STAT3. With respect to the ERK5 module (blue box in FIG. 1), the kinases upstream of MAP2K5 (MKK5) are MEKK2 and MEKK3. The best characterized downstream target of MEK5 is ERK5, also known as big MAP kinase 1 (BMK1) because it is twice the size of other MAPKs.

Non-limiting examples of MAPK pathway inhibitors include RAS inhibitors, RAF inhibitors, MEK inhibitors, ERK1/2 inhibitors, pharmaceutically acceptable salts thereof, and combinations thereof.

As used herein, a "RAS inhibitor" means those substances that (i) directly interact with RAS, e.g., by binding to RAS and (ii) decrease the expression or the activity of RAS. Non-limiting exemplary RAS inhibitors include, but are not limited to, farnesyl transferase inhibitors (such as, e.g., tipifarnib and lonafamib), farnesyl group-containing small molecules (such as, e.g., salirasib and TLN-4601), DCAI, as disclosed by Maurer (Maurer et al., 2012), Kobe0065 and Kobe2602, as disclosed by Shima (Shima et al., 2013), HBS 3 (Patgiri et al., 2011), and AIK-4 (Allinky).

As used herein, a "RAF inhibitor" means those substances that (i) directly interact with RAF, e.g., by binding to RAF and (ii) decrease the expression or the activity of RAF, such as, e.g., A-RAF, B-RAF, and C-RAF (Raf-1). Non-limiting exemplary RAF inhibitors include:

Compound 7

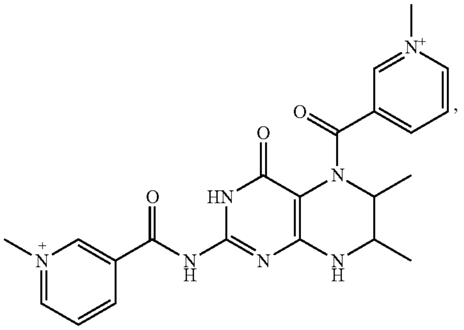

(Li et al.)

Compound 9

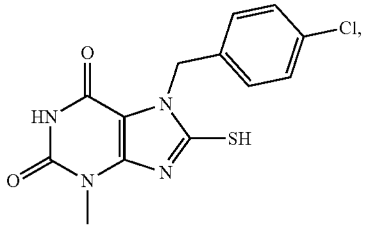

(Id.)

Compound 10

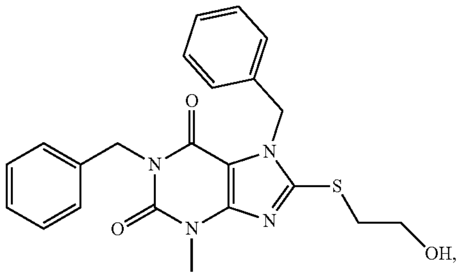

(Id.)

Compound 13

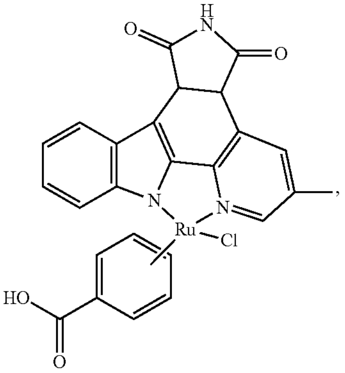

(Id.)

-continued
Compound 14
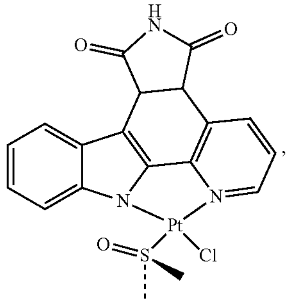
(Id.)
Compound 15
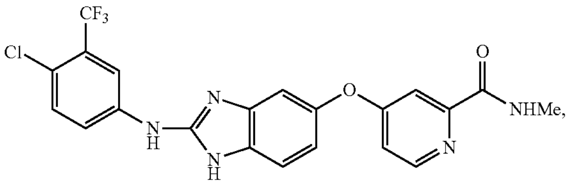
(Id.)
Compound 16
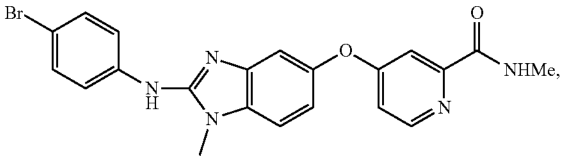
(Id.)
Compound 18
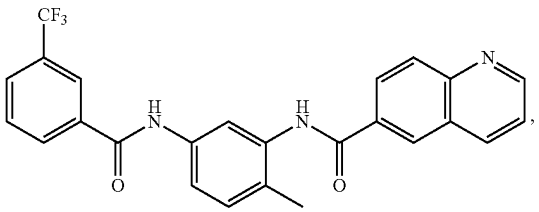
(Id.)
Compound 19
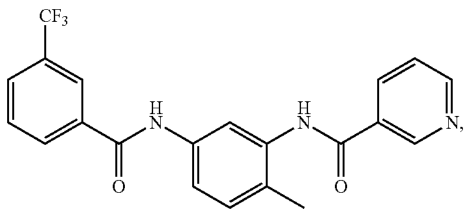
(Id.)
-continued
Compound 20
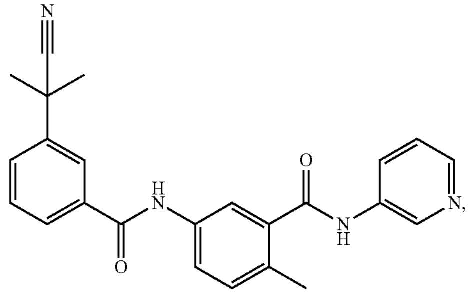
(Id.)
Compound 21
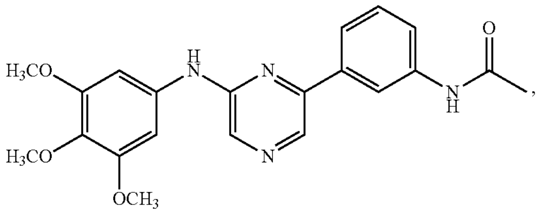
(Id.)
Compound 22
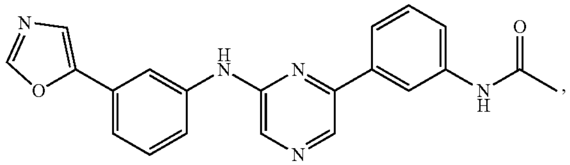
(Id.)
Compound 23
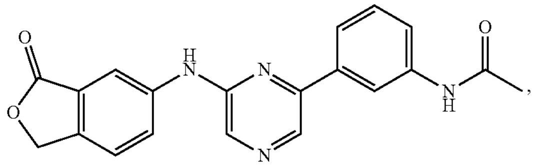
(Id.)
Compound 24
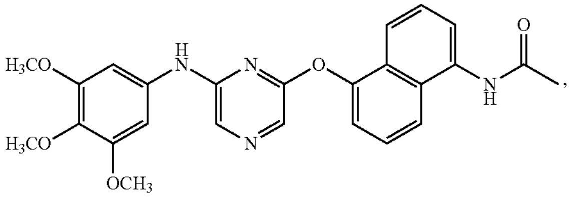
(Id.)
Compound 25
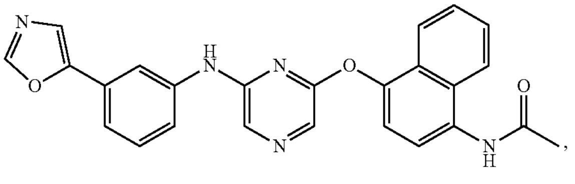
(Id.)

-continued
Compound 26
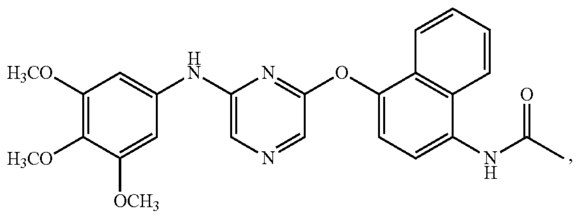
(Id.)
Compound 27
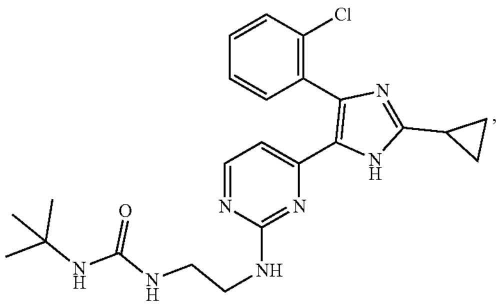
(Id.)
Compound 28
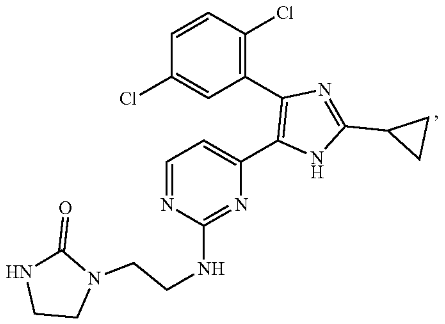
(Id.)
Compound 30
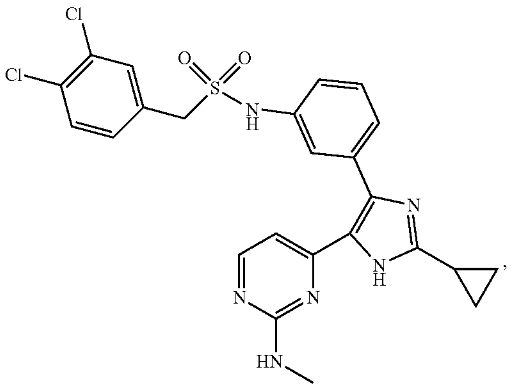
(Id.)
-continued
Compound 31
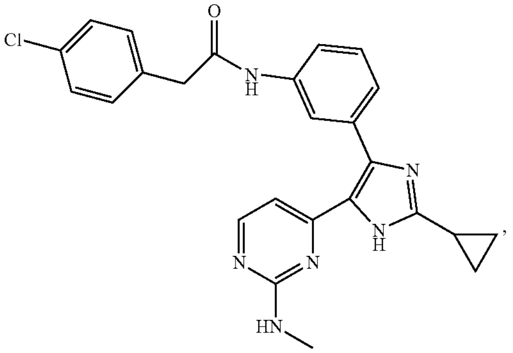
(Id.)
Compound 32
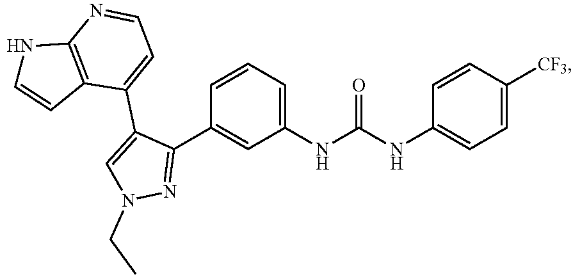
(Id.)
Compound 33
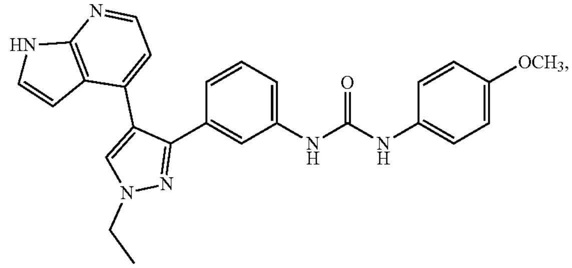
(Id.)
Compound 34
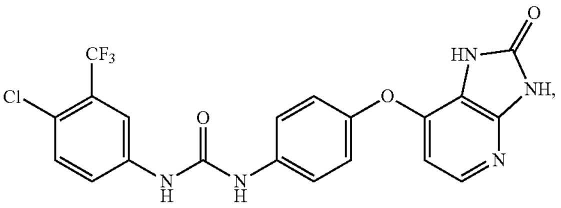
(Id.)

Compound 35

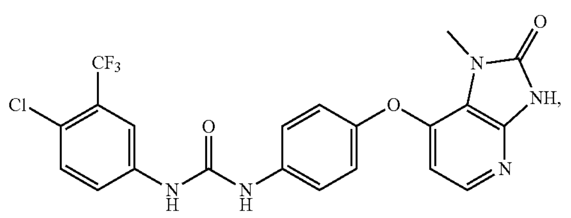

(Id.)

Compound 36

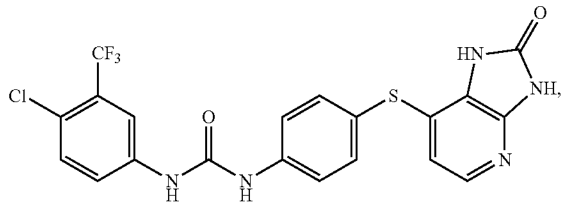

(Id.)

Compound 37

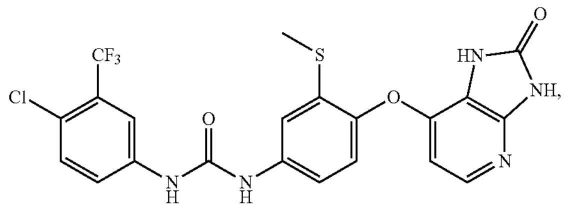

(Id.)

Compound 38

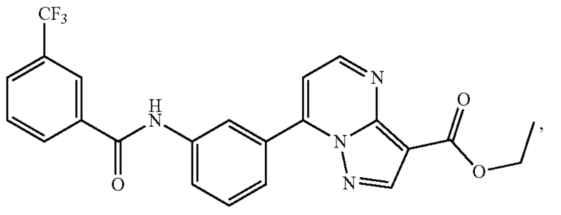

(Id.)

Compound 39

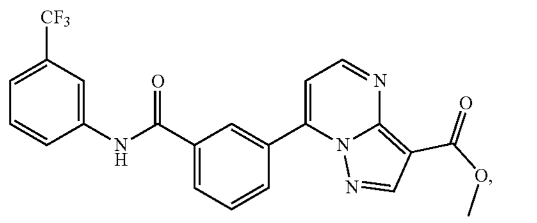

(Id.)

Compound 40

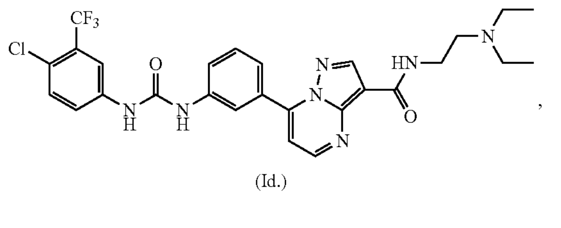

(Id.)

AAL881 (Novartis); AB-024 (Ambit Biosciences), ARQ-736 (ArQule), ARQ-761 (ArQule), AZ628 (Axon Medchem BV), BAY 43-9006 sorafenib, BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca (SEQ ID NO: 45)) and 523 (cctatcgttagagtcttcctg (SEQ ID NO: 46)) (Liu et al., 2007), CHIR-265 (Novartis), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LXH254 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), PLX3603 (Daiichi Sankyo), PLX8394 (Daiichi Sankyo), RAF-265 (Novartis), RAF-365 (Novartis), REDX0535 (RedX Pharma Plc), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

According to some embodiments, RAF inhibitors include pan-inhibitors; non-limiting examples of which include erlotinib (Tarceva), gefitinib (Iressa), imatinib mesylate (Gleevec), lapatinib (Tyverb), sunitinib malate (Sutent) pharmaceutically acceptable salts thereof, and combinations thereof.

As used herein, a "MEK inhibitor" means those substances that (i) directly interact with MEK, e.g., by binding to MEK and (ii) decrease the expression or the activity of MEK. Thus, inhibitors that act upstream of MEK, such as RAS inhibitors and RAF inhibitors, are not MEF inhibitors according to the present invention. Non-limiting examples of MEK inhibitors include anthrax toxin, antroquinonol (Golden Biotechnology), ARRY-142886 (6-(4-bromo-2-chloro-phenylamino)-7-fluoro-3-methyl-3H-benzoimidazole-5-c-arboxylic acid (2-hydroxy-ethoxy)-amide) (Array BioPharma), ARRY-438162 (Array BioPharma), binimetinib (MEK162, ARRY-1662), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxphenyl)-oxanaphthalen-4-one) (Pfizer), PD 184352 (CI-1040) (Pfizer), PD-0325901 (Pfizer), pimasertib (Santhera Pharmaceuticals), RDEA119 (Ardea Biosciences/Bayer), refametinib (AstraZeneca), RG422 (Chugai Pharmaceutical Co.), R0092210 (Roche), R04987655 (Hoffmann-La Roche), R05126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio) butadiene) (Sigma), WX-554 (Wilex), YopJ polypeptide (Mittal et al., 2010), pharmaceutically acceptable salts thereof, and combinations thereof.

As used herein, an "ERK1/2 inhibitor" means those substances that (i) directly interact with ERK1 and/or ERK2, e.g., by binding to ERK1/2 and (ii) decrease the expression or the activity of ERK1 and/or ERK2 protein kinases. Therefore, inhibitors that act upstream of ERK1/2, such as MEK inhibitors and RAF inhibitors, are not ERK1/2 inhibitors according to the present invention. Non-limiting examples of an ERK1/2 inhibitor include AEZS-131 (Aeterna Zentaris), AEZS-136 (Aeterna Zentaris), BVD-523, SCH-722984 (Merck & Co.), SCH-772984 (Merck &

Co.), SCH-900353 (MK-8353) (Merck & Co.), LY3214996 (Lilly), pharmaceutically acceptable salts thereof, and combinations thereof.

As used herein, an "HDAC inhibitor" means those substances that (i) directly interact with a histone deacetylase (HDAC), e.g., by binding to HDAC, and (ii) decrease the expression or activity of the HDAC. Non-limiting examples of HDAC inhibitors include Abexinostat (PCI-24781), Givinostat, Entinostat, Vorinostat, CI-994, CUDC-101 Entinostat, BML-210, M344, NVP-LAQ824, Panobinostat, Pracinosat (SB939), Mocetinostat, Resminostat, Romidepsin, Belinostat, pharmaceutically acceptable salts thereof, and combinations thereof.

According to some embodiments, the HDAC inhibitor is selected from the group consisting of Vorinostat, Panobinostat, Romidepsin, Belinostat, pharmaceutically acceptable salts thereof, and combinations thereof.

In another aspect, the method further comprises administering to the subject at least one additional therapeutic agent effective for treating or ameliorating the effects of the cancer. The additional therapeutic agent may be selected from the group consisting of an antibody, an antibody fragment, an antibody conjugate, a cytotoxic agent, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F(ab')2, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Brentuximab Vedotin (Adcetriz), Ado-trastuzumab emtansine (Kadcyla), Cetuximab (Erbitux), bevacizumab (Avastin), Ibritumomab (Zevalin), vedolizumab (Entyvio), Ipilimumab (Yervoy), Nivolumab (Opdivo), pembrolizumab (Keytruda), Alemtuzamab atezolizumab (Tecentriq), avelumab (Bavencio), durvalumab (Imfinzi), B-701, Ofatumumab, Obinutuzumab (Gazyva) Panitumumab, plozalizumab, BI-754091, OREG-103, COM-701, BI-754111, and combinations thereof.

According to some embodiments, the antibody, fragment thereof, or conjugate thereof is selected from the group consisting of rituximab (Rituxan), Brentuximab Vedotin (Adcetriz), Ado-trastuzumab emtansine (Kadcyla), Ipilimumab (Yervoy), Nivolumab (Opdivo), pembrolizumab (Keytruda), Alemtuzamab atezolizumab (Tecentriq), durvalumab (Imfinzi), Ofatumumab, Obinutuzumab (Gazyva) Panitumumab, and combinations thereof.

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation vinca alkaloids, paclitaxel (Taxol®), docetaxel (TaxotereR), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

According to some embodiments, the cytotoxic agent is selected from the group consisting of cyclophosphamide, mechlorethamine, uramustine, melphalan, chlorambucil, ifosfamide, carmustine, lomustine, streptozocin, busulfan, temozolomide, cisplatin, carboplatin, oxaliplatin, nedaplatin, satraplatin, triplatin tetranitrate, doxorubicin, daunorubicin, idarubicin, mitoxantrone, methotrexate, pemetrexed, 6-mercaptopurine, dacarbazine, fludarabine, 5-fluorouracil, arabinosylcytosine, capecitabine, gemcitabine, decitabine, vinca alkaloids, paclitaxel (Taxol), docetaxel (Taxotere), ixabepilone (Ixempra), actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include an inhibitor of the PI3K/Akt pathway. Non-limiting examples of an inhibitor of the PI3K/Akt pathway include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), BVD-723, CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof.

In the present invention, BVD-723 is a compound according to formula (II):

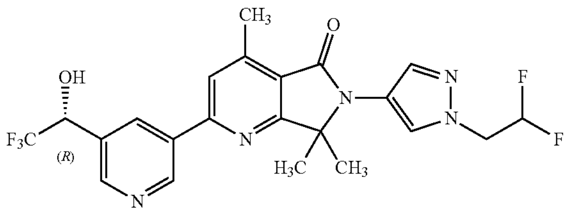

and pharmaceutically acceptable salts thereof. BVD-723 is a selective inhibitor of PI3Kγ. BVD-723 may be synthesized according to the methods disclosed in, e.g., U.S. Pub. No. 2016/0214980, which is incorporated herein by reference in its entirety. Enantiomers and racemic mixtures of both enantiomers of BVD-723 are also contemplated within the scope of the present invention.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), LAG-3, IMP-321, JCAR-014, ASLAN-002 (BMS-777607), interferons, imiquimod and cellular membrane fractions from bacteria, IL-2, IL-7, IL-12, CCL3, CCL26, CXCL7, synthetic cytosine phosphate-guanosine (CpG), immune-checkpoint inhibitors, and combinations thereof.

In the present invention, the term "photoactive therapeutic agent" means compounds and compositions that become active upon exposure to light. Certain examples of photoactive therapeutic agents are disclosed, e.g., in U.S. Patent Application Serial No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate, and combination thereof.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerianormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

According to one aspect, the present disclosure provides a method for treating or ameliorating the effects of a cancer in a subject comprising (a) identifying a subject with a cancer harboring a non-V600E/K BRAF mutation; and (b) administering to the subject an effective amount of an ERK inhibitor or a pharmaceutically acceptable salt thereof.

According to one embodiment, the ERK inhibitor is selected from the group consisting of BVD-523, SCH-722984 (Merck & Co.), SCH-772984 (Merck & Co.), SCH-900353 (MK-8353) (Merck & Co.), LY3214996 (Lilly), AEZS-140 (Aeterna Zentaris), AEZS-131 (Aeterna Zentaris), AEZS-136 (Aeterna Zentaris), LTT-462 (Novartis), RG-7842 (Genentech), CC-90003 (Celgene), KIN-4050 (Kinentia), and combinations thereof. According to one embodiment, the ERK inhibitor is BVD-523. In one aspect of this embodiment, the BVD-523 or a pharmaceutically acceptable salt thereof is administered in the form of a pharmaceutical composition further comprising a pharmaceutically acceptable carrier or diluent.

According to one aspect, the present disclosure provides identifying a subject with a cancer harboring a non-V600E/K BRAF mutation comprising (i) obtaining a biological sample from the subject; and (ii) screening the sample to determine whether the subject has a non-V600E/K BRAF mutation.

Suitable and preferred subjects are as disclosed herein. In this embodiment, the methods may be used to treat the cancers disclosed above, including those cancers with the mutational backgrounds identified above. Methods of identifying such mutations are also as set forth above.

In the present invention, biological samples include, but are not limited to, blood, plasma, urine, skin, saliva, and biopsies. Biological samples are obtained from a subject by routine procedures and methods which are known in the art. Non-limiting examples of methods for identifying mutations include PCR, sequencing, hybrid capture, in-solution capture, molecular inversion probes, fluorescent in situ hybridization (FISH) assays, and According to one embodiment, the method further comprises administering to the subject at least one additional therapeutic agent selected from the group consisting of an MEK inhibitor, a RAF inhibitor, an HDAC inhibitor, and combinations thereof. Suitable and preferred subjects are as disclosed herein. In this embodiment, the methods may be used to treat the cancers disclosed above, including those cancers with the mutational backgrounds identified above, using one or more of the additional therapeutic agents disclosed above. Methods of identifying such mutations are also as set forth above.

According to one aspect, the present disclosure provides a method for identifying a subject having cancer who would benefit from therapy with an ERK inhibitor or a pharmaceutically acceptable salt thereof, the method comprising (a) obtaining a biological sample from the subject; and (b) screening the sample to determine whether the subject has a non-V600E/K BRAF mutation, wherein the presence of the non-V600E/K BRAF mutation confirms that the subject would benefit from therapy with an ERK inhibitor or a pharmaceutically acceptable salt thereof. According to some embodiments, the method further comprises administering an ERK inhibitor to the subject or a pharmaceutically acceptable salt thereof. According to some embodiments, the method further comprises administering to the subject at least one additional therapeutic agent. In this embodiment, the method may be used to identify the mutational background identified above in the cancers described above. The methods of identifying such mutations are also as set forth above. In this embodiment, the ERK inhibitor that the identified patient would benefit from is as described above. Additional therapeutic agents are as disclosed above. Suitable and preferred subjects are as disclosed above.

According to one aspect, the present disclosure provides a method for treating or ameliorating the effects of a cancer in a subject comprising (a) identifying a subject with a cancer harboring a non-V600E/K BRAF mutation; and (b) administering to the subject an effective amount of BVD-523 or a pharmaceutically acceptable salt thereof. According to one aspect, the present disclosure provides a method for identifying a subject having cancer who would benefit from therapy with BVD-523 or a pharmaceutically acceptable salt thereof, the method comprising (a) obtaining a biological sample from the subject; and (b) screening the sample to determine whether the subject has a non-V600E/K BRAF mutation, wherein the presence of the non-V600E/K BRAF mutation confirms that the subject would benefit from therapy with BVD-523 or a pharmaceutically acceptable salt thereof. In these embodiments, the method may be used to identify the mutational background identified above in the cancers described above. The methods of identifying such mutations are also as set forth above. Suitable and preferred subjects are as disclosed above.

A further aspect of the present disclosure provides a kit for treating or ameliorating the effects of a cancer in a subject harboring a non-V600E/K BRAF mutation. According to some embodiments, the kit comprises an effective amount of an ERK inhibitor as described above, and optionally an additional therapeutic agent as described above.

The kits may also include suitable storage containers, e.g., ampules, vials, tubes, etc., for each anti-cancer agent of the present invention (which may e.g., may be in the form of pharmaceutical compositions) and other reagents, e.g., buffers, balanced salt solutions, etc., for use in administering the anti-cancer agents to subjects. The anti-cancer agents of the invention and other reagents may be present in the kits in any convenient form, such as, e.g., in a solution or in a powder form. The kits may further include a packaging container, optionally having one or more partitions for housing the pharmaceutical composition and other optional reagents.

In the present invention, an "effective amount" or a "therapeutically effective amount" of an anti-cancer agent of the invention including pharmaceutical compositions containing same that are disclosed herein is an amount of such agent or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of an agent or composition according to the invention will be that amount of the agent or composition, which is the lowest dose effective to produce the desired effect. The effective dose of an agent or composition of the present invention may be administered as two, three, four, five, six or more sub-doses, administered separately at appropriate intervals throughout the day.

A suitable, non-limiting example of a dosage of BVD-523, a RAF inhibitor, an ERK inhibitor, or another anti-cancer agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg. 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of BVD-523, RAF inhibitors, ERK inhibitors, or other anti-cancer agents disclosed herein may be administered as two, three, four, five, six or more sub-doses, administered separately at appropriate intervals throughout the day.

The BVD-523, RAF inhibitors, ERK inhibitors, or other therapeutic agents or pharmaceutical compositions containing same of the present invention may be administered in any desired and effective manner: for oral ingestion, or as an ointment or drop for local administration to the eyes, or for parenteral or other administration in any appropriate manner such as intraperitoneal, intratumoral, subcutaneous, topical, intradermal, inhalation, intrapulmonary, rectal, vaginal, sublingual, intramuscular, intravenous, intraarterial, intrathecal, or intralymphatic. Further, the BVD-523, RAF inhibitors or other therapeutic agents or pharmaceutical compositions containing same of the present invention may be administered in conjunction with other treatments. The BVD-523, RAF inhibitors or other therapeutic agents or pharmaceutical compositions containing the same may be encapsulated or otherwise protected against gastric or other secretions, if desired.

The pharmaceutical compositions of the invention comprise one or more active ingredients, e.g. therapeutic agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.).

Pharmaceutically acceptable diluents or carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The following examples are provided to further illustrate the methods of the present invention. These examples are illustrative only and are not intended to limit the scope of the invention in any way.

Example 1

Figure 2:
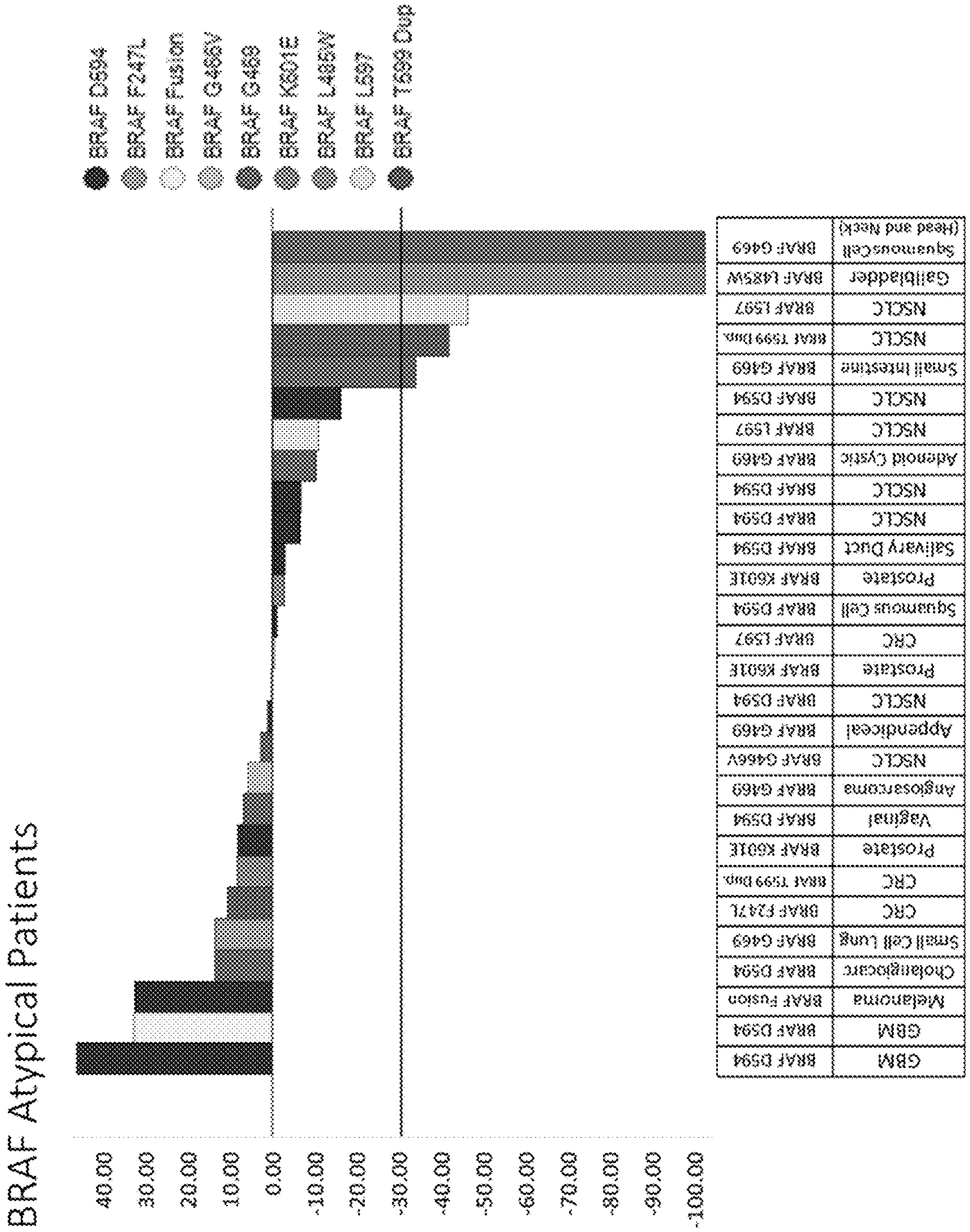
FIG. 2 shows the response in patients treated with BVD-523. Included are all patients with disease measured by RECIST v1.1 who received one dose or greater of study treatment and greater than 1 on-treatment tumor assessment. Response was measured as the change from baseline in the sum of the longest diameter of each target lesion. The solid line indicates the threshold for a partial response according to RECIST v1.1. Abbreviations: GBM, glioblastoma: NSCLC, non-small cell lung cancer: CRC, colorectal cancer. Atypical BRAF mutation associated with each patient's cancer is indicated.

The following example shows the results of the solid tumor Phase 1b trial of BVD-523. The waterfall plot depicted in FIG. 2 provides an illustration of human clinical trial patient information showing each individual patient's response to treatment with BVD-523, as measured by % change in tumor burden. Patients generally received 600 mg, twice daily (BID), with some patients receiving a deescalated dose of 300 mg-400 mg BID if side effects were not manageable with other palliative medication.

As shown in FIG. 2, tumor response to BVD-523 was assessed in 28 evaluable patients using Response Evaluation Criteria in Solid Tumors version 1.1 (RECIST v1.1). One patient did not receive both scans of target lesions and was thus not evaluated. The horizontal axis across the plot serves as a baseline measurement for each patient. The vertical axis is a measure of the maximum percentage change from baseline; i.e., percent growth or reduction of tumor burden by radiologic measurement according to RECIST v1.1. Radiologic measurement comprised computed tomography (CT) scan and, rarely, magnetic resonance imaging (MRI).

The tumor burden data represented by FIG. 2 is arranged from the worst value (i.e. greatest progression of tumor burden) on the left side of the plot to the best value (i.e., greatest reduction of tumor burden) on the right side of the plot. RECIST v1.1 response criteria for measured target lesions have been described previously. (See Eisenhauer, E. A., et al., New response evaluation criteria in solid tumours: Revised RECIST guideline (version 1.1), European J. of Cancer 45, 228-247 (2009), incorporated by reference herein in its entirety). The response criteria is as follows:

- Complete Response (CR)—disappearance of all target lesions;
- Partial Response (PR)—at least a 30% decrease in the sum of diameters of target lesions, taking as reference the baseline sum diameters; as shown in FIG. 2, the 30% decrease threshold for partial response is indicated by horizontal line;
- Progressive Disease (PD)—at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (Note: the appearance of one or more new lesions is also considered progressions);
- Stable Disease (SD)—neither sufficient shrinkage to qualify for PR nor sufficient increase to qualify for PD, taking as reference the smallest sum diameters while on study.

FIG. 2 also shows the type of cancer or organ where the tumor burden was measured for each patient, and the type of atypical BRAF mutation identified in that patient's tumor sample. Of the 28 patients represented, 13 patient tumors comprised a BRAF D594 mutation (seven were D594G and six were D594N): 1 patient tumor comprised a BRAF F247L mutation: 1 patient tumor comprised a BRAF gene fusion with Nuclear Factor IC (NFIC) gene (i.e. BRAF-NFIC Fusion mutation): 1 patient tumor comprised a BRAF G466V mutation: 5 patient tumors comprised a BRAF G469 mutation (one was G469V and four were G469A): 3 patient tumors comprised a BRAF K601E mutation: 1 patient tumor comprised a BRAF L485W mutation: 3 patient tumors comprised a BRAF L597 mutation (one was undefined and two were L597Q), and 2 patient tumors comprised a T599 Duplication. Type of BRAF mutation is indicated by color code and by cancer type for each patient (See FIG. 2).

Five PR patients had between 35% to 100% reduction in the sum of target lesions from baseline. Those patients displayed: a gallbladder tumor comprising a L485W mutation; a squamous cell tumor of the head/neck comprising a G469A mutation; non-small cell lung carcinoma comprising a BRAF L597Q mutation or BRAF T599 duplication; and a tumor of the small intestine comprising a BRAF G469A mutation. Stable disease was demonstrated in 19 patients. Three patients displayed progressive disease at first evaluation. (See FIG. 2). Thus, BVD-523 treatment surprisingly resulted in partial response or stable disease in 24 out of 28 patients with atypical (i.e. non-V600E/K) BRAF mutations.

Figure 3:
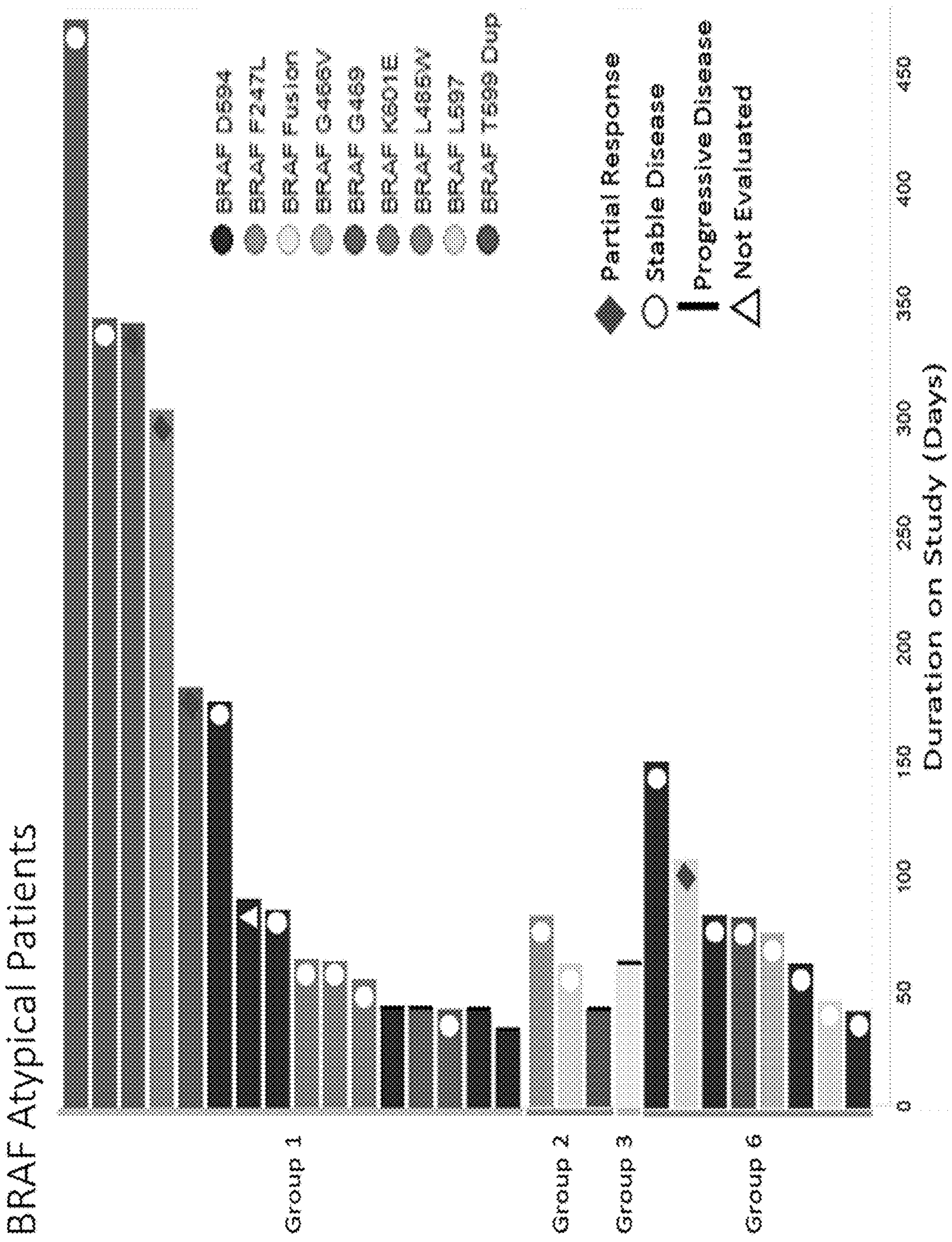
FIG. 3 shows duration of treatment in a Swimmer's plot categorized by group. Members of Group 1 are any patients with any BRAF mutation in any tumor type other than colorectal cancer (CRC) and non-small cell lung carcinoma (NSCLC), and that have not been previously treated with a MAPK pathway inhibitor. The members of Group 2 are patients with any BRAF mutation in CRC that have not been previously treated with a MAPK pathway inhibitor. The members of Group 3 are patients having a tumor with a BRAF V600E/K mutation that is refractory to MAPK inhibitor. The members of Group 6 are patients with any BRAF mutation present in NSCLC.

FIG. 3 shows duration of treatment in a Swimmer's plot categorized by group. Members of Group 1 are any patients with any BRAF mutation in any tumor type other than colorectal cancer (CRC) and non-small cell lung carcinoma (NSCLC), and that have not been previously treated with a MAPK pathway inhibitor. The members of Group 2 are patients with any BRAF mutation in CRC that have not been previously treated with a MAPK pathway inhibitor. The members of Group 3 are patients having a tumor with a BRAF V600E/K mutation that is refractory to MAPK inhibitor treatment. The members of Group 6 are patients with any BRAF mutation present in NSCLC. As shown in FIG. 3, all 28 patients are included as represented by the horizontal bars, one for each subject. The duration of treatment for each subject in each group is illustrated from the top (longest treatment duration) to bottom (least treatment duration) of the groups. The horizontal axis represents the duration, in days, that the patient was on the study. FIG. 3 also shows the type of response achieved for each patient according to RECIST v1.1 (diamond=partial response; circle=stable disease; vertical bar=progressive disease: triangle=not evaluated).

Figure 4:
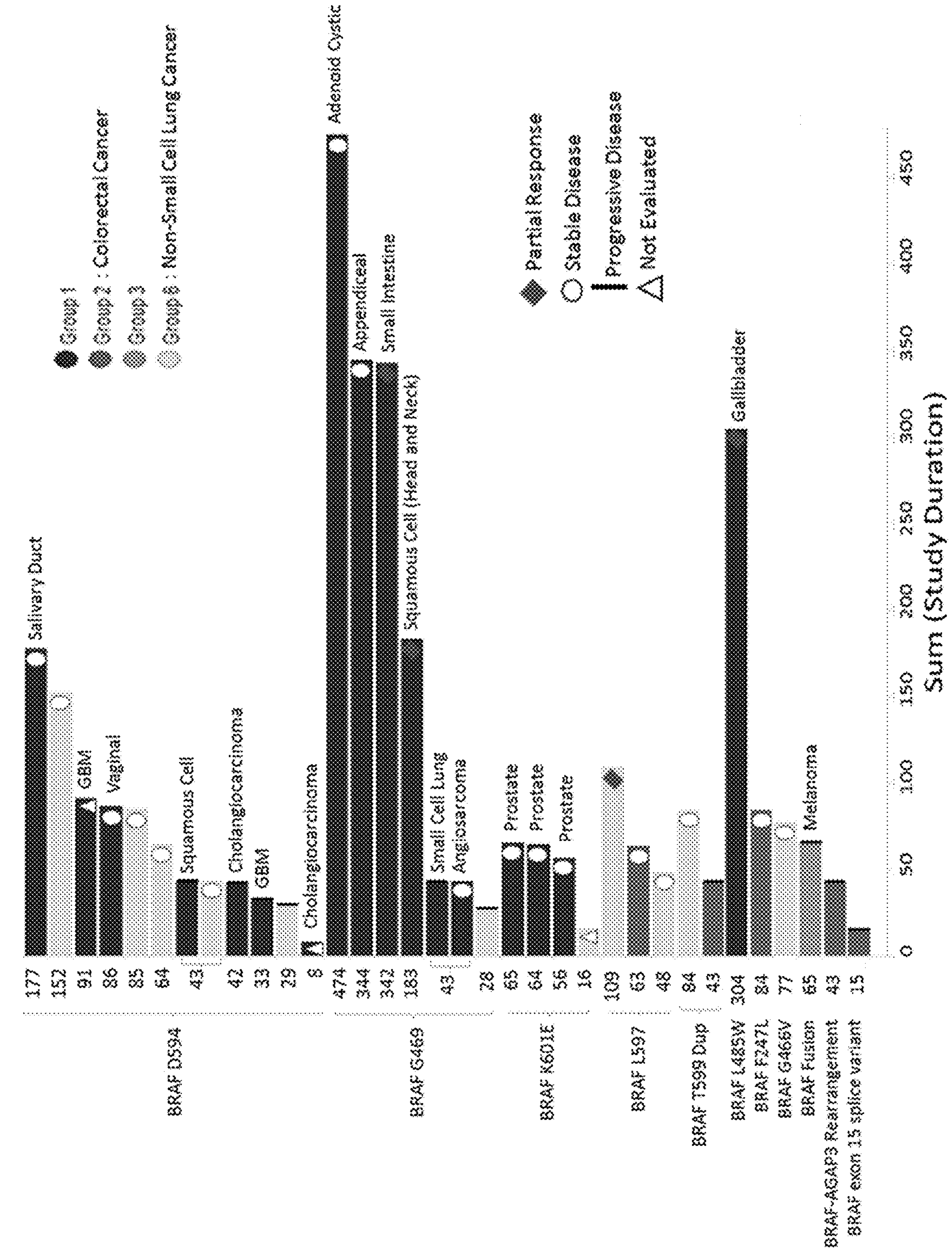
FIG. 4 shows duration of treatment in a Swimmer's plot broken down by BRAF mutation. All 28 patients measured for RECIST v1.1 response criteria are included, plus additional patients not evaluated by RECIST v1.1 (diamond=partial response; circle=stable disease; vertical bar=progressive disease; triangle=not evaluated).

FIG. 4 shows duration of treatment in a waterfall plot broken down by BRAF mutation. All 28 patients measured for RECIST v1.1 response criteria are included, plus additional patients not evaluated by RECIST v1.1 (diamond=partial response; circle=stable disease: vertical bar=progressive disease; triangle=not evaluated). The mean duration of BVD-523 treatment before discontinuation for tumors harboring the same BRAF mutation was: D594, 73.6 days; G469, 208.14 days: K601E, 50.25 days: L597, 73.3 days; T599 Dup, 63.5 days. For single patient representatives of specific BRAF mutations, the duration of treatment was: L485W, 304 days: F247L, 84 days: G466V, 77 days: BRAF fusion, 65 days: BRAF-AGAP3 rearrangement, 43 days: BRAF exon 15 splice variant, 15 days. By genomic screening of cancer patients for BRAF mutation and treating them prior to full in vitro characterization of those mutations (as a driver mutation), BVD-523 is shown to be useful to interrogate and discover efficacious treatment options for patients carrying mutations in BRAF. The clinical population of patients and the efficacy is not defined primarily by tumor type, but rather mutational status of enzymes such as BRAF, upstream of ERK 1/2 kinase activation.

In summary, the provided examples present data from the solid tumor Phase 1b trial of BVD-523, a novel ERK inhibitor, as a treatment for patients with cancers harboring atypical BRAF mutations. Continuous, twice-daily treatment with BVD-523 resulted in antitumor effects in several patients, and was not limited to any one specific cancer type or atypical BRAF mutation.

DOCUMENTS

ABSALAN, Farnaz, Mostafa Ronaghi (2008). Molecular Inversion Probe Assay. Methods in Molecular Biology 396. Humana Press. pp. 315-330.

AHRONIAN L G, Sennott E M, Van Allen E M, Wagle N, Kwak E L, Faris J E, et al. Clinical acquired resistance to RAF inhibitor combinations in BRAF-mutant colorectal cancer through MAPK pathway alterations. Cancer Discov 2015:5:358-67.

ARCILA M E, Drilon A, Sylvester B E, Lovly C M, Borsu L, Reva B, et al. MAP2K1 (MEK1) mutations define a distinct subset of lung adenocarcinoma associated with smoking. Clin Cancer Res 2015:21:1935-43.

ARONOV A M, Baker C, Bemis G W, Cao J, Chen G, Ford P J, et al. Flipped out: structure-guided design of selective pyrazolylpyrrole ERK inhibitors. J Med Chem 2007:50:1280-7.

ARONOV A M, Tang Q, Martinez-Botella G, Bemis G W, Cao J, Chen G, et al. Structure-guided design of potent and selective pyrimidylpyrrole inhibitors of extracellular signal-regulated kinase (ERK) using conformational control. J Med Chem 2009:52:6362-8.

ARRINGTON A K, Heinrich E L, Lee W, Duldulao M, Patel S, Sanchez J, et al. Prognostic and predictive roles of KRAS mutation in colorectal cancer. Int J Mol Sci 2012:13:12153-68.

CARGNELLO M, Roux P P. Activation and function of the MAPKs and their substrates, the MAPK-activated protein kinases. Microbiol Mol Biol Rev 2011:75:50-83.

CARLINO M S, Fung C, Shahheydari H, Todd J R, Boyd S C, Irvine M, et al. Preexisting MEKIP124 mutations diminish response to BRAF inhibitors in metastatic melanoma patients. Clin Cancer Res 2015:21:98-105.

CHAPMAN P B, Hauschild A, Robert C, Haanen J B, Ascierto P, Larkin J, et al. Improved survival with vemurafenib in melanoma with BRAF V600E mutation. N Engl J Med 2011; 364:2507-16.

CORCORAN, R. B., et al. BRAF gene amplification can promote acquired resistance to MEK inhibitors in cancer cells harboring the BRAF V600E mutation. Sci Signal (2010); 3 (149): ra84.

DAI, B., et al. STAT3 mediates resistance to MEK inhibitor through microRNA miR-17. Cancer Res (2011); 71:3658-3668.

DAVIES H, Bignell G R, Cox C, Stephens P, Edkins S, Clegg S, et al. Mutations of the BRAF gene in human cancer. Nature 2002; 417:949-54.

DESCHENES-SIMARD X, Kottakis F, Meloche S, Ferbeyre G. ERKs in cancer: friends or foes? Cancer Res 2014; 74:412-9.

DOBRZYCKA B, Terlikowski S J, Kowalczuk O, Niklinska W, Chyczewski L, Kulikowski M. Mutations in the KRAS gene in ovarian tumors. Folia Histochem Cytobiol 2009:47:221-4.

EMERY, C. M., et al. MEK1 mutations confer resistance to MEK and B-RAF inhibition. PNAS (2009); 106 (48): 20411-6.

FEDOROV O, Niesen F H, Knapp S. Kinase inhibitor selectivity profiling using differential scanning fluorimetry. Methods Mol Biol 2012; 795:109-18.

FERNÁNDEZ-MEDARDE A, Santos E. Ras in cancer and developmental diseases. Genes Cancer 2011; 2:344-58.

FLAHERTY K T, Infante J R, Daud A, Gonzalez R, Kefford R F, Sosman J, et al. Combined BRAF and MEK inhibition in melanoma with BRAF V600 mutations. N Engl J Med 2012; 367:1694-703.

GOETZ E M, Ghandi M, Treacy D J, Wagle N, Garraway L A. ERK mutations confer resistance to mitogen-activated protein kinase pathway inhibitors. Cancer Res 2014; 74:7079-89.

GOLLOB J A, Wilhelm S, Carter C, Kelley S L. Role of Raf kinase in cancer: therapeutic potential of targeting the Raf/MEK/ERK signal transduction pathway. Semin Oncol 2006; 33:392-406.

GREGER, James G., et al. "Combinations of BRAF, MEK, and PI3K/mTOR inhibitors overcome acquired resistance to the BRAF inhibitor GSK2118436 dabrafenib, mediated by NRAS or MEK mutations." Molecular cancer therapeutics 11.4 (2012): 909-920.

GROENENDIJK F H, Bernards R. Drug resistance to targeted therapies: deja vu all over again. Mol Oncol 2014:8:1067-83.

HALL R D, Kudchadkar R R. BRAF mutations: signaling, epidemiology, and clinical experience in multiple malignancies. Cancer Control 2014; 21:221-30.

HARDENBOL, P., et al. Multiplexed genotyping with sequence-tagged molecular inversion probes. Nat. Biotechnol. 2003, no. 21, p. 673-678.

HATZIVASSILIOU, Georgia, et al. "RAF inhibitors prime wild-type RAF to activate the MAPK pathway and enhance growth." Nature 464.7287 (2010): 431-435.

HATZIVASSILIOU G, Liu B, O'Brien C, Spoerke J M, Hoeflich K P, Haverty P M, et al. ERK inhibition overcomes acquired resistance to MEK inhibitors. Mol Cancer Ther 2012; 11:1143-54.

HAUSCHILD A, Grob J-J, Demidov L V, Jouary T, Gutzmer R, Millward M, et al. Dabrafenib in BRAF-mutated metastatic melanoma: a multicentre, open-label, phase 3 randomised controlled trial. Lancet 2012: 380:358-65.

HAYES T K, Neel N F, Hu C, Gautam P, Chenard M, Long B, et al. Long-Term ERK Inhibition in KRAS-Mutant Pancreatic Cancer Is Associated with MYC Degradation and Senescence-like Growth Suppression. Cancer Cell 2016; 29:75-89.

HEZEL A F, Noel M S, Allen J N, Abrams T A, Yurgelun M, Faris J E, et al. Phase II study of gemcitabine, oxaliplatin in combination with panitumumab in KRAS wild-type unresectable or metastatic biliary tract and gallbladder cancer. Br J Cancer 2014; 111:430-6.

JHA S, Morris E J, Hruza A, Mansueto M S, Schroeder G, Arbanas J, et al. Dissecting therapeutic resistance to ERK inhibition. Mol Cancer Ther 2016; 15:548-59.

JOHANNESSEN, C. M., et al. COT/MAP3K8 drives resistance to RAF inhibition through MAP kinase pathway reactivation. Nature (2010); 468 (7326): 968-972.

JOHNSON D B, Menzies A M, Zimmer L, Eroglu Z, Ye F, Zhao S, et al. Acquired BRAF inhibitor resistance: A multicenter meta-analysis of the spectrum and frequencies, clinical behaviour, and phenotypic associations of resistance mechanisms. Eur J Cancer 2015; 51:2792-9.

KANDA M, Matthaei H, Wu J, Hong S M, Yu J, Borges M, et al. Presence of somatic Mutations in most early-stage pancreatic intraepithelial neoplasia. Gastroenterology 2012; 142:730-733.

KHATTAK M, Fisher R, Turajlic S, Larkin J. Targeted therapy and immunotherapy in advanced melanoma: an evolving paradigm. Ther Adv Med Oncol 2013; 5:105-18.

KING, Alastair J., et al. "Dabrafenib; preclinical characterization, increased efficacy when combined with trametinib, while BRAF/MEK tool combination reduced skin lesions." PloS one 8.7 (2013): e67583.

LARKIN J, Ascierto P A, Dreno B, Atkinson V, Liszkay G, Maio M, et al. Combined vemurafenib and cobimetinib in BRAF-mutated melanoma. N Engl J Med 2014; 371:1867-76.

LITTLE, A. S., et al., Amplification of the Driving Oncogene, KRAS or BRAF, Underpins Acquired Resistance to MEK1/2 Inhibitors in Colorectal Cancer Cells. Sci. Signal. 4, ral7 (2011).

LIU, Dingxie, et al. "BRAF V600E maintains proliferation, transformation, and tumorigenicity of BRAF-mutant papillary thyroid cancer cells." Journal of Clinical Endocrinology & Metabolism 92.6 (2007): 2264-2271.

LIU B, Fu L, Zhang C, Zhang L, Zhang Y, Ouyang L, et al. Computational design, chemical synthesis, and biological evaluation of a novel ERK inhibitor (BL-EI001) with apoptosis-inducing mechanisms in breast cancer. Oncotarget 2015; 6:6762-75.

LONG G V, Fung C, Menzies A M, Pupo G M, Carlino M S, Hyman J, et al. Increased MAPK reactivation in early resistance to dabrafenib/trametinib combination therapy of BRAF-mutant metastatic melanoma. Nat Commun 2014; 5:5694.

LONG G V, Stroyakovskiy D, Gogas H, Levchenko E, de Braud F, Larkin J, et al. Dabrafenib and trametinib versus dabrafenib and placebo for Val600 BRAF-mutant melanoma: a multicentre, double-blind, phase 3 randomised controlled trial. Lancet 2015:386:444-51.

MANANDHAR S P, Hildebrandt E R, Schmidt W K. Small-molecule inhibitors of the Rce1p CaaX protease. J Biomol Screen. 2007; 12 (7): 983-993.

MASSEY P R, Prasad V, Figg W D, Fojo T. Multiplying therapies and reducing toxicity in metastatic melanoma. Cancer Biol Ther 2015; 16:1014-8.

MAURER, T, Garrenton, L S, Oh, A, Pitts, K, Anderson, D J, Skelton, N J, Fauber, B P, Pan, B, Malek, S, Stokoe, D, Ludlam, M J C, Bowman, K K, Wu, J, Giannetti, A M, Starovasnik, M A, Mellman, I, Jackson, P K, Rudolph, J, Wang, W, Fang, G. Small-molecule ligands bind to a distinct pocket in Ras and inhibit SOS-mediated nucleotide exchange activity. PNAS. 2012; 109 (14): 5299-304.

MCARTHUR G A, Chapman P B, Robert C, Larkin J, Haanen J B, Dummer R, et al. Safety and efficacy of vemurafenib in BRAFv600E and BRAFv600K mutation-positive melanoma (BRIM-3): extended follow-up of a phase 3, randomised, open-label study. Lancet Oncol 2014; 15:323-32.

MEKINIST [package insert]. Research Triangle Park, NC: GlaxoSmithKline; 2014.

METZKER, Emerging technologies in DNA sequencing Genome Res. 2005. 15:1767-1776.

MITTAL, Rohit et al. "The acetyltransferase activity of the bacterial toxin YopJ of *Yersinia* is activated by eukaryotic host cell inositol hexakisphosphate." Journal of Biological Chemistry 285.26 (2010): 19927-19934.

MORRIS E J, Jha S, Restaino C R, Dayananth P, Zhu H, Cooper A, et al. Discovery of a novel ERK inhibitor with activity in models of acquired resistance to BRAF and MEK inhibitors. Cancer Discov 2013; 3:742-50.

NAZARIAN, R., et al. Melanomas acquire resistance to B-RAF (V600E) inhibition by RTK or N-RAS upregulation. Nature. 2010; 468 (7326): 973-977.

NIKOLAEV S I, Rimoldi D, Iseli C, Valsesia A, Robyr D, Gehrig C, et al. Exome sequencing identifies recurrent somatic MAP2K1 and MAP2K2 mutations in melanoma. Nat Genet 2012; 44:133-9.

NILSSON, M., et al. Padlock probes: circularizing oligonucleotides for localized DNA detection. Science. 1994, no. 265, p. 2085-2088.

O'HARA A J, Bell D W. The genomics and genetics of endometrial cancer. Adv Genomics Genet 2012; 2012: 33-47.

OJESINA A I, Lichtenstein L, Freeman S S, Pedamallu C S, Imaz-Rosshandler I, Pugh T J, et al. Landscape of genomic alterations in cervical carcinomas. Nature 2014; 506:371-5.

OTA et al., Single nucleotide polymorphism detection by polymerase chain reaction-restriction fragment length polymorphism. Nat Protoc. 2007; 2 (11): 2857-64.

PARAISO K H T, Fedorenko I V, Cantini L P, Munko A C, Hall M, Sondak V K, et al. Recovery of phospho-ERK activity allows melanoma cells to escape from BRAF inhibitor therapy. Br J Cancer 2010; 102:1724-30.

PATGIRI A, Yadav, K K, Arora, P S, Bar-Sagi, D. An orthosteric inhibitor of the Ras-Sos interaction. Nat Chem Biol. 2011; 7:585-587.

PENNYCUICK A, Simpson T, Crawley D, Lal R, Santis G, Cane P, et al. Routine EGFR and KRAS mutation analysis using COLD-PCR in non-small cell lung cancer. Int J Clin Pract 2012; 66:748-52.

PORTER S B, Hildebrandt E R, Breevoort S R, Mokry D Z, Dore T M, Schmidt W K. Inhibition of the CaaX proteases Rce1p and Ste24p by peptidyl (acyloxy)methyl ketones. Biochim Biophys Acta. 2007; 1773 (6): 853-862.

POULIKAKOS P I, Persaud Y, Janakiraman M, Kong X, Ng C, Moriceau G, et al. RAF inhibitor resistance is mediated by dimerization of aberrantly spliced BRAF (V600E). Nature 2011; 480:387-90.

QUEIROLO P, Picasso V, Spagnolo F. Combined BRAF and MEK inhibition for the treatment of BRAF-mutated metastatic melanoma. Cancer Treat Rev 2015; 41:519-26.

RASOLA A, Sciacovelli M, Chiara F, Pantic B, Brusilow W S, Bernardi P. Activation of mitochondrial ERK protects cancer cells from death through inhibition of the permeability transition. Proc Natl Acad Sci USA 2010; 107:726-31.

RIZOS H, Menzies A M, Pupo G M, Carlino M S, Fung C, Hyman J, et al. BRAF inhibitor resistance mechanisms in metastatic melanoma: spectrum and clinical impact. Clin Cancer Res 2014; 20:1965-77.

ROBERT C, Karaszewska B, Schachter J, Rutkowski P, Mackiewicz A, Stroiakovski D, et al. Improved overall survival in melanoma with combined dabrafenib and trametinib. N Engl J Med 2015; 372:30-9.

ROMEO Y, Zhang X, Roux P P. Regulation and function of the RSK family of protein kinases. Biochem J 2012; 441:553-69.

RUDOLPH J, Xiao Y, Pardi A, Ahn N G. Slow inhibition and conformation selective properties of extracellular signal-regulated kinase 1 and 2 inhibitors. Biochemistry 2015; 54:22-31.

SHAUL Y D, Seger R. The MEK/ERK cascade: from signaling specificity to diverse functions. Biochim Biophys Acta 2007; 1773:1213-26.

SHI H, Hugo W, Kong X, Hong A, Koya R C, Moriceau G, et al. Acquired resistance and clonal evolution in melanoma during BRAF inhibitor therapy. Cancer Discov 2014; 4:80-93.

SHIMA, F, Yoshikawa, Y, Ye, M, Araki, M, Matsumoto, S, Liao, J, Hu, L, Sugimoto, T, Ijiri, Y, Takeda, A, Nishiyama, Y, Sato, C, Muraoka, S, Tamura, A, Osoda, T, Tsuda, K-I, Miyakawa, T, Fukunishi, H, Shimada, J, Kumasaka, Yamamoto, M, Kataoka, T. In silico discovery of small-molecule Ras inhibitors that display antitumor activity by blocking the Ras-effector interaction. PNAS. 2013; 110(20):8182-7.

SCHUBBERT S, Shannon K, Bollag G. Hyperactive Ras in developmental disorders and cancer. Nat Rev Cancer 2007; 7:295-308.

SUN C, Hobor S, Bertotti A, Zecchin D, Huang S, Galimi F, et al. Intrinsic resistance to MEK inhibition in KRAS mutant lung and colon cancer through transcriptional induction of ERBB3. Cell Rep 2014; 7:86-93.

TAFLINAR [package insert]. Research Triangle Park, NC: GlaxoSmithKline; 2015.

TRUNZER K, Pavlick A C, Schuchter L, Gonzalez R, McArthur G A, Hutson T E, et al. Pharmacodynamic effects and mechanisms of resistance to vemurafenib in patients with metastatic melanoma. J Clin Oncol 2013; 31:1767-74.

VILLANUEVA, J., et al. Acquired resistance to BRAF inhibitors mediated by a RAF kinase switch in melanoma can be overcome by cotargeting MEK and IGF-1R/PI3K. Cancer Cell. 2010; 18:683-695.

WAGLE, N., et al. Dissecting therapeutic resistance to RAF inhibition in melanoma by tumor genomic profiling. Journal of Clinical Oncology 2011; 29(22):3085-3096.

WAGLE N, Van Allen E M, Treacy D J, Frederick D T, Cooper Z A, Taylor-Weiner A, et al. MAP kinase pathway alterations in BRAF-mutant melanoma patients with acquired resistance to combined RAF/MEK inhibition. Cancer Discov 2014; 4:61-8.

Wainstein E, Seger R. The dynamic subcellular localization of ERK: mechanisms of translocation and role in various organelles. Curr Opin Cell Biol 2016; 39:15-20.

WANG, H., et al. Identification of the MEK1 (F129L) activating mutation as a potential mechanism of acquired resistance to MEK inhibition in human cancers carrying the B-RAF V600E mutation. Cancer Res (2011); 71(16):5535-45.

YANG W, Soares J, Greninger P, Edelman E J, Lightfoot H, Forbes S, et al. Genomics of Drug Sensitivity in Cancer (GDSC): a resource for therapeutic biomarker discovery in cancer cells. Nucleic Acids Res 2013; 41:D955-D961.

YAO Z, Torres N M, Tao A, Gao Y, Luo L, Li Q, et al. BRAF Mutants Evade ERK-Dependent Feedback by Different Mechanisms that Determine Their Sensitivity to Pharmacologic Inhibition. Cancer Cell 2015; 28:370-83.

YOHE S. Molecular genetic markers in acute myeloid leukemia. J Clin Med 2015; 4:460-78.

ZELBORAF [package insert]. South San Francisco, CA: Genentech USA, Inc.: 2015.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for treating or ameliorating the effects of a cancer in a subject harboring a non-V600E/K BRAF mutation, the method comprising administering to the subject an effective amount of an ERK inhibitor or a pharmaceutically acceptable salt thereof, wherein the non-V600E/K BRAF mutation is selected from the group consisting of L485W, F247L, BRAF-AGAP3 rearrangement, BRAF exon 15 splice variant, and combinations thereof, and wherein the ERK inhibitor is selected from the group consisting of BVD-523, SCH-722984, SCH-772984, SCH-900353, LY3214996, AEZS-140, AEZS-131, AEZS-136, LTT-462, RG-7842, CC-90003, KIN-4050, and combinations thereof.

2. The method according to claim 1, wherein the ERK inhibitor is BVD-523.

3. The method according to claim 1, wherein the subject is a mammal.

4. The method according to claim 3, wherein the mammal is selected from the group consisting of humans, primates, farm animals, and domestic animals.

5. The method according to claim 3, wherein the mammal is a human.

6. The method according to claim 1, wherein the cancer is a solid tumor cancer or a hematologic cancer.

7. The method according to claim 1, wherein the cancer is selected from the group consisting of glioblastoma, melanoma, cholangiocarcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer.

8. The method according to claim 7, wherein the cancer is selected from the group consisting of small intestine cancer, non-small cell lung cancer, gallbladder cancer, and squamous cell cancer.

9. The method according to claim 1 further comprising administering to the subject at least one additional therapeutic agent selected from the group consisting of an MEK inhibitor, a RAF inhibitor, an HDAC inhibitor, and combinations thereof.

10. The method according to claim 9, wherein the MEK inhibitor is selected from the group consisting of anthrax toxin, antroquinonol, binimetinib, AS-1940477, AS-703988, bentamapimod, BI-847325, E-6201, GDC-0623, cobimetinib, L783277, lethal factor portion of anthrax toxin, MEK162, PD 098059 (2-(2'-amino-3'-methoxphenyl)-oxanaphthalen-4-one), PD 184352, PD-0325901, PD318088, PD334581, 6-methoxy-7-(3-morpholin-4-yl-propoxy)-4-(4-phenoxy-phenylamino)-quinoline-3-carbonitrile, 4-[3-chloro-4-(1-methyl-1H-imidazol-2-ylsulfanyl)-phenylamino]-6-methoxy-7-(3-morpholin-4-yl-propoxy)-quinoline-3-carbonitrile, pimasertib, RDEA 119, refametinib, RG422 RO092210, RO4987655, RO5126766, selumetinib, SL327, TAK-733, trametinib, U0126 (1,4-diamino-2, 3-dicyano-1,4-bis(2-aminophenylthio) butadiene), WX-554, YopJ polypeptide, pharmaceutically acceptable salts thereof, and combinations thereof.

11. The method according to claim 9, wherein the RAF inhibitor is selected from the group consisting of AAL881, AB-024, ARQ-736, ARQ-761, AZ628, BeiGene-283, BUB-024, BRAF siRNA 313 (tacaccagcaagctagatgca (SEQ ID NO: 45)), BRAF siRNA 523 (cctatcgttagagtcttcctg (SEQ ID NO: 46)), CHIR-265, CTT239065, dabrafenib, DP-4978, HM-95573, GDC-0879, GW-5074, ISIS 5132, L779450, LBT613, LXH254, LErafAON, LGX-818, pazopanib, PLX3202, PLX4720, PLX5568, PLX3603, PLX8394, RAF-265, RAF-365, REDX0535, regorafenib, RO 5126766, SB-590885, SB699393, sorafenib, TAK 632, TL-241, vemurafenib, XL-281, ZM-336372, pharmaceutically acceptable salts thereof, and combinations thereof.

12. The method according to claim 9, wherein the HDAC inhibitor is selected from the group consisting of Abexinostat, Givinostat, Vorinostat, CI-994, CUDC-101, Entinostat, BML-210, M344, NVP-LAQ824, Panobinostat, Pracinosat, Mocetinostat, Resminostat, Romidepsin, Belinostat, pharmaceutically acceptable salts thereof, and combinations thereof.

13. The method according to claim 9 wherein the RAF inhibitor is selected from the group consisting of erlotinib, gefitinib, imatinib mesylate, lapatinib, sunitinib malate, pharmaceutically acceptable salts thereof, and combinations thereof.

14. The method according to claim 9 wherein the RAF inhibitor is selected from the group consisting of LXH254, PLX3603, PLX8394, REDX0535, pharmaceutically acceptable salts thereof, and combinations thereof.

15. The method according to claim 9 wherein the HDAC inhibitor is selected from the group consisting of Vorinostat, Panobinostat, Romidepsin, Belinostat, pharmaceutically acceptable salts thereof, and combinations thereof.

16. A method for treating or ameliorating the effects of a cancer in a subject comprising the steps of:

(a) identifying a subject with a cancer harboring a non-V600E/K BRAF mutation, wherein the non-V600E/K BRAF mutation is selected from the group consisting of L485W, F247L, BRAF-AGAP3 rearrangement, BRAF exon 15 splice variant, and combinations thereof; and (b) administering to the subject an effective amount of an ERK inhibitor or a pharmaceutically acceptable salt thereof, wherein the ERK inhibitor is selected from the group consisting of BVD-523, SCH-722984, SCH-772984, SCH-900353, LY3214996, AEZS-140, AEZS-131, AEZS-136, LTT-462, RG-7842, CC-90003, KIN-4050, and combinations thereof.

17. The method according to claim 16, wherein the ERK inhibitor is BVD-523.

18. The method according to claim 16, wherein the subject is a mammal.

19. The method according to claim 18, wherein the mammal is selected from the group consisting of humans, primates, farm animals, and domestic animals.

20. The method according to claim 18, wherein the mammal is a human.

21. The method according to claim 16, wherein the cancer is a solid tumor cancer or a hematologic cancer.

22. The method according to claim 16, wherein the cancer is selected from the group consisting of glioblastoma, melanoma, cholangiocarcinoma, small cell lung cancer, colorectal cancer, prostate cancer, vaginal cancer, angiosarcoma, non-small cell lung cancer, appendiceal cancer, squamous cell cancer, salivary duct carcinoma, adenoid cystic carcinoma, small intestine cancer, and gallbladder cancer.

23. The method according to claim 22, wherein the cancer is selected from the group consisting of small intestine cancer, non-small cell lung cancer, gallbladder cancer, and squamous cell cancer.

24. The method according to claim 16, wherein step (a) comprises:

(i) obtaining a biological sample from the subject; and (ii) screening the sample to determine whether the subject has a non-V600E/K BRAF mutation.

25. The method according to claim 16 further comprising administering to the subject at least one additional therapeutic agent selected from the group consisting of an MEK inhibitor, a RAF inhibitor, an HDAC inhibitor, and combinations thereof.

26. The method according to claim 25, wherein the MEK inhibitor is selected from the group consisting of anthrax toxin, antroquinonol, binimetinib, AS-1940477, AS-703988, bentamapimod, BI-847325, E-6201, GDC-0623, cobimetinib, L783277, lethal factor portion of anthrax toxin, MEK162, PD 098059 (2-(2'-amino-3'-methoxphenyl)-oxanaphthalen-4-one), PD 184352, PD-0325901, PD318088, PD334581, 6-methoxy-7-(3-morpholin-4-yl-propoxy)-4-(4-phenoxy-phenylamino)-quinoline-3-carbonitrile, 4-[3-chloro-4-(1-methyl-1H-imidazol-2-ylsulfanyl)-phenylamino]-6-methoxy-7-(3-morpholin-4-yl-propoxy)-quinoline-3-carbonitrile, pimasertib, RDEA 119, refametinib, RG422, RO092210, RO4987655, RO5126766, selumetinib, SL327, TAK-733, trametinib, U0126 (1,4-diamino-2, 3-dicyano-1,4-bis(2-aminophenylthio) butadiene), WX-554, YopJ polypeptide, pharmaceutically acceptable salts thereof, and combinations thereof.

27. The method according to claim 25, wherein the RAF inhibitor is selected from the group consisting of AAL881, AB-024, ARQ-736, ARQ-761, AZ628, BeiGene-283, BUB-024, BRAF siRNA 313 (tacaccagcaagctagatgca (SEQ ID NO: 45)), BRAF siRNA 523 (cctatcgttagagtcttcctg (SEQ ID NO: 46)), CHIR-265, CTT239065, dabrafenib, DP-4978, HM-95573, GDC-0879, GW-5074, ISIS 5132, L779450, LBT613, LXH254, LErafAON, LGX-818, pazopanib, PLX3202, PLX4720, PLX5568, PLX3603, PLX8394, RAF-265, RAF-365, REDX0535, regorafenib, RO 5126766, SB-590885, SB699393, sorafenib, TAK 632, TL-241, vemurafenib, XL-281, ZM-336372, pharmaceutically acceptable salts thereof, and combinations thereof.

28. The method according to claim 25, wherein the HDAC inhibitor is selected from the group consisting of Abexinostat, Givinostat, Vorinostat, CI-994, CUDC-101, Entinostat, BML-210, M344, NVP-LAQ824, Panobinostat, Pracinosat, Mocetinostat, Resminostat, Romidepsin, Belinostat, pharmaceutically acceptable salts thereof, and combinations thereof.

29. A method for treating or ameliorating the effects of a cancer in a subject harboring a non-V600E/K BRAF mutation, the method comprising administering to the subject an effective amount of BVD-523 or a pharmaceutically acceptable salt thereof, wherein the non-V600E/K BRAF mutation is selected from the group consisting of L485W, F247L, BRAF-AGAP3 rearrangement, BRAF exon 15 splice variant, and combinations thereof.

30. A method for treating or ameliorating the effects of a cancer in a subject comprising:

(a) identifying a subject with a cancer harboring a non-V600E/K BRAF mutation, wherein the non-V600E/K BRAF mutation is selected from the group consisting of L485W, F247L, BRAF-AGAP3 rearrangement, BRAF exon 15 splice variant, and combinations thereof; and (b) administering to the subject an effective amount of BVD-523 or a pharmaceutically acceptable salt thereof.

* * * * *

SEQUENCE LISTING

```
<160> NUMBER OF SEQ ID NOS: 44

<210> SEQ ID NO 1
<211> LENGTH: 2949
<212> TYPE: DNA
<213> ORGANISM: Homo sapiens

<400> SEQUENCE: 1

cgcctccctt ccccctcccc gcccgacagc ggccgctcgg gccccggctc tcggttataa     60

gatggcggcg ctgagcggtg gcggtggtgg cggcgcggag ccgggccagg ctctgttcaa    120

cggggacatg gagcccgagg ccggcgccgg cgccggcgcc gcggcctctt cggctgcgga    180

ccctgccatt ccggaggagg tgtggaatat caaacaaatg attaagttga cacaggaaca    240

tatagaggcc ctattggaca aatttggtgg ggagcataat ccaccatcaa tatatctgga    300

ggcctatgaa gaatacacca gcaagctaga tgcactccaa caaagagaac aacagttatt    360

ggaatctctg gggaacggaa ctgatttttc tgtttctagc tctgcatcaa tggataccgt    420

tacatcttct tcctcttcta gcctttcagt gctaccttca tctctttcag tttttcaaaa    480

tcccacagat gtggcacgga gcaaccccaa gtcaccacaa aaacctatcg ttagagtctt    540

cctgcccaac aaacagagga cagtggtacc tgcaaggtgt ggagttacag tccgagacag    600

tctaaagaaa gcactgatga tgagaggtct aatcccagag tgctgtgctg tttacagaat    660

tcaggatgga gagaagaaac caattggttg ggacactgat atttcctggc ttactggaga    720

agaattgcat gtggaagtgt tggagaatgt tccacttaca acacacaact ttgtacgaaa    780

aacgtttttc accttagcat tttgtgactt ttgtcgaaag ctgcttttcc agggtttccg    840

ctgtcaaaca tgtggttata aatttcacca gcgttgtagt acagaagttc cactgatgtg    900

tgttaattat gaccaacttg atttgctgtt tgtctccaag ttctttgaac accacccaat    960

accacaggaa gaggcgtcct tagcagagac tgccctaaca tctggatcat ccccttccgc   1020

acccgcctcg gactctattg ggccccaaat tctcaccagt ccgtctcctt caaaatccat   1080
```

tccaattcca cagcccttcc gaccagcaga tgaagatcat cgaaatcaat ttgggcaacg 1140
agaccgatcc tcatcagctc ccaatgtgca tataaacaca atagaacctg tcaatattga 1200
tgacttgatt agagaccaag gatttcgtgg tgatggagga tcaaccacag gtttgtctgc 1260 tacccccccct gcctcattac ctggctcact aactaacgtg aaagccttac agaaatctcc 1320
aggacctcag cgagaaagga agtcatcttc atcctcagaa gacaggaatc gaatgaaaac 1380
acttggtaga cgggactcga gtgatgattg ggagattcct gatgggcaga ttacagtggg 1440
acaaagaatt ggatctggat catttggaac agtctacaag ggaaagtggc atggtgatgt 1500
ggcagtgaaa atgttgaatg tgacagcacc tacacctcag cagttacaag ccttcaaaaa 1560
tgaagtagga gtactcagga aaacacgaca tgtgaatatc ctactcttca tgggctattc 1620
cacaaagcca caactggcta ttgttaccca gtggtgtgag ggctccagct tgtatcacca 1680
tctccatatc attgagacca aatttgagat gatcaaactt atagatattg cacgacagac 1740
tgcacagggc atggattact tacacgccaa gtcaatcatc cacagagacc tcaagagtaa 1800
taatatattt cttcatgaag acctcacagt aaaaataggt gattttggtc tagctacagt 1860
gaaatctcga tggagtgggt cccatcagtt tgaacagttg tctggatcca ttttgtggat 1920
ggcaccagaa gtcatcagaa tgcaagataa aaatccatac agctttcagt cagatgtata 1980
tgcatttgga attgttctgt atgaattgat gactggacag ttaccttatt caaacatcaa 2040
caacagggac cagataattt ttatggtggg acgaggatac ctgtctccag atctcagtaa 2100
ggtacggagt aactgtccaa aagccatgaa gagattaatg gcagagtgcc tcaaaaagaa 2160
aagagatgag agaccactct ttccccaaat tctcgcctct attgagctgc tggcccgctc 2220
attgccaaaa attcaccgca gtgcatcaga accctccttg aatcgggctg gtttccaaac 2280
agaggatttt agtctatatg cttgtgcttc tccaaaaaca cccatccagg caggggggata 2340 tggtgcgttt cctgtccact gaaacaaatg agtgagagag ttcaggagag tagcaacaaa 2400
aggaaaataa atgaacatat gtttgcttat atgttaaatt gaataaaata ctctcttttt 2460
ttttaaggtg aaccaaagaa cacttgtgtg gttaaagact agatataatt tttccccaaa 2520
ctaaaattta tacttaacat tggattttta acatccaagg gttaaaatac atagacattg 2580
ctaaaaattg gcagagcctc ttctagaggc tttactttct gttccgggtt tgtatcattc 2640
acttggttat tttaagtagt aaacttcagt ttctcatgca acttttgttg ccagctatca 2700
catgtccact agggactcca gaagaagacc ctacctatgc ctgtgtttgc aggtgagaag 2760
ttggcagtcg gttagcctgg gttagataag gcaaactgaa cagatctaat ttaggaagtc 2820
agtagaattt aataattcta ttattattct taataatttt tctataacta tttcttttta 2880
taacaatttg gaaaatgtgg atgtctttta tttccttgaa gcaataaact aagtttcttt 2940
ttataaaaa 2949

<210> SEQ ID NO 2
<211> LENGTH: 766
<212> TYPE: PRT
<213> ORGANISM: Homo sapiens

<400> SEQUENCE: 2

Met Ala Ala Leu Ser Gly Gly Gly Gly Gly Gly Ala Glu Pro Gly Gln
1 5 10 15

Ala Leu Phe Asn Gly Asp Met Glu Pro Glu Ala Gly Ala Gly Ala Gly
20 25 30

Ala Ala Ala Ser Ser Ala Ala Asp Pro Ala Ile Pro Glu Glu Val Trp

-continued

```
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460
```

Ser Gly Ser Phe Gly Thr Val Tyr Lys Gly Lys Trp His Gly Asp Val
465 470 475 480

Ala Val Lys Met Leu Asn Val Thr Ala Pro Thr Pro Gln Gln Leu Gln
485 490 495

Ala Phe Lys Asn Glu Val Gly Val Leu Arg Lys Thr Arg His Val Asn
500 505 510

Ile Leu Leu Phe Met Gly Tyr Ser Thr Lys Pro Gln Leu Ala Ile Val
515 520 525

Thr Gln Trp Cys Glu Gly Ser Ser Leu Tyr His His Leu His Ile Ile
530 535 540

Glu Thr Lys Phe Glu Met Ile Lys Leu Ile Asp Ile Ala Arg Gln Thr
545 550 555 560

Ala Gln Gly Met Asp Tyr Leu His Ala Lys Ser Ile Ile His Arg Asp
565 570 575

Leu Lys Ser Asn Asn Ile Phe Leu His Glu Asp Leu Thr Val Lys Ile
580 585 590

Gly Asp Phe Gly Leu Ala Thr Val Lys Ser Arg Trp Ser Gly Ser His
595 600 605

Gln Phe Glu Gln Leu Ser Gly Ser Ile Leu Trp Met Ala Pro Glu Val
610 615 620

Ile Arg Met Gln Asp Lys Asn Pro Tyr Ser Phe Gln Ser Asp Val Tyr
625 630 635 640

Ala Phe Gly Ile Val Leu Tyr Glu Leu Met Thr Gly Gln Leu Pro Tyr
645 650 655

Ser Asn Ile Asn Asn Arg Asp Gln Ile Ile Phe Met Val Gly Arg Gly
660 665 670

Tyr Leu Ser Pro Asp Leu Ser Lys Val Arg Ser Asn Cys Pro Lys Ala
675 680 685

Met Lys Arg Leu Met Ala Glu Cys Leu Lys Lys Lys Arg Asp Glu Arg
690 695 700

Pro Leu Phe Pro Gln Ile Leu Ala Ser Ile Glu Leu Leu Ala Arg Ser
705 710 715 720

Leu Pro Lys Ile His Arg Ser Ala Ser Glu Pro Ser Leu Asn Arg Ala
725 730 735

Gly Phe Gln Thr Glu Asp Phe Ser Leu Tyr Ala Cys Ala Ser Pro Lys
740 745 750

Thr Pro Ile Gln Ala Gly Gly Tyr Gly Ala Phe Pro Val His
755 760 765

<210> SEQ ID NO 3
<211> LENGTH: 3906
<212> TYPE: DNA
<213> ORGANISM: Rattus norvegicus

<400> SEQUENCE: 3
atggcggcgc tgagtggcgg cggtggcagc agcagcggtg gcggtggcgg cggcggcggc 60
ggcggtggtg gcggcggcgg cggcggcgcc gaacagggac aggctctgtt caatggcgac 120
atggagccgg aggccggcgc tggcgccgcg gcctcttcgg ccgcggaccc ggccattcct 180
gaagaggtgt ggaatatcaa gcaaatgatt aagttgacac aggaacatat agaggcccta 240
ttggacaagt ttggtgggga gcataaccca ccgtcaatat acctggaggc ctatgaagag 300
tacaccagca agctagatgc ccttcagcag agagagcagc agctgttgga atccctggtt 360
tttcaaactc ccacagatgt atcacggaac aaccccaagt caccacagaa acctatcgtt 420
cgtgtcttcc tgcccaacaa acagaggaca gtggtgcccg caagatgtgg tgtaacggtc 480
cgagacagtc taaagaaagc actaatgatg aggggtctca tcccagagtg ctgtgctgtt 540
tacagaattc aggacggaga gaagaaacca attggctggg acactgacat ttcctggctt 600
actggagagg agctacatgt tgaagtacta gagaatgttc ctctgacaac ccacaacttc 660
gtacggaaaa cttttttcac cttagcattt tgtgactttt gccgaaagct gcttttccag 720
ggtttccgct gtcaaacatg tggttataag tttcaccagc gttgtagtac agaggttcca 780
ctgatgtgtg ttaattatga ccaacttgat ttgctgtttg tctccaagtt ctttgagcat 840
cacccagtac cacaggagga ggccttctca gcagagacta cccttccatc tggatgctct 900
tccgcacccc cctcagactc tattgggccc caaatcctca ccagtccatc tccttcaaaa 960
tccattccaa ttccacagcc cttccggcca gcagatgaag atcatcgcaa tcagtttggg 1020
caacgagacc gctcctcctc cgctcccaat gttcatataa acacaatcga acctgtcaat 1080
attgatgaaa aattcccaga agtggaatta caggatcaaa gggatttgat tagagaccag 1140
gggtttcgtg gggatggagc ccctttgaac cagctgatgc gctgtcttcg gaaataccaa 1200
tcccggactc ccagcccccct cctccattct gtccccagtg aaatagtgtt tgattttgag 1260
cctggcccag tgttcagagg gtcaaccaca ggcttgtcgg ccacccccacc tgcctcatta 1320
cctggctcac tcactaacgt gaaagcctta cagaaatctc caggacctca gcgggaaagg 1380
aagtcctcct cctcctcctc ctccacggaa gacagaagtc ggatgaaaac acttggtaga 1440
agagattcaa gtgatgattg ggagattcct gatggacaga ttacagtggg acagagaatt 1500
ggatctgggt cctttggaac tgtctacaag ggaaagtggc atggcgacgt ggcagtgaaa 1560
atgctgaatg tgacagcacc cacacctcag cagttacagg ccttcaaaaa cgaagtcgga 1620
gtactcagga aaactcgaca tgtgaacatc ctcctttca tgggctattc tacaaagcca 1680
cagctggcta ttgttacaca gtggtgtgaa ggctccagct tatatcacca tctccacatc 1740
attgagacca aatttgagat gatcaaactt atagatattg cacggcagac tgcacagggc 1800
atggattact tacacgccaa gtcaatcatc cacagagacc tcaagagtaa taatatattt 1860
cttcatgaag acctcacggt aaaaataggt gactttggtt tagccacagt gaagtcccga 1920
tggagtgggt cccatcagtt tgaacagttg tctggatcta ttttgtggat ggcacccgaa 1980
gtaatcagaa tgcaagataa aaacccatat agctttcagt cagacgtgta tgcatttggg 2040
attgttctgt atgaactgat gactggtcag ctaccttatt caaacatcaa caacagggat 2100
cagataattt ttatggtggg acgaggatac ctatctccag atctcagtaa ggtacggagt 2160
aactgtccaa aagccatgaa gagattaatg gcagagtgcc tcaaaaagaa aagagacgag 2220
agaccactct ttccccaaat tctcgcctct attgagctgc tggcccgctc attgccaaaa 2280
attcaccgca gtgcatcaga accctccttg aatcgggctg gtttccaaac agaagatttt 2340
agtctgtatg cttgtgcttc tccaaaaaca cccatccaag caggggggata tggagaattt 2400
gcagccttca agtagccact ccatcatggc agcatctact ctttatttct taagtcttgt 2460
gttcatacaa tttgttaaca tcaaaacaca gttctgttcc tcaaattttt tttaaagata 2520
caaaatttc aatgcataag ctcgtgtgga acagaatgga atttcctatt caacaaaaga 2580
gggaagaatg ttttaggaac cagaattctc tgctgcccgt gtttcttctt caacacaaat 2640
atcatgtgca tacaactctg cccattccca agaagaaaga ggagagaccc cgaattctgc 2700
ccttttggtg gtcaggcatg atggaaagaa tttgctgctg cagcttggga aaaattgcta 2760

-continued

```
tggaaagtct gccagtcaac tttgcccttc taaccaccag atccatttgt ggctggtcat   2820

ctgatggggc gatttcaatc accaagcatc gttcttgcct gttgtgggat tatgtcgtgg   2880

agcactttcc ctatccacca ccgttaattt ccgagggatg gagtaaatgc agcataccct   2940

ttgtgtagca cctgtccagt cctcaaccaa tgctatcaca gtgaagctct ttaaatttaa   3000

gtggtgggtg agtgttgagg agagactgcc ttgggggcag agaaaagggg atgctgcatc   3060

ttcttcctca cctccagctc tctcacctcg ggttgccttg cacactgggc tccgcctaac   3120

cactcgggct gggcagtgct ggcacacatt gccgcctttt ctcattgggt ccagcaattg   3180

agcagagggt tgggggattg tttcctccac aatgtagcaa attctcagga aaatacagtc   3240

catatcttcc tctcagctct tccagtcacc aaatacttac gtggctcctt tgtccaggac   3300

ataaaacacc gtggacaaca cctaattaaa agcctacaaa actgcttact gacagttttg   3360

aatgtgagac atttgtgtaa tttaaatgta aggtacaggt cttaatttct tctattaagt   3420

ttcttctatt tttatttaaa cgaagaaaat aattttcagg tttaattgga ataaacgaat   3480

acttcccaaa agactatata ccctgaaaat tatatttttg ttaattgtaa acaactttta   3540

aaaaatggtt attatccttt tctctaccta aaattatggg aaatcttagc ataatgacaa   3600

ttatttatac tttttaaata aatggtactt gctggatcca cactaacatc tttgctaaca   3660

ttcccattgt ttcttccaac ttcactccta cactacatcc tccatcctct ttctagtctt   3720

ttatctataa tatgcaacct aaaataaaag tggtggtgtc tccattcatt cttcttcttc   3780

ctttttttccc caagcctggt cttcaaaagg ttgggtaatt tagtagctga gttccctagg   3840

tagaaataga actattaggg acattggggt tgtaggaaag cgtgaggcct gtcaccagtt   3900

gttctt                                                               3906
```

```
<210> SEQ ID NO 4
<211> LENGTH: 804
<212> TYPE: PRT
<213> ORGANISM: Rattus norvegicus

<400> SEQUENCE: 4

Met Ala Ala Leu Ser Gly Gly Gly Gly Ser Ser Ser Gly Gly Gly Gly
1               5                   10                  15

Gly Gly Gly Gly Gly Gly Gly Gly Gly Gly Gly Gly Gly Ala Glu Gln
            20                  25                  30

Gly Gln Ala Leu Phe Asn Gly Asp Met Glu Pro Glu Ala Gly Ala Gly
        35                  40                  45

Ala Ala Ala Ser Ser Ala Ala Asp Pro Ala Ile Pro Glu Glu Val Trp
    50                  55                  60

Asn Ile Lys Gln Met Ile Lys Leu Thr Gln Glu His Ile Glu Ala Leu
65                  70                  75                  80

Leu Asp Lys Phe Gly Gly Glu His Asn Pro Pro Ser Ile Tyr Leu Glu
                85                  90                  95

Ala Tyr Glu Glu Tyr Thr Ser Lys Leu Asp Ala Leu Gln Gln Arg Glu
            100                 105                 110

Gln Gln Leu Leu Glu Ser Leu Val Phe Gln Thr Pro Thr Asp Val Ser
        115                 120                 125

Arg Asn Asn Pro Lys Ser Pro Gln Lys Pro Ile Val Arg Val Phe Leu
    130                 135                 140

Pro Asn Lys Gln Arg Thr Val Val Pro Ala Arg Cys Gly Val Thr Val
145                 150                 155                 160

Arg Asp Ser Leu Lys Lys Ala Leu Met Met Arg Gly Leu Ile Pro Glu
```

-continued

```
                165                 170                 175

Cys Cys Ala Val Tyr Arg Ile Gln Asp Gly Glu Lys Lys Pro Ile Gly
            180                 185                 190

Trp Asp Thr Asp Ile Ser Trp Leu Thr Gly Glu Glu Leu His Val Glu
        195                 200                 205

Val Leu Glu Asn Val Pro Leu Thr Thr His Asn Phe Val Arg Lys Thr
    210                 215                 220

Phe Phe Thr Leu Ala Phe Cys Asp Phe Cys Arg Lys Leu Leu Phe Gln
225                 230                 235                 240

Gly Phe Arg Cys Gln Thr Cys Gly Tyr Lys Phe His Gln Arg Cys Ser
            245                 250                 255

Thr Glu Val Pro Leu Met Cys Val Asn Tyr Asp Gln Leu Asp Leu Leu
            260                 265                 270

Phe Val Ser Lys Phe Phe Glu His His Pro Val Pro Gln Glu Glu Ala
        275                 280                 285

Phe Ser Ala Glu Thr Thr Leu Pro Ser Gly Cys Ser Ser Ala Pro Pro
    290                 295                 300

Ser Asp Ser Ile Gly Pro Gln Ile Leu Thr Ser Pro Ser Pro Ser Lys
305                 310                 315                 320

Ser Ile Pro Ile Pro Gln Pro Phe Arg Pro Ala Asp Glu Asp His Arg
                325                 330                 335

Asn Gln Phe Gly Gln Arg Asp Arg Ser Ser Ser Ala Pro Asn Val His
            340                 345                 350

Ile Asn Thr Ile Glu Pro Val Asn Ile Asp Glu Lys Phe Pro Glu Val
        355                 360                 365

Glu Leu Gln Asp Gln Arg Asp Leu Ile Arg Asp Gln Gly Phe Arg Gly
    370                 375                 380

Asp Gly Ala Pro Leu Asn Gln Leu Met Arg Cys Leu Arg Lys Tyr Gln
385                 390                 395                 400

Ser Arg Thr Pro Ser Pro Leu Leu His Ser Val Pro Ser Glu Ile Val
                405                 410                 415

Phe Asp Phe Glu Pro Gly Pro Val Phe Arg Gly Ser Thr Thr Gly Leu
            420                 425                 430

Ser Ala Thr Pro Pro Ala Ser Leu Pro Gly Ser Leu Thr Asn Val Lys
        435                 440                 445

Ala Leu Gln Lys Ser Pro Gly Pro Gln Arg Glu Arg Lys Ser Ser Ser
    450                 455                 460

Ser Ser Ser Ser Thr Glu Asp Arg Ser Arg Met Lys Thr Leu Gly Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590
```

-continued

```
Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys


<210> SEQ ID NO 5
<211> LENGTH: 9728
<212> TYPE: DNA
<213> ORGANISM: Mus musculus

<400> SEQUENCE: 5

ccctcaggct cggctgcgcc ggggccgccg gcgggttcca gaggtggcct ccgccccggc      60

cgctccgccc acgccccccg cgcctccgcg cccgcctccg cccgccctgc gcctcccttc     120

cccctccccg ccccgcggcg gccgctcggc ccggctcgcg cttcgaagat ggcggcgctg     180

agtggcggcg gtggcagcag cagcggtggc ggcggcggcg gtggcggcgg cggtggcggt     240

ggcgacggcg gcggcggcgc cgagcagggc caggctctgt tcaatggcga catggagccg     300

gaggccggcg ctggcgccgc ggcctcttcg gctgcggacc cggccattcc tgaagaggta     360

tggaatatca agcaaatgat taagttgaca caggaacata tagaggccct attggacaaa     420

tttggtggag agcataaccc accatcaata tacctggagg cctatgaaga gtacaccagc     480

aagctagatg cccttcagca aagagaacag cagcttttgg aatccctggt ttttcaaact     540

cccacagatg catcacggaa caaccccaag tcaccacaga aacctatcgt tagagtcttc     600

ctgcccaaca aacagaggac agtggtaccc gcaagatgtg gtgttacagt tcgagacagt     660

ctaaagaaag cactgatgat gagaggtctc atcccagaat gctgtgctgt ttacagaatt     720

caggatggag agaagaaacc aattggctgg gacacggaca tttcctggct tactggagag     780

gagttacatg ttgaagtact ggagaatgtc ccacttacaa cacacaactt tgtacggaaa     840

actttttca ccttagcatt ttgtgacttt tgccgaaagc tgcttttcca gggtttccgt      900
```

-continued

```
tgtcaaacat gtggttataa atttcaccag cgttgtagta cagaggttcc actgatgtgt    960
gtaaattatg accaacttga tttgctgttt gtctccaagt tctttgagca tcacccagta   1020
ccacaggagg aggcctcctt cccagagact gcccttccat ctggatcctc ttccgcaccc   1080
ccctcagact ctactgggcc ccaaatcctc accagtccat ctccttcaaa atccattcca   1140
attccacagc ccttccgacc agcagatgaa gatcatcgca atcagtttgg gcaacgagac   1200
cggtcctcct cagctcccaa tgttcatata aacacaattg agcctgtgaa tatcgatgaa   1260
aaattcccag aagtggaatt acaggatcaa agggatttga ttagagacca ggggtttcgt   1320
ggtgatggag ccccccttgaa ccaactgatg cgctgtcttc ggaaatacca atcccggact   1380
cccagccccc tcctccattc tgtccccagt gaaatagtgt ttgattttga gcctggccca   1440
gtgttcagag ggtcaaccac aggcttgtcc gccaccccgc ctgcctcatt acctggctca   1500
ctcactaacg tgaaagcctt acagaaatct ccaggtcctc agcgggaaag gaagtcatct   1560
tcttcctcat cctcggagga cagaagtcgg atgaaaacac ttggtagaag agattcaagt   1620
gatgactggg agattcctga tggacagatt acagtgggac agagaattgg atctgggtca   1680
tttggaactg tctacaaggg aaagtggcat ggtgatgtgg cagtgaaaat gttgaatgtg   1740
acagcaccca cacctcaaca gctacaggcc ttcaaaaatg aagtaggagt gctcaggaaa   1800
actcgacatg tgaatatcct ccttttcatg ggctattcta caaagccaca actggcaatt   1860
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatatttct tcatgaagac   2040
ctcacggtaa aaataggtga ctttggtcta gccacagtga aatctcggtg gagtgggtcc   2100
catcagtttg aacagttgtc tggatctatt ttgtggatgg caccagaagt aatcagaatg   2160
caagataaaa acccgtatag ctttcagtca gacgtgtatg cgtttgggat tgttctgtac   2220
gaactgatga ccggccagct accttattca aacatcaaca acagggatca gataattttt   2280
atggtgggac gaggatacct atctccagat ctcagtaagg tacggagtaa ctgtccaaaa   2340
gccatgaaga gattaatggc agagtgcctc aaaaagaaaa gagacgagag accactcttt   2400
ccccaaattc tcgcctccat tgagctgctg gcccgctcat tgccaaaaat tcaccgcagt   2460
gcatcagaac cttccttgaa tcgggctggt ttccaaacag aagattttag tctgtatgct   2520
tgtgcttctc cgaaaacacc catccaagca gggggatatg gagaatttgc agccttcaag   2580
tagccagtcc atcatggcag catctactct ttatttctta agtcttgtgt tcatacagtt   2640
tgttaacatc aaaacacagt tctgttcctc aaaaaatttt ttaaagatac aaaattttca   2700
atgcataagt tcatgtggaa cagaatggaa tttcctattc aacaaaagag ggaagaatgt   2760
tttaggaacc agaattctct gctgcccgtg tttcttcttc aacataacta tcacgtgcat   2820
acaagtctgc ccattcccaa gaagaaagag gagagaccct gaattctgcc cttttggtgg   2880
tcaggcatga tggaaagaat ttgctgctgc agcttgggaa aattgctatg gaaagtctgc   2940
cagtcgactt tgcccttcta accaccagat cagcctgtgg ctggtcatct gatggggcga   3000
tttccatcac caagcatcgt tcttgcctat tctgggatta tgttgtggag cactttccct   3060
gtccagcacc gttcatttct gagggatgga gtaaatgcag cattcccttg tgtagcgcct   3120
gttcagtcct cagcagctgc tgtcacagcg aagcttttta cagttaagtg gtgggggaga   3180
gttgaggaga gcctgcctcg gggcagagaa aagggggtgc tgcatcttct tcctcacctc   3240
```

-continued

```
cagctctctc acctcgggtt gccttgctca ctgggctccg cctaaccact caggctgctc   3300
agtgctggca cacattgcct tcttttctca ttgggtccag caattgagga gagggttggg   3360
ggattgtttc ctcctcaatg tagcaaattc tcaggaaaat acagtccata tcttcctctc   3420
agctcttcca gtcaccaaat acttacgtgg ctcctttgtc caggacataa aacaccgtgg   3480
acaacaccta attaaaagcc tacaaaactg cttactgaca gttttgaatg tgagacactt   3540
gtgtaattta aatgtaaggt acaggtttta atttctgagt ttcttctatt tttatttaaa   3600
agaagaaaat aattttcagt tttaattgga ataaatgagt acttcccaca agactatata   3660
ccctgaaaat tatatttttg ttaattgtaa acaactttta aagaataatt attatccttt   3720
tctctaccta aaaattatgg ggaatcttag cataatgaca attatttata ctttttaaat   3780
aaatggtact tgctggatcc acactaacat ctttgctaac aatcccattg tttcttccaa   3840
cttaactcct acactacatc ctacatcctc tttctagtct tttatctata atatgcaacc   3900
taaaataaac gtggtggcgt ctccattcat tctccctctt cctgttttcc ccaagcctgg   3960
tcttcaaaag gttgggtaat cggtccctga gctccctagc tggcaatgca actattaggg   4020
acattggagt tgcaggagag caggaagcct gtccccagct gttcttctag aaccctaaat   4080
cttatctttg cacagatcaa aagtatcacc tcgtcacagt tctccttagc ctttacttac   4140
aggtaatata aataaaaatc accatagtag taaagaaaac aactggatgg attgatgacc   4200
agtacctctc agagccagga atcttgaatc tccaggattt atacgtgcaa atttaaggag   4260
atgtacttag caacttcaag ccaagaactt ccaaaatact agcgaatcta aaataaaatg   4320
gaattttgag ttatttttaa agttcaaatt ataattgata ccactatgta tttaagccta   4380
ctcacagcaa gttagatgga ttttgctaaa ctcattgcca gactgtggtg gtggtggtgg   4440
tagtgtgcac ctttaatcca agcaactcag caatcagaat gaggtaaatc tctgtgaata   4500
caaggcctgc ctagtctgca gcgctagttc caggatagcc agggctacac acacaaaaac   4560
cctctctcaa aaaaaacaaa attaattagt tgataataaa aaataactaa agtatcatca   4620
aaggaaggcc tactggaagt tttatatatt cccagtaaat tgaaaaatat tctgaagtta   4680
ttaaccagtt agcaacaatg tgtttttaag tcttacataa acagagcaaa gtcttcaaat   4740
gtttcagagc tgagaagata attgtgcttg atatgaaaaa tagcctctcc atatgatgtg   4800
ccacattgaa aggcgtcatt acccttttaa atacttctta atgtggcttt gttcccttta   4860
cccaggatta gctagaaaga gctaggtagg cttcggccac agttgcacat ttcgggcctg   4920
ctgaagaatg ggagctttga aggctggcct tggtggagga gcccctcagt gctggagggt   4980
ggggcgtgta cgcagcatgg aagtggtcta gacagagtgc aaagggacag acttctttct   5040
cattttagta tagggtgatg tctcacttga aatgagaaag tagagttgat attaaacgaa   5100
gctgtgccca gaaaccaggc tcagggtatt gtgagatttt ctttttaaat agagaatata   5160
aaagatagaa ataaatattt aaaccttcct tcttattttc tatcaaatag atttttttta   5220
tcatttgcaa acaacataaa aaaaggtttc ttttgtgggg ttttctttcc ttcttttttt   5280
tttttttttt tttttaagac tgcagataat cttgttgagc tcctcggaaa atacaaggaa   5340
gtccgtgttt gtgcagagcg ctttatgagt aactgtatag acagtgtggc tgcttcactc   5400
atcccagagg gctgcagctg tcggcccatg aagtggctgc agtgcctcgt gagatctgct   5460
ttgttttgtt tggagtgaag tctttgaaag gtttgagtgc aactatatag gactgttttt   5520
aaataagtag tattcctcat gaactttctc attgttaagc tacaggaccc aaactctacc   5580
actaagatat tattaacctc aaaatgtagt ttatagaagg aatttgcaaa tagaatatcc   5640
```

agttcgtact tatatgcatc ttcaacaaag attctctgtg acttgttgga tttggttcct 5700
gaacagccca tttctgtatt tgaggttagg agggcataat gaggcatcct aaaagacaat 5760
ctgatataaa ctgtatgcta gatgtatgct ggtaggggag aaagcattct gtaaagacat 5820
gatttaagac ttcagctctg tcaaccagaa accttgtaaa tacttcctgt cttggtgcag 5880
ccccgcccct ttgatcacac gatgttgtct tgtgcttgtc agacactgtc agagctgctg 5940
ttcgtccctc tgcagatctc acctgtcccc actgcacacc cacctcctgc ctcttgcaga 6000
cctcagcatc tagctttagt tggaaacagt tcagggttca ggtgacttct taaaaaaaaa 6060
aaaaaaccct acctcctcag aatgaggtaa tgaatagtta tttatttaaa gtatgaagag 6120
tcaggagcgc tcgaacatga aggtgattta agatggttcc tttcgtgtgt attgtagctg 6180
agcacttgtt tttgtcctaa agggcattat acatttaagc agtgattctg tttaaagatg 6240
tttttcttta aaggtgtagc tcagagtatc tgttgttgga attggtgcca gagtctgctt 6300
aatagatttc agaatcctaa gcttaagtca gtcgcatgaa gttaagtagt tatggtaaca 6360
ctttgctagc catgatataa ttctactttt taggagtagg tttggcaaaa ctgtatgcct 6420
tcaaagtgag ttggccacag ctttgtcaca tgcacagata ctcatctgaa gagactgccc 6480
agctaagagg gcggaaggat accctttttt cctacgattc gcttctttgt ccacgttggc 6540
attgttagta ctagtttatc agcaccttga ccagcagatg tcaaccaata agctattttt 6600
aaaaccatag ccagagatgg agaggtcact gtgagtagaa acagcaggac gcttacagga 6660
gtgaaatggt gtagggaggc tctagaaaaa tatcttgaca atttgccaaa tgatcttact 6720
gtgccttcat gatgcaataa aaaagctaac attttagcag aaatcagtga tttacgaaga 6780
gagtggccag tctggtttaa ctcagctggg ataatatttt tagagtgcaa tttagactgc 6840
gaagataaat gcactaaaga gtttatagcc aattcacatt tgaaaaataa gaaaatggta 6900
aattttcagt gaaatatttt tttaaagcac ataatcccta gtgtagccag aaatatttac 6960
cacatagagc agctaggctg agatacagtc cagtgacatt tctagagaaa ccttttctac 7020
tcccacgggc tcctcaaagc atggaaattt tatacaaaat gtttgacatt ttaagatact 7080
gctgtagttt agttttgaaa tagtatgtgc tgagcagcaa tcatgtacta actcagagag 7140
agaaaacaac aacaaattgt gcatctgatt tgttttcaga gaaatgctgc caacttagat 7200
actgagttct cagagcttca agtgtaaact tgcctcccaa gtcctgtttg caaatgaagt 7260
tggctagtgc tactgactgc tccagcacat gatggaaggc agggggctgt ctctgaagtg 7320
tcttctataa agggacaata gaatagtgag agacctggtc agtgtgtgtc agctggacac 7380
tccatgctat gggacttgca tcttctgtcc tcaccatccc caagacattg tgctttcctc 7440
agttgtcctc tagctgtttc actcagacac caagatgaat tactgatgcc agaaggggcc 7500
aaaatggcca gtgtgttttg ggggttgtat cagttgactg gacaataact ttaatagttt 7560
cagatcattt atttttactt ccattttgac agacatttaa atggaaattt agtcctaact 7620
tttgtcattt gaaaggaaaa attaacagtt cctataagat acttttgagg tggaatctga 7680
catcctaatt ttttttcttt tcagtgggtt tgcagcgagg gtcttgtatg cactaggcaa 7740
gggttctacc actaagccac atttcccagg aaataaaatg ttaacagtta aaacatacac 7800
acaaatacac aaacacctta ttaccacttt agtaaagtga gagatgtgcg tcctttgtct 7860
cagtctccac gatttcagct gccccttgta tgaataactc agtctcgcta aactgtttac 7920
ttttatttac ctggtttgac tagttgcagc tatataacca gttgtgcatg aggacaacag 7980

-continued

```
ccagtgtgtt tgttttgttt ttggtttttt gtggtacatt ttttgtaaag aattctgtag   8040

attgaagtgc tctttgaaaa cagaactgag atatatttat tcttgttagc atcaaaaaac   8100

attttgtgca aatgatttgc ttttcctggc aggctgagta ccatatccag cgcccacaat   8160

tgcgggttcc catctaccat gtccacaggg gagacagacg ggaagcacat gaggggtgtg   8220

tttacagagt tgtaggagtt atgtagttct cttgttgcct tggaaatcac tgttgtttta   8280

agactgttga acccgtgtgt ttggctgggc tgtgagttac atgaagaaac tgcaaactag   8340

catatgcaga caaagctcac agactaggcg taaatggagg aaaatggacc aaaataaggc   8400

agggtgacac ataaaccttg ggcttcggag aaaactaagg gtggagatga actataatca   8460

cctgaataca atgtaagagt gcaataagtg tgcttattct aagctgtgaa cttcttttaa   8520

atcattcctt tctaatacat ttatgtatgt tccattgctg actaaaacca gctatgagaa   8580

catatgcctt tttattcatg ttaactacca gtttaagtgg ctaaccttaa tgtcttattt   8640

atcttcattt tgtattagtt tacataccag gtatgtgtgt gtgctgtact cttcttccct   8700

ttatttgaaa acacttttca ctgggtcatc tccttggcca ttccacaaca caactttggt   8760

ttggctttca atgtcacctt atttgatggc ctgtgtccca gtagcagaat ttatggtatt   8820

cccattgctg gctgctcttc cgaccctttg cttctacagc acttgtctct cctaagatag   8880

tcagaaacta actgatcagg ggatggactt caccattcat cgtgtctctt caattctatt   8940

aaatagacca ctcttgggct ttagaccagg aaaaaggaga cagctctagc catctaccaa   9000

gcctcaccct aaaaggtcac ccgtacttct tggtctgagg acaagtctcc actccagtaa   9060

gggagagggg aggaaatgct tcctgtttga aatgcagtga attcctatgg ctcctgtttc   9120

accacccgca cctatggcaa cccatataca ttcctcttgt ctgtaactgc caaaggttgg   9180

gtttatgtca cttcagttcc actcaagcat tgaaaaggtt ctcatggagt ctggggtgtg   9240

cccagtgaaa agatggggac tttttcatta tccacagacc tctctatacc tgctttgcaa   9300

aaattataat ggagtaacta tttttaaagc ttatttttca attcataaga aaaagacatt   9360

tattttcaat caaatggatg atgtctctta tcccttatcc ctcaatgttt gcttgaattt   9420

tgtttgttcc ctatacctac tccctaattc tttagttcct tcctgctcag gtcccttcat   9480

ttgtactttg gagtttttct catgtaaatt tgtataatgg aaaatattgt tcagtttgga   9540

tagaaagcat ggagaaataa ataaaaaaag atagctgaaa atcaaattga agaaatttat   9600

ttctgtgtaa agttatttaa aaactctgta ttatatttaa agaaaaaagc ccaacccccc   9660

aaaaagtgct atgtaattga tgtgaatatg cgaatactgc tataataaag attgactgca   9720

tggagaaa                                                            9728
```

<210> SEQ ID NO 6
<211> LENGTH: 804
<212> TYPE: PRT
<213> ORGANISM: Mus musculus

<400> SEQUENCE: 6

```
Met Ala Ala Leu Ser Gly Gly Gly Gly Ser Ser Ser Gly Gly Gly Gly
1               5                   10                  15

Gly Gly Gly Gly Gly Gly Gly Gly Gly Asp Gly Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60
```

```
Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
            100                 105                 110

Glu Gln Gln Leu Leu Glu Ser Leu Val Phe Gln Thr Pro Thr Asp Ala
        115                 120                 125

Ser Arg Asn Asn Pro Lys Ser Pro Gln Lys Pro Ile Val Arg Val Phe
    130                 135                 140

Leu Pro Asn Lys Gln Arg Thr Val Val Pro Ala Arg Cys Gly Val Thr
145                 150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
        195                 200                 205

Glu Val Leu Glu Asn Val Pro Leu Thr Thr His Asn Phe Val Arg Lys
    210                 215                 220

Thr Phe Phe Thr Leu Ala Phe Cys Asp Phe Cys Arg Lys Leu Leu Phe
225                 230                 235                 240

Gln Gly Phe Arg Cys Gln Thr Cys Gly Tyr Lys Phe His Gln Arg Cys
                245                 250                 255

Ser Thr Glu Val Pro Leu Met Cys Val Asn Tyr Asp Gln Leu Asp Leu
            260                 265                 270

Leu Phe Val Ser Lys Phe Phe Glu His His Pro Val Pro Gln Glu Glu
        275                 280                 285

Ala Ser Phe Pro Glu Thr Ala Leu Pro Ser Gly Ser Ser Ser Ala Pro
    290                 295                 300

Pro Ser Asp Ser Thr Gly Pro Gln Ile Leu Thr Ser Pro Ser Pro Ser
305                 310                 315                 320

Lys Ser Ile Pro Ile Pro Gln Pro Phe Arg Pro Ala Asp Glu Asp His
                325                 330                 335

Arg Asn Gln Phe Gly Gln Arg Asp Arg Ser Ser Ser Ala Pro Asn Val
            340                 345                 350

His Ile Asn Thr Ile Glu Pro Val Asn Ile Asp Glu Lys Phe Pro Glu
        355                 360                 365

Val Glu Leu Gln Asp Gln Arg Asp Leu Ile Arg Asp Gln Gly Phe Arg
    370                 375                 380

Gly Asp Gly Ala Pro Leu Asn Gln Leu Met Arg Cys Leu Arg Lys Tyr
385                 390                 395                 400

Gln Ser Arg Thr Pro Ser Pro Leu Leu His Ser Val Pro Ser Glu Ile
                405                 410                 415

Val Phe Asp Phe Glu Pro Gly Pro Val Phe Arg Gly Ser Thr Thr Gly
            420                 425                 430

Leu Ser Ala Thr Pro Pro Ala Ser Leu Pro Gly Ser Leu Thr Asn Val
        435                 440                 445

Lys Ala Leu Gln Lys Ser Pro Gly Pro Gln Arg Glu Arg Lys Ser Ser
    450                 455                 460

Ser Ser Ser Ser Ser Glu Asp Arg Ser Arg Met Lys Thr Leu Gly Arg
465                 470                 475                 480
```

-continued

```
Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
            500                 505                 510

Trp His Gly Asp Val Ala Val Lys Met Leu Asn Val Thr Ala Pro Thr
        515                 520                 525

Pro Gln Gln Leu Gln Ala Phe Lys Asn Glu Val Gly Val Leu Arg Lys
    530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
            580                 585                 590

Ile Ala Arg Gln Thr Ala Gln Gly Met Asp Tyr Leu His Ala Lys Ser
        595                 600                 605

Ile Ile His Arg Asp Leu Lys Ser Asn Asn Ile Phe Leu His Glu Asp
    610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
            660                 665                 670

Gln Ser Asp Val Tyr Ala Phe Gly Ile Val Leu Tyr Glu Leu Met Thr
        675                 680                 685

Gly Gln Leu Pro Tyr Ser Asn Ile Asn Asn Arg Asp Gln Ile Ile Phe
    690                 695                 700

Met Val Gly Arg Gly Tyr Leu Ser Pro Asp Leu Ser Lys Val Arg Ser
705                 710                 715                 720

Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys
```

<210> SEQ ID NO 7
<211> LENGTH: 2232
<212> TYPE: DNA
<213> ORGANISM: Oryctolagus cuniculus

<400> SEQUENCE: 7

```
atggggaatg tgtggaatat caaacaaatg attaagttga cacaggagca tatagaggcc      60

ctattggaca aatttggtgg ggagcataat ccaccatcaa tatatctgga ggcctacgaa     120

gaatacacca gcaagctaga tgccctccaa caaagagaac agcagttatt ggaatcccta     180

gtttttcaaa atcccacaga tgtgtcacgg agcaacccca agtcaccaca aaaacctatt     240

gttagagtct tcctgcccaa caaacagagg acagtggtac ctgcaagatg tggagttacg     300
```

-continued

```
gttcgagaca gtctaaagaa agcgctgatg atgagaggtc tgatcccaga atgctgtgct    360
gtttacagaa ttcaggatgg agagaagaag ccaattggct gggacactga tatttcctgg    420
ctcactggag aagagctgca tgtggaagtg ttagagaatg tcccactcac cacacataac    480
tttgtacgga aaactttttt caccttagca ttttgtgact tctgtagaaa gctgcttttc    540
cagggtttcc gctgtcaaac atgtggctac aaatttcacc agcgttgtag tacggaagtt    600
ccactgatgt gtgttaatta tgaccaactt gatttgctgt ttgtctccaa gttctttgaa    660
caccacccag taccacagga ggaggcctcc ttagcagaga ctgccctcac atctgggtca    720
tcgccttccg cacctccctc agactctatt gggcaccaaa ttctcaccag tccgtcccct    780
tcaaaatcca ttccgattcc acagtccttc cgaccagcag atgaagatca tcgaaatcag    840
tttgggcaac gagaccggtc ttcatcagcg cctaatgttc acattaacac aatagaacct    900
gtcaatattg atgaaaaatt cccagaagtg gaattacagg atcaaaggga cttgattaga    960
gaccaagggt ttcgtggtga tggagcccct ttgaaccagc tgatgcgctg tcttcggaaa   1020
taccaatccc ggactcccag tcccctccta ccttctgtcc ccagtgacat agtgtttgat   1080
tttgagcctg gcccagtgtt cagaggatcg accacgggtt tgtctgccac tccccctgcc   1140
tcattacctg gctcactcac tagtgtgaaa gctgtacaga gatccccagg acctcagcga   1200
gagaggaagt cgtcttcctc ctcagaagac aggaatcgaa tgaaaactct tggtagacgg   1260
gattcaagtg atgattggga gattcctgat gggcagatca ccgtgggaca gagaattgga   1320
tctggatcat ttggaaccgt ctacaaggga aaatggcacg gtgatgtggc agtaaaaatg   1380
ttgaatgtga cagcacctac acctcagcag ttacaggcct tcaaaaatga agtaggagta   1440
ctcaggaaaa cacgacatgt gaatatccta cttttcatgg gctattccac aaagccacag   1500
ctggctattg ttacccagtg gtgtgagggc tccagtttat atcaccatct ccacatcatt   1560
gagaccaaat tcgagatgat caaacttata gatattgcac ggcagactgc acagggcatg   1620
gattacttac acgccaagtc aatcatccac agagacctca agagtaataa tatatttctt   1680
catgaagacc tcacagtaaa aataggtgat tttggtctag ccacagtgaa atctcgatgg   1740
agtgggtccc atcagtttga acaattgtct ggatccattt tgtggatggc accagaagta   1800
atcagaatgc aagacaaaaa cccatatagc tttcagtcag atgtatatgc atttgggatt   1860
gttctgtatg aattgatgac tgggcagtta ccttactcaa acatcaacaa cagggaccag   1920
atcattttta tggtgggacg tggctacctg tctccagacc tcagtaaggt acggagtaac   1980
tgtccgaaag ccatgaagag attaatggca gagtgcctca aaaagaaaag agatgagaga   2040
ccactctttc cccaaattct cgcctccatt gagctgctgg cccgctcatt gccaaaaatc   2100
caccgcagtg catcagaacc ctccttgaat cgggctggtt tccagacaga ggattttagt   2160
ctatatgctt gtgcttctcc aaaaacaccc atccaggcag ggggatatgg agaatttgca   2220
gccttcaagt ag                                                       2232
```

<210> SEQ ID NO 8
<211> LENGTH: 743
<212> TYPE: PRT
<213> ORGANISM: Oryctolagus cuniculus

<400> SEQUENCE: 8

```
Met Gly Asn Val Trp Asn Ile Lys Gln Met Ile Lys Leu Thr Gln Glu
1               5                   10                  15

His Ile Glu Ala Leu Leu Asp Lys Phe Gly Gly Glu His Asn Pro Pro
```

-continued

```
            20                  25                  30

Ser Ile Tyr Leu Glu Ala Tyr Glu Glu Tyr Thr Ser Lys Leu Asp Ala
        35                  40                  45

Leu Gln Gln Arg Glu Gln Gln Leu Leu Glu Ser Leu Val Phe Gln Asn
    50                  55                  60

Pro Thr Asp Val Ser Arg Ser Asn Pro Lys Ser Pro Gln Lys Pro Ile
65                  70                  75                  80

Val Arg Val Phe Leu Pro Asn Lys Gln Arg Thr Val Val Pro Ala Arg
                85                  90                  95

Cys Gly Val Thr Val Arg Asp Ser Leu Lys Lys Ala Leu Met Met Arg
            100                 105                 110

Gly Leu Ile Pro Glu Cys Cys Ala Val Tyr Arg Ile Gln Asp Gly Glu
        115                 120                 125

Lys Lys Pro Ile Gly Trp Asp Thr Asp Ile Ser Trp Leu Thr Gly Glu
    130                 135                 140

Glu Leu His Val Glu Val Leu Glu Asn Val Pro Leu Thr Thr His Asn
145                 150                 155                 160

Phe Val Arg Lys Thr Phe Phe Thr Leu Ala Phe Cys Asp Phe Cys Arg
                165                 170                 175

Lys Leu Leu Phe Gln Gly Phe Arg Cys Gln Thr Cys Gly Tyr Lys Phe
            180                 185                 190

His Gln Arg Cys Ser Thr Glu Val Pro Leu Met Cys Val Asn Tyr Asp
        195                 200                 205

Gln Leu Asp Leu Leu Phe Val Ser Lys Phe Phe Glu His His Pro Val
    210                 215                 220

Pro Gln Glu Glu Ala Ser Leu Ala Glu Thr Ala Leu Thr Ser Gly Ser
225                 230                 235                 240

Ser Pro Ser Ala Pro Pro Ser Asp Ser Ile Gly His Gln Ile Leu Thr
                245                 250                 255

Ser Pro Ser Pro Ser Lys Ser Ile Pro Ile Pro Gln Ser Phe Arg Pro
            260                 265                 270

Ala Asp Glu Asp His Arg Asn Gln Phe Gly Gln Arg Asp Arg Ser Ser
        275                 280                 285

Ser Ala Pro Asn Val His Ile Asn Thr Ile Glu Pro Val Asn Ile Asp
    290                 295                 300

Glu Lys Phe Pro Glu Val Glu Leu Gln Asp Gln Arg Asp Leu Ile Arg
305                 310                 315                 320

Asp Gln Gly Phe Arg Gly Asp Gly Ala Pro Leu Asn Gln Leu Met Arg
                325                 330                 335

Cys Leu Arg Lys Tyr Gln Ser Arg Thr Pro Ser Pro Leu Leu Pro Ser
            340                 345                 350

Val Pro Ser Asp Ile Val Phe Asp Phe Glu Pro Gly Pro Val Phe Arg
        355                 360                 365

Gly Ser Thr Thr Gly Leu Ser Ala Thr Pro Pro Ala Ser Leu Pro Gly
    370                 375                 380

Ser Leu Thr Ser Val Lys Ala Val Gln Arg Ser Pro Gly Pro Gln Arg
385                 390                 395                 400

Glu Arg Lys Ser Ser Ser Ser Ser Glu Asp Arg Asn Arg Met Lys Thr
                405                 410                 415

Leu Gly Arg Arg Asp Ser Ser Asp Asp Trp Glu Ile Pro Asp Gly Gln
            420                 425                 430

Ile Thr Val Gly Gln Arg Ile Gly Ser Gly Ser Phe Gly Thr Val Tyr
        435                 440                 445
```

-continued

Lys Gly Lys Trp His Gly Asp Val Ala Val Lys Met Leu Asn Val Thr
450 455 460

Ala Pro Thr Pro Gln Gln Leu Gln Ala Phe Lys Asn Glu Val Gly Val
465 470 475 480

Leu Arg Lys Thr Arg His Val Asn Ile Leu Leu Phe Met Gly Tyr Ser
485 490 495

Thr Lys Pro Gln Leu Ala Ile Val Thr Gln Trp Cys Glu Gly Ser Ser
500 505 510

Leu Tyr His His Leu His Ile Ile Glu Thr Lys Phe Glu Met Ile Lys
515 520 525

Leu Ile Asp Ile Ala Arg Gln Thr Ala Gln Gly Met Asp Tyr Leu His
530 535 540

Ala Lys Ser Ile Ile His Arg Asp Leu Lys Ser Asn Asn Ile Phe Leu
545 550 555 560

His Glu Asp Leu Thr Val Lys Ile Gly Asp Phe Gly Leu Ala Thr Val
565 570 575

Lys Ser Arg Trp Ser Gly Ser His Gln Phe Glu Gln Leu Ser Gly Ser
580 585 590

Ile Leu Trp Met Ala Pro Glu Val Ile Arg Met Gln Asp Lys Asn Pro
595 600 605

Tyr Ser Phe Gln Ser Asp Val Tyr Ala Phe Gly Ile Val Leu Tyr Glu
610 615 620

Leu Met Thr Gly Gln Leu Pro Tyr Ser Asn Ile Asn Asn Arg Asp Gln
625 630 635 640

Ile Ile Phe Met Val Gly Arg Gly Tyr Leu Ser Pro Asp Leu Ser Lys
645 650 655

Val Arg Ser Asn Cys Pro Lys Ala Met Lys Arg Leu Met Ala Glu Cys
660 665 670

Leu Lys Lys Lys Arg Asp Glu Arg Pro Leu Phe Pro Gln Ile Leu Ala
675 680 685

Ser Ile Glu Leu Leu Ala Arg Ser Leu Pro Lys Ile His Arg Ser Ala
690 695 700

Ser Glu Pro Ser Leu Asn Arg Ala Gly Phe Gln Thr Glu Asp Phe Ser
705 710 715 720

Leu Tyr Ala Cys Ala Ser Pro Lys Thr Pro Ile Gln Ala Gly Gly Tyr
725 730 735

Gly Glu Phe Ala Ala Phe Lys
740

<210> SEQ ID NO 9
<211> LENGTH: 2186
<212> TYPE: DNA
<213> ORGANISM: Cavia porcellus

<400> SEQUENCE: 9
atggcggcgc tcagcggcgg cggtggcgcg gagcagggcc aggctctgtt caacggggac 60
atggagctcg aggccggcgc cggcgccgca gcctcttcgg ctgcagaccc tgccattccc 120
gaggaggtat ggaatatcaa acaaatgatt aagttgacgc aggaacacat agaggcccta 180
ttggacaaat ttggtggaga gcataatcca ccatcaatat acctggaggc ctatgaagaa 240
tacaccagca aactagatgc cctccaacaa agagaacagc agttactgga atccctcggg 300
aatggaactg atttttctgt ttctagctct gcatcactgg acaccgttac atcttcttct 360
tcttctagcc tttcagtact accttcatct ctttcagttt ttcaaaatcc tacagatgtg 420

```
tcacggagca accccaaatc accacaaaaa cctattgtta gagtcttcct gcccaacaaa    480
cagaggacag tggtacctgc aaggtgtgga gttacagtcc gagacagtct gaagaaagca    540
ctcatgatga gaggtcttat cccagagtgc tgtgctgtgt acagaattca ggatggagaa    600
aagaaaccaa ttggctggga cactgacatt tcctggctta ctggggaaga attacatgta    660
gaagtattgg agaatgttcc acttacaaca cacaattttg tatgtatctt tatatttttt    720
ttgctgtttg tctccaagtt ctttgaacac cacccaatac cacaggagga ggcttcctta    780
gcagagacca cccttacatc tggatcatcc ccttctgcac ccccctcaga gtccattggg    840
cccccaattc tcaccagccc atctccttca aaatccattc caattccaca gcctttccgg    900
ccaggagagg aagatcatcg aaatcaattt gggcagcgag accggtcctc atctgctccc    960
aatgtgcata taaacacaat agaacctgtc aatattgatg atttgattag agaccaaggg   1020
tttcgtagtg atggaggatc aactacaggt ttgtctgcca ccccacctgc ctcattacct   1080
ggctcactca ctaatgtgaa agccttacag aaatctccag gacctcagcg agaaaggaag   1140
tcatcttcat cctcagaaga cagaaatcga atgaaaacgc ttggtagacg ggactcaagt   1200
gatgattggg agattcctga tggcagatt acagtgggac aaagaattgg atctgggtca   1260
tttggaacag tctacaaggg gaagtggcat ggtgacgtgg cagtgaaaat gttgaatgtg   1320
acagcaccca cacctcaaca gttacaggcc ttcaaaaatg aagtaggagt actcaggaaa   1380
acacgacatg tgaatatcct actcttcatg ggctattcca caaagccaca gctagctatt   1440
gttacccagt ggtgtgaggg ctccagctta taccaccatc tccacatcat cgagaccaaa   1500
tttgagatga tcaaacttat agatattgca cgacagactg cccagggcat ggattactta   1560
cacgccaagt caatcatcca cagagacctc aagagtaata atatatttct tcacgaagac   1620
ctcacggtta aaataggtga ttttggtcta gccacagtga aatctcgatg gagtgggtcc   1680
catcagtttg aacagttgtc tggatccatt ttgtggatgg caccagaagt aatcagaatg   1740
cgagataaaa acccatacag ttttcagtcc gatgtatatg catttgggat tgttctatat   1800
gaattgatga ctgggcagtt accctattca aatatcaaca acagggacca gataattttt   1860
atggtgggac gaggatatct atctccagat ctcagcaagg tacggagtaa ctgtccaaaa   1920
gccatgaaga ggttaatggc ggagtgcctc aaaaagaaaa gagatgagag accactcttt   1980
ccccaaattc tcgcctctat tgagctgctg gcccgctcat tgccaaaaat tcaccgcagt   2040
gcatcagaac cctccttgaa tcgggctggt ttccaaacag aggattttag tctctatgct   2100
tgtgcttctc caaaaacacc catccaggca gggggatatg gtgcgtttcc tgtccactga   2160
tgcaaattaa atgagtgaga aataaa                                         2186
```

<210> SEQ ID NO 10
<211> LENGTH: 719
<212> TYPE: PRT
<213> ORGANISM: Cavia porcellus

<400> SEQUENCE: 10

```
Met Ala Ala Leu Ser Gly Gly Gly Gly Ala Glu Gln Gly Gln Ala Leu
1               5                   10                  15

Phe Asn Gly Asp Met Glu Leu Glu Ala Gly Ala Gly Ala Ala Ala Ser
            20                  25                  30

Ser Ala Ala Asp Pro Ala Ile Pro Glu Glu Val Trp Asn Ile Lys Gln
        35                  40                  45

Met Ile Lys Leu Thr Gln Glu His Ile Glu Ala Leu Leu Asp Lys Phe
```

-continued

```
    50                  55                  60

Gly Gly Glu His Asn Pro Pro Ser Ile Tyr Leu Glu Ala Tyr Glu Glu
65                  70                  75                  80

Tyr Thr Ser Lys Leu Asp Ala Leu Gln Gln Arg Glu Gln Gln Leu Leu
                85                  90                  95

Glu Ser Leu Gly Asn Gly Thr Asp Phe Ser Val Ser Ser Ser Ala Ser
            100                 105                 110

Leu Asp Thr Val Thr Ser Ser Ser Ser Ser Ser Leu Ser Val Leu Pro
        115                 120                 125

Ser Ser Leu Ser Val Phe Gln Asn Pro Thr Asp Val Ser Arg Ser Asn
    130                 135                 140

Pro Lys Ser Pro Gln Lys Pro Ile Val Arg Val Phe Leu Pro Asn Lys
145                 150                 155                 160

Gln Arg Thr Val Val Pro Ala Arg Cys Gly Val Thr Val Arg Asp Ser
                165                 170                 175

Leu Lys Lys Ala Leu Met Met Arg Gly Leu Ile Pro Glu Cys Cys Ala
            180                 185                 190

Val Tyr Arg Ile Gln Asp Gly Glu Lys Lys Pro Ile Gly Trp Asp Thr
        195                 200                 205

Asp Ile Ser Trp Leu Thr Gly Glu Glu Leu His Val Glu Val Leu Glu
    210                 215                 220

Asn Val Pro Leu Thr Thr His Asn Phe Val Cys Ile Phe Ile Phe Phe
225                 230                 235                 240

Leu Leu Phe Val Ser Lys Phe Phe Glu His His Pro Ile Pro Gln Glu
                245                 250                 255

Glu Ala Ser Leu Ala Glu Thr Thr Leu Thr Ser Gly Ser Ser Pro Ser
            260                 265                 270

Ala Pro Pro Ser Glu Ser Ile Gly Pro Pro Ile Leu Thr Ser Pro Ser
        275                 280                 285

Pro Ser Lys Ser Ile Pro Ile Pro Gln Pro Phe Arg Pro Gly Glu Glu
    290                 295                 300

Asp His Arg Asn Gln Phe Gly Gln Arg Asp Arg Ser Ser Ser Ala Pro
305                 310                 315                 320

Asn Val His Ile Asn Thr Ile Glu Pro Val Asn Ile Asp Asp Leu Ile
                325                 330                 335

Arg Asp Gln Gly Phe Arg Ser Asp Gly Gly Ser Thr Thr Gly Leu Ser
            340                 345                 350

Ala Thr Pro Pro Ala Ser Leu Pro Gly Ser Leu Thr Asn Val Lys Ala
        355                 360                 365

Leu Gln Lys Ser Pro Gly Pro Gln Arg Glu Arg Lys Ser Ser Ser Ser
    370                 375                 380

Ser Glu Asp Arg Asn Arg Met Lys Thr Leu Gly Arg Arg Asp Ser Ser
385                 390                 395                 400

Asp Asp Trp Glu Ile Pro Asp Gly Gln Ile Thr Val Gly Gln Arg Ile
                405                 410                 415

Gly Ser Gly Ser Phe Gly Thr Val Tyr Lys Gly Lys Trp His Gly Asp
            420                 425                 430

Val Ala Val Lys Met Leu Asn Val Thr Ala Pro Thr Pro Gln Gln Leu
        435                 440                 445

Gln Ala Phe Lys Asn Glu Val Gly Val Leu Arg Lys Thr Arg His Val
    450                 455                 460

Asn Ile Leu Leu Phe Met Gly Tyr Ser Thr Lys Pro Gln Leu Ala Ile
465                 470                 475                 480
```

-continued

```
Val Thr Gln Trp Cys Glu Gly Ser Ser Leu Tyr His His Leu His Ile
                485                 490                 495

Ile Glu Thr Lys Phe Glu Met Ile Lys Leu Ile Asp Ile Ala Arg Gln
            500                 505                 510

Thr Ala Gln Gly Met Asp Tyr Leu His Ala Lys Ser Ile Ile His Arg
        515                 520                 525

Asp Leu Lys Ser Asn Asn Ile Phe Leu His Glu Asp Leu Thr Val Lys
    530                 535                 540

Ile Gly Asp Phe Gly Leu Ala Thr Val Lys Ser Arg Trp Ser Gly Ser
545                 550                 555                 560

His Gln Phe Glu Gln Leu Ser Gly Ser Ile Leu Trp Met Ala Pro Glu
                565                 570                 575

Val Ile Arg Met Arg Asp Lys Asn Pro Tyr Ser Phe Gln Ser Asp Val
            580                 585                 590

Tyr Ala Phe Gly Ile Val Leu Tyr Glu Leu Met Thr Gly Gln Leu Pro
        595                 600                 605

Tyr Ser Asn Ile Asn Asn Arg Asp Gln Ile Ile Phe Met Val Gly Arg
    610                 615                 620

Gly Tyr Leu Ser Pro Asp Leu Ser Lys Val Arg Ser Asn Cys Pro Lys
625                 630                 635                 640

Ala Met Lys Arg Leu Met Ala Glu Cys Leu Lys Lys Lys Arg Asp Glu
                645                 650                 655

Arg Pro Leu Phe Pro Gln Ile Leu Ala Ser Ile Glu Leu Leu Ala Arg
            660                 665                 670

Ser Leu Pro Lys Ile His Arg Ser Ala Ser Glu Pro Ser Leu Asn Arg
        675                 680                 685

Ala Gly Phe Gln Thr Glu Asp Phe Ser Leu Tyr Ala Cys Ala Ser Pro
    690                 695                 700

Lys Thr Pro Ile Gln Ala Gly Gly Tyr Gly Ala Phe Pro Val His
705                 710                 715
```

<210> SEQ ID NO 11
<211> LENGTH: 3229
<212> TYPE: DNA
<213> ORGANISM: Canis familiaris

<400> SEQUENCE: 11

```
gtaatgctgg attttcatgg aataagtttg acctgtgctg cagtggcctc cagcaaggta      60

cccgcaagat gtggagttac agtccgggac agtctaaaga aagctctgat gatgagaggt     120

ctaatcccag agtgctgtgc tgtttacaga attcaggatg gagagaagaa accgattggc     180

tgggacactg atatttcctg gctcactgga gaggaattgc atgtagaagt gttggaaaat     240

gttccgctta ccacacacaa ctttgtacgg aaaacttttt tcaccttagc attttgtgac     300

ttttgtcgaa agctgctttt ccagggtttt cgctgtcaaa catgtggtta taaatttcac     360

cagcgttgta gtacagaggt tccactgatg tgtgttaatt atgaccaact tgatttgctg     420

tttgtctcca agttctttga acaccaccca ataccacagg aggaggcctc catagcagag     480

actgccctta cgtctggatc atccccttct gctcccccct ccgattctcc tgggccccca     540

attctgacca gtccgtctcc ttcaaaatcc attccaattc cacagccttt ccgaccagca     600

gatgaagatc atcgaaatca gtttggacaa cgagaccggt cctcatcagc tccaaatgtg     660

catataaaca caatagaacc cgtcaacatt gatgacttga ttagagacca agggtttcgt     720

agtgatggag gatcaaccac aggtttgtct gccacccccc ctgcctcatt gcctggctca     780
```

```
ctcactaatg taaaagcatt acagaaatct ccaggacctc agcgggaaag aaaatcatct    840
tcatcctcag aagataggaa tcgaatgaaa acacttggta gacgggattc aagtgatgat    900
tgggagatac ctgatgggca gatcacagtg ggacagagaa ttggatccgg gtcatttggg    960
acagtctaca agggaaagtg gcatggtgac gtggcagtga aaatgttgaa tgtgacagca   1020
cccacacctc agcagttaca ggccttcaaa aatgaagtag gagtactcag gaaaactcga   1080
catgtgaata tcctactctt tatgggctat tcaacaaagc cccaactggc tattgttacc   1140
cagtggtgtg agggctccag cttatatcac catctccaca tcattgagac caaatttgag   1200
atgataaagc ttatagatat tgcacggcag actgcacagg gcatggatta cttacacgcc   1260
aagtcaatca tccacagaga cctcaagagt aataatattt ttcttcatga agacctcaca   1320
gtaaaaatag gtgattttgg tctagccaca gtgaaatctc gatggagtgg gtcccatcag   1380
tttgaacagt tgtctggatc cattttgtgg atggcaccag aagtgatccg aatgcaagac   1440
aaaaacccat atagcttcca gtcagatgta tacgcatttg ggattgttct atatgaattg   1500
atgacagggc agttacctta ttcaaacatc aacaacaggg accagataat tttatggtg    1560
ggacgaggat atctttctcc agatctcagt aaggtacgga gtaactgtcc aaaagccatg   1620
aagagattga tggcagagtg cctaaaaaag aaaagagatg agaggccact ctttccccaa   1680
attctcgcct ctattgagct gctggcccgc tcattgccaa aaattcaccg cagtgcatca   1740
gaaccctcct tgaatcgggc tggcttccaa acagaggatt ttagtctcta tgcttgcgct   1800
tctccaaaaa cacccatcca ggcaggggga tacggagaat ttgcagcctt caagtagcca   1860
caccatcatg gcaacaacta ctcttatttc ttaagtcttg tgttcgtaca atttgttaac   1920
atcaaaacac agttctgttc ctcaaatctt tttttaaaga tacagaattt tcaatgcata   1980
agctggtgtg gaacagaatg gaatttccca tccaacaaaa gagggaagaa tgttttagga   2040
accagaattc tctgctgcca gtgtttcttc ttcaacacaa ataccacgtg catacaagtc   2100
tgcccactcc caggaaggaa gaggagagcc tgagttctga ccttttgatg gtcaggcatg   2160
atggaaagaa actgctgcta cagcttggga gattggctgt ggagagcctg cccgtcagct   2220
ctgcccttct aaccgccaga tgagtgtgtg gctggtcacc tgacagggca gctgcaatcg   2280
ccaagcatcg ttctctttcc tgtcctggga ttttgtcgtg gagctctttc cccctagtca   2340
ccaccggttc atttctgagg gatggaacaa aaatgcagca tggcctttct gtgtggtgca   2400
tgtccggtct ttgacaaatt tttatcaagt gaagctcttg tatttaaatg gagaatgaga   2460
ggcgaggggg ggggatcacg ttttggtgta ggggcaaagg gaatgctgca tctttttcct   2520
gacccactgg gtttctggcc tttgtttcct tgctcactga gggtgtctgc ctataaccac   2580
gcaggctgga aagtgctggc acacattgcc ttctcttctc actgggtcca gcaatgaaga   2640
caagtgttgg ggattttttt ttttgccctc cacaatgtag caagttctca ggaaaataca   2700
gttaatatct tcctcctaag ctcttccagt catcaagtac ttatgtggct actttgtcca   2760
gggcacaaaa tgccatggcg gtatccaatt aaaagcctac aaaactgctt gataacagtt   2820
ttgaatgtgt gagacattta tgtaatttaa atgtaaggta caagttttaa tttctgagtt   2880
tctctattat atttttatta aaaagaaaat aattttcaga tttaattgaa ttggaataaa   2940
ataatacttc ccaccagaat tatatatcct ggaaaattgt atttttgtta tataaacaac   3000
ttttaaagaa agatcattat ccttttctct acctaaatat ggggagtctt agcataatga   3060
cagatattta taatttttaa attaatggta cttgctggat ccacactaac atctttgcta   3120
```

-continued

```
atatctcatg ttttcctcca acttactcct acactacatc ctccatcctc tttccagtct   3180

tttatctaga atatgcaacc taaaataaaa atggtggtgt ctccattca              3229


<210> SEQ ID NO 12
<211> LENGTH: 617
<212> TYPE: PRT
<213> ORGANISM: Canis familiaris

<400> SEQUENCE: 12

Met Leu Asp Phe His Gly Ile Ser Leu Thr Cys Ala Ala Val Ala Ser
1               5                   10                  15

Ser Lys Val Pro Ala Arg Cys Gly Val Thr Val Arg Asp Ser Leu Lys
            20                  25                  30

Lys Ala Leu Met Met Arg Gly Leu Ile Pro Glu Cys Cys Ala Val Tyr
        35                  40                  45

Arg Ile Gln Asp Gly Glu Lys Lys Pro Ile Gly Trp Asp Thr Asp Ile
    50                  55                  60

Ser Trp Leu Thr Gly Glu Glu Leu His Val Glu Val Leu Glu Asn Val
65                  70                  75                  80

Pro Leu Thr Thr His Asn Phe Val Arg Lys Thr Phe Phe Thr Leu Ala
                85                  90                  95

Phe Cys Asp Phe Cys Arg Lys Leu Leu Phe Gln Gly Phe Arg Cys Gln
            100                 105                 110

Thr Cys Gly Tyr Lys Phe His Gln Arg Cys Ser Thr Glu Val Pro Leu
        115                 120                 125

Met Cys Val Asn Tyr Asp Gln Leu Asp Leu Leu Phe Val Ser Lys Phe
    130                 135                 140

Phe Glu His His Pro Ile Pro Gln Glu Glu Ala Ser Ile Ala Glu Thr
145                 150                 155                 160

Ala Leu Thr Ser Gly Ser Ser Pro Ser Ala Pro Pro Ser Asp Ser Pro
                165                 170                 175

Gly Pro Pro Ile Leu Thr Ser Pro Ser Pro Ser Lys Ser Ile Pro Ile
            180                 185                 190

Pro Gln Pro Phe Arg Pro Ala Asp Glu Asp His Arg Asn Gln Phe Gly
        195                 200                 205

Gln Arg Asp Arg Ser Ser Ser Ala Pro Asn Val His Ile Asn Thr Ile
    210                 215                 220

Glu Pro Val Asn Ile Asp Asp Leu Ile Arg Asp Gln Gly Phe Arg Ser
225                 230                 235                 240

Asp Gly Gly Ser Thr Thr Gly Leu Ser Ala Thr Pro Pro Ala Ser Leu
                245                 250                 255

Pro Gly Ser Leu Thr Asn Val Lys Ala Leu Gln Lys Ser Pro Gly Pro
            260                 265                 270

Gln Arg Glu Arg Lys Ser Ser Ser Ser Ser Glu Asp Arg Asn Arg Met
        275                 280                 285

Lys Thr Leu Gly Arg Arg Asp Ser Ser Asp Asp Trp Glu Ile Pro Asp
    290                 295                 300

Gly Gln Ile Thr Val Gly Gln Arg Ile Gly Ser Gly Ser Phe Gly Thr
305                 310                 315                 320

Val Tyr Lys Gly Lys Trp His Gly Asp Val Ala Val Lys Met Leu Asn
                325                 330                 335

Val Thr Ala Pro Thr Pro Gln Gln Leu Gln Ala Phe Lys Asn Glu Val
            340                 345                 350

Gly Val Leu Arg Lys Thr Arg His Val Asn Ile Leu Leu Phe Met Gly
```

-continued

```
        355                 360                 365

Tyr Ser Thr Lys Pro Gln Leu Ala Ile Val Thr Gln Trp Cys Glu Gly
    370                 375                 380

Ser Ser Leu Tyr His His Leu His Ile Ile Glu Thr Lys Phe Glu Met
385                 390                 395                 400

Ile Lys Leu Ile Asp Ile Ala Arg Gln Thr Ala Gln Gly Met Asp Tyr
                405                 410                 415

Leu His Ala Lys Ser Ile Ile His Arg Asp Leu Lys Ser Asn Asn Ile
            420                 425                 430

Phe Leu His Glu Asp Leu Thr Val Lys Ile Gly Asp Phe Gly Leu Ala
        435                 440                 445

Thr Val Lys Ser Arg Trp Ser Gly Ser His Gln Phe Glu Gln Leu Ser
    450                 455                 460

Gly Ser Ile Leu Trp Met Ala Pro Glu Val Ile Arg Met Gln Asp Lys
465                 470                 475                 480

Asn Pro Tyr Ser Phe Gln Ser Asp Val Tyr Ala Phe Gly Ile Val Leu
                485                 490                 495

Tyr Glu Leu Met Thr Gly Gln Leu Pro Tyr Ser Asn Ile Asn Asn Arg
            500                 505                 510

Asp Gln Ile Ile Phe Met Val Gly Arg Gly Tyr Leu Ser Pro Asp Leu
        515                 520                 525

Ser Lys Val Arg Ser Asn Cys Pro Lys Ala Met Lys Arg Leu Met Ala
    530                 535                 540

Glu Cys Leu Lys Lys Lys Arg Asp Glu Arg Pro Leu Phe Pro Gln Ile
545                 550                 555                 560

Leu Ala Ser Ile Glu Leu Leu Ala Arg Ser Leu Pro Lys Ile His Arg
                565                 570                 575

Ser Ala Ser Glu Pro Ser Leu Asn Arg Ala Gly Phe Gln Thr Glu Asp
            580                 585                 590

Phe Ser Leu Tyr Ala Cys Ala Ser Pro Lys Thr Pro Ile Gln Ala Gly
        595                 600                 605

Gly Tyr Gly Glu Phe Ala Ala Phe Lys
    610                 615
```

```
<210> SEQ ID NO 13
<211> LENGTH: 1889
<212> TYPE: DNA
<213> ORGANISM: Canis familiaris

<400> SEQUENCE: 13

ggaatatcaa acaaatgatt aagttgacac aggaacatat agaagcccta ttggacaagt     60

ttggtgggga gcataatcca ccatcaatat atctggaggc ctatgaagaa tacaccagca    120

aactagatgc cctccaacag cgagaacaac agttattgga atccctgggg aatggaactg    180

atttttctgt ttctagctct gcatcaacgg acaccgttac atcttcttcc tcttctagcc    240

tttcagtgct accttcatct ctttcagttt ttcaaaatcc cacagatata tcacggagca    300

atcccaagtc accacaaaaa cctatcgtta gagtcttcct gcccaataaa cagaggacgg    360

tggtacccgc aagatgtgga gttacagtcc gggacagtct aaagaaagct ctgatgatga    420

gaggtctaat cccagagtgc tgtgctgttt acagaattca ggatggagag aagaaaccga    480

ttggctggga cactgatatt tcctggctca ctggagagga attgcatgta gaagtgttgg    540

aaaatgttcc gcttaccaca cacaactttg tacggaaaac ttttttcacc ttagcatttt    600

gtgacttttg tcgaaagctg cttttccagg gttttcgctg tcaaacatgt ggttataaat    660
```

```
ttcaccagcg ttgtagtaca gaggttccac tgatgtgtgt taattatgac caacttgatt    720

tgctgtttgt ctccaagttc tttgaacacc acccaatacc acaggaggag gcctccatag    780

cagagactgc ccttacgtct ggatcatccc cttctgctcc cccctccgat tctcctgggc    840

ccccaattct gaccagtccg tctccttcaa aatccattcc aattccacag cctttccgac    900

cagcagatga agatcatcga aatcagtttg gacaacgaga ccggtcctca tcagctccaa    960

atgtgcatat aaacacaata gaacccgtca acattgatga cttgattaga gaccaagggt   1020

ttcgtagtga tggaggatca accacaggtt tgtctgccac ccccccctgcc tcattgcctg   1080

gctcactcac taatgtaaaa gcattacaga aatctccagg acctcagcgg gaaagaaaat   1140

catcttcatc ctcagaagat aggaatcgaa tgaaaacact tggtagacgg gattcaagtg   1200

atgattggga gatacctgat gggcagatca cagtgggaca gagaattgga tccgggtcat   1260

ttgggacagt ctacaaggga aagtggcatg gtgacgtggc agtgaaaatg ttgaatgtga   1320

cagcacccac acctcagcag ttacaggcct tcaaaaatga agtaggagta ctcaggaaaa   1380

ctcgacatgt gaatatccta ctctttatgg gctattcaac aaagccccaa ctggctattg   1440

ttacccagtg gtgtgagggc tccagcttat atcaccatct ccacatcatt gagaccaaat   1500

ttgagatgat aaagcttata gatattgcac ggcagactgc acagggcatg gattacttac   1560

acgccaagtc aatcatccac agagacctca agagtaataa tatttttctt catgaagacc   1620

tcacagtaaa aataggtgat tttggtctag ccacagtgaa atctcgatgg agtgggtccc   1680

atcagtttga acagttgtct ggatccattt tgtggatggc accagaagtg atccgaatgc   1740

aagacaaaaa cccatatagc ttccagtcag atgtatacgc atttgggatt gttctatatg   1800

aattgatgac agggcagtta ccttattcaa acatcaacaa cagggaccag ctcagatcat   1860

gatcacggtg tcatgagatc aagccccac                                     1889
```

```
<210> SEQ ID NO 14
<211> LENGTH: 615
<212> TYPE: PRT
<213> ORGANISM: Canis familiaris

<400> SEQUENCE: 14

Met Ile Lys Leu Thr Gln Glu His Ile Glu Ala Leu Leu Asp Lys Phe
1               5                   10                  15

Gly Gly Glu His Asn Pro Pro Ser Ile Tyr Leu Glu Ala Tyr Glu Glu
            20                  25                  30

Tyr Thr Ser Lys Leu Asp Ala Leu Gln Gln Arg Glu Gln Gln Leu Leu
        35                  40                  45

Glu Ser Leu Gly Asn Gly Thr Asp Phe Ser Val Ser Ser Ser Ala Ser
    50                  55                  60

Thr Asp Thr Val Thr Ser Ser Ser Ser Ser Ser Leu Ser Val Leu Pro
65                  70                  75                  80

Ser Ser Leu Ser Val Phe Gln Asn Pro Thr Asp Ile Ser Arg Ser Asn
                85                  90                  95

Pro Lys Ser Pro Gln Lys Pro Ile Val Arg Val Phe Leu Pro Asn Lys
            100                 105                 110

Gln Arg Thr Val Val Pro Ala Arg Cys Gly Val Thr Val Arg Asp Ser
        115                 120                 125

Leu Lys Lys Ala Leu Met Met Arg Gly Leu Ile Pro Glu Cys Cys Ala
    130                 135                 140

Val Tyr Arg Ile Gln Asp Gly Glu Lys Lys Pro Ile Gly Trp Asp Thr
```

```
145                 150                 155                 160

Asp Ile Ser Trp Leu Thr Gly Glu Glu Leu His Val Glu Val Leu Glu
                165                 170                 175

Asn Val Pro Leu Thr Thr His Asn Phe Val Arg Lys Thr Phe Phe Thr
            180                 185                 190

Leu Ala Phe Cys Asp Phe Cys Arg Lys Leu Leu Phe Gln Gly Phe Arg
        195                 200                 205

Cys Gln Thr Cys Gly Tyr Lys Phe His Gln Arg Cys Ser Thr Glu Val
    210                 215                 220

Pro Leu Met Cys Val Asn Tyr Asp Gln Leu Asp Leu Leu Phe Val Ser
225                 230                 235                 240

Lys Phe Phe Glu His His Pro Ile Pro Gln Glu Glu Ala Ser Ile Ala
                245                 250                 255

Glu Thr Ala Leu Thr Ser Gly Ser Ser Pro Ser Ala Pro Pro Ser Asp
            260                 265                 270

Ser Pro Gly Pro Pro Ile Leu Thr Ser Pro Ser Pro Ser Lys Ser Ile
        275                 280                 285

Pro Ile Pro Gln Pro Phe Arg Pro Ala Asp Glu Asp His Arg Asn Gln
    290                 295                 300

Phe Gly Gln Arg Asp Arg Ser Ser Ser Ala Pro Asn Val His Ile Asn
305                 310                 315                 320

Thr Ile Glu Pro Val Asn Ile Asp Asp Leu Ile Arg Asp Gln Gly Phe
                325                 330                 335

Arg Ser Asp Gly Gly Ser Thr Thr Gly Leu Ser Ala Thr Pro Pro Ala
            340                 345                 350

Ser Leu Pro Gly Ser Leu Thr Asn Val Lys Ala Leu Gln Lys Ser Pro
        355                 360                 365

Gly Pro Gln Arg Glu Arg Lys Ser Ser Ser Ser Ser Glu Asp Arg Asn
    370                 375                 380

Arg Met Lys Thr Leu Gly Arg Arg Asp Ser Ser Asp Asp Trp Glu Ile
385                 390                 395                 400

Pro Asp Gly Gln Ile Thr Val Gly Gln Arg Ile Gly Ser Gly Ser Phe
                405                 410                 415

Gly Thr Val Tyr Lys Gly Lys Trp His Gly Asp Val Ala Val Lys Met
            420                 425                 430

Leu Asn Val Thr Ala Pro Thr Pro Gln Gln Leu Gln Ala Phe Lys Asn
        435                 440                 445

Glu Val Gly Val Leu Arg Lys Thr Arg His Val Asn Ile Leu Leu Phe
    450                 455                 460

Met Gly Tyr Ser Thr Lys Pro Gln Leu Ala Ile Val Thr Gln Trp Cys
465                 470                 475                 480

Glu Gly Ser Ser Leu Tyr His His Leu His Ile Ile Glu Thr Lys Phe
                485                 490                 495

Glu Met Ile Lys Leu Ile Asp Ile Ala Arg Gln Thr Ala Gln Gly Met
            500                 505                 510

Asp Tyr Leu His Ala Lys Ser Ile Ile His Arg Asp Leu Lys Ser Asn
        515                 520                 525

Asn Ile Phe Leu His Glu Asp Leu Thr Val Lys Ile Gly Asp Phe Gly
    530                 535                 540

Leu Ala Thr Val Lys Ser Arg Trp Ser Gly Ser His Gln Phe Glu Gln
545                 550                 555                 560

Leu Ser Gly Ser Ile Leu Trp Met Ala Pro Glu Val Ile Arg Met Gln
                565                 570                 575
```

```
Asp Lys Asn Pro Tyr Ser Phe Gln Ser Asp Val Tyr Ala Phe Gly Ile
            580                 585                 590

Val Leu Tyr Glu Leu Met Thr Gly Gln Leu Pro Tyr Ser Asn Ile Asn
        595                 600                 605

Asn Arg Asp Gln Leu Arg Ser
    610                 615


<210> SEQ ID NO 15
<211> LENGTH: 3521
<212> TYPE: DNA
<213> ORGANISM: Felis catus
<220> FEATURE:
<221> NAME/KEY: misc_feature
<222> LOCATION: (630)..(649)
<223> OTHER INFORMATION: n is a, c, g, or t

<400> SEQUENCE: 15

atgcctaacc tcagtctctg ccaccacggc caatttgctc atgtgcccac tgtgtcggca     60

ctgggatatt ttgtgatttg ccttggccat tgtccactgt ccttgacatt gcctgaagga    120

gaaccactga tgctaatgtt gaaggtgacc tttgcaggct ctccactact cataccaaag    180

atgcggcccc ctgataatcc cagagccact gtctgcacat gggcaaaaca ggctacattc    240

tgtgcagact ggggagaaag gttccaagaa cacagtgcca tagttttggg cagagagttt    300

caacacagca tagtgtctat ggcagtatct ggatttggcc gggggaagtg cccaagagga    360

gacagtcagg ctgtgtccta cggccaagga cctgcactta tttttgcatg cagtggttta    420

gcacagggaa gagaacgaag taggaaatcg gagccatgga aacggcagag cggaggaaac    480

gtgcacgcgc gagggtgggc acgaaaggaa agaaccctcc ccagaagact gcgcgagggc    540

gctcctagga ttacgtcacg caccccgcga aaactgaaat gtactgtgtg tggtctttta    600

attgaactat cttccttatg tgcacttaan nnnnnnnnnn nnnnnnnnng cggcggcggc    660

ggtggcgcgg agcagggcca ggctctgttc aacggggaca tggagcccga agccggcgcc    720

gcggcctctt cggctgcgga ccctgccatt cccgaggagg tgtggaatat caaacaaatg    780

attaagttga cacaggaaca tatagaggcc ctattggaca aatttggtgg ggagcataat    840

ccaccatcaa tatatctaga ggcctatgaa gaatacacca gcaagctaga tgccctccaa    900

cagagagaac aacagttatt ggaatccctg gggaatggaa ctgatttttc tgtttctagc    960

tctgcatcaa cagacaccgt tacatcttcc tcctcttcta gcctttcagt gctaccttca   1020

tctctttcag tttttcaaaa ccccacagat gtgtcacgga gcaatcccaa gtcaccacag   1080

aaacctatcg ttagagtctt cctgcctaat aaacagagga cagtggtacc tgcaagatgt   1140

ggagttacag tccgggacag tctaaagaaa gctctgatga tgagaggtct aatccctgag   1200

tgctgtgctg tttacagaat tcaggatgga gagaagaaac caattggctg ggacactgat   1260

atctcctggc tcaccggaga ggaattgcat gtagaagtgt tggaaaatgt tccacttaca   1320

actcacaact ttgtatgtac ggaaaacgtt ttcaccttag cattttgtga cttttgtcga   1380

aagctgcttt tccaaggttt tcgctgtcaa acgtgtggtt ataaatttca ccagcgttgt   1440

agtacagagg ttccactgat gtgtgttaat tatgaccaac ttgatttgct gtttgtctcc   1500

aagttctttg aacaccaccc aataccacag gaggaggcct ccatagcaga gactgcccta   1560

acgtctggat cgtccccttc tgcccccccc tccgattcta ctgggcccca aattctcacc   1620

agtccgtctc cttcaaaatc cattccaatt ccacagcctt tccgaccagc agatgaagat   1680

catcgaaatc aatttggaca gcgagaccgg tcctcatcag ctccaaatgt gcatataaat   1740
```

```
acaatagaac ctgtcaatat tgatgacttg attagagacc aggggtttcg tagtgatgga   1800

ggatcaacca caggcttgtc tgccaccccc cctgcctcat tgccgggctc tctcactaat   1860

gtaaaagcat tacagaaatc tccagggcct cagcgggaaa ggaaatcttc ttcatcctca   1920

gaagatagga atcgaatgaa aacacttggt agaagggatt caagtgatga ttgggagatt   1980

cctgatgggc agatcacagt gggacagaga attggatccg ggtcatttgg gacagtctac   2040

aagggaaagt ggcatggtga tgtggcagtg aaaatgttga atgtgacagc acccacacct   2100

cagcagttac aggccttcaa aaatgaagta ggagtactca ggaaaactcg gcatgtgaac   2160

atcctgctct tcatgggcta ttcaacaaag ccccagctgg ctattgtcac ccagtggtgt   2220

gagggctcca gcttatacca ccatctccac atcatcgaga ccaaattcga gatgatcaag   2280

ctgatagata ttgctcggca gactgcgcag ggcatggatt acttacacgc caagtcaatc   2340

atccacagag acctcaagag taataatatt tttcttcacg aagacctcac agtaaaaata   2400

ggtgattttg gtctagccac agtgaaatct cgatggagtg ggtcccatca gtttgaacag   2460

ttgtctggat ccattttgtg gatggcacca gaagtaattc gaatgcaaga taaaaaccca   2520

tatagctttc agtcagatgt atatgcattt gggattgttc tatatgaatt gatgactgga   2580

cagttacctt attcaaacat caacaacagg gaccagataa tttttatggt gggacgagga   2640

tatctttctc cagatctcag taaggtacga agtaactgtc caaaagccat gaagagattg   2700

atggcagagt gcctaaaaaa gaaaagagat gagaggccac tgtttcccca aattcttgcc   2760

tctattgagc tgctggcccg ctcattgcca aaaattcacc gcagtgcatc agaaccctcc   2820

ttgaatcggg ctggcttcca gacagaggat tttagtctct atgcttgtgc ttctccaaaa   2880

acacccatcc aggcaggggg atatggtgcg tttcccgtcc actgagataa gttagatgag   2940

tgcgcgagtg cagggggccg gggccaagga ggtggaaatg tgcgtgcttc tgtactaagt   3000

tggatagcat cttctttttt aaaaaaagat gaaccaaaga atgtgtatgt ttttaaagac   3060

tagatataat tatttcctga tctaaaatgt atacttagct ttggattttc aatatccaag   3120

ggttttcaaa atgcacagac attgctgaac atttgcagta cctcttctgg aggctttact   3180

tcctgttaca aattggtttt gtttactggc ttatcctaat tattaaactt caattaaact   3240

tttctcctgc accttttgtt atgagctatc acatgtccct tagggactcg caagagcagt   3300

actgcccccg tgtacgggct tgcaggtaga aaggggatga cgggttttaa cacctgtgtg   3360

aggcaaggca gtccgaacag atctcattta ggaagccacg agagttgaat aagttatttt   3420

tattcttagt atttttctg taactacttt ttattataac ttggaaaata tggatgtcct   3480

ttatacacct tagcaataga ctgaatttct ttttataaat t                       3521
```

```
<210> SEQ ID NO 16
<211> LENGTH: 974
<212> TYPE: PRT
<213> ORGANISM: Felis catus
<220> FEATURE:
<221> NAME/KEY: misc_feature
<222> LOCATION: (210)..(217)
<223> OTHER INFORMATION: Xaa can be any naturally occurring amino acid

<400> SEQUENCE: 16

Met Pro Asn Leu Ser Leu Cys His His Gly Gln Phe Ala His Val Pro
1               5                   10                  15

Thr Val Ser Ala Leu Gly Tyr Phe Val Ile Cys Leu Gly His Cys Pro
            20                  25                  30
```

-continued

```
Leu Ser Leu Thr Leu Pro Glu Gly Glu Pro Leu Met Leu Met Leu Lys
        35                  40                  45

Val Thr Phe Ala Gly Ser Pro Leu Leu Ile Pro Lys Met Arg Pro Pro
    50                  55                  60

Asp Asn Pro Arg Ala Thr Val Cys Thr Trp Ala Lys Gln Ala Thr Phe
65                  70                  75                  80

Cys Ala Asp Trp Gly Glu Arg Phe Gln Glu His Ser Ala Ile Val Leu
                85                  90                  95

Gly Arg Glu Phe Gln His Ser Ile Val Ser Met Ala Val Ser Gly Phe
            100                 105                 110

Gly Arg Gly Lys Cys Pro Arg Gly Asp Ser Gln Ala Val Ser Tyr Gly
        115                 120                 125

Gln Gly Pro Ala Leu Ile Phe Ala Cys Ser Gly Leu Ala Gln Gly Arg
    130                 135                 140

Glu Arg Ser Arg Lys Ser Glu Pro Trp Lys Arg Gln Ser Gly Gly Asn
145                 150                 155                 160

Val His Ala Arg Gly Trp Ala Arg Lys Glu Arg Thr Leu Pro Arg Arg
                165                 170                 175

Leu Arg Glu Gly Ala Pro Arg Ile Thr Ser Arg Thr Pro Arg Lys Leu
            180                 185                 190

Lys Cys Thr Val Cys Gly Leu Leu Ile Glu Leu Ser Ser Leu Cys Ala
        195                 200                 205

Leu Xaa Xaa Xaa Xaa Xaa Xaa Xaa Xaa Gly Gly Gly Gly Gly Ala Glu
    210                 215                 220

Gln Gly Gln Ala Leu Phe Asn Gly Asp Met Glu Pro Glu Ala Gly Ala
225                 230                 235                 240

Ala Ala Ser Ser Ala Ala Asp Pro Ala Ile Pro Glu Glu Val Trp Asn
                245                 250                 255

Ile Lys Gln Met Ile Lys Leu Thr Gln Glu His Ile Glu Ala Leu Leu
            260                 265                 270

Asp Lys Phe Gly Gly Glu His Asn Pro Pro Ser Ile Tyr Leu Glu Ala
        275                 280                 285

Tyr Glu Glu Tyr Thr Ser Lys Leu Asp Ala Leu Gln Gln Arg Glu Gln
    290                 295                 300

Gln Leu Leu Glu Ser Leu Gly Asn Gly Thr Asp Phe Ser Val Ser Ser
305                 310                 315                 320

Ser Ala Ser Thr Asp Thr Val Thr Ser Ser Ser Ser Ser Ser Leu Ser
                325                 330                 335

Val Leu Pro Ser Ser Leu Ser Val Phe Gln Asn Pro Thr Asp Val Ser
            340                 345                 350

Arg Ser Asn Pro Lys Ser Pro Gln Lys Pro Ile Val Arg Val Phe Leu
        355                 360                 365

Pro Asn Lys Gln Arg Thr Val Val Pro Ala Arg Cys Gly Val Thr Val
    370                 375                 380

Arg Asp Ser Leu Lys Lys Ala Leu Met Met Arg Gly Leu Ile Pro Glu
385                 390                 395                 400

Cys Cys Ala Val Tyr Arg Ile Gln Asp Gly Glu Lys Lys Pro Ile Gly
                405                 410                 415

Trp Asp Thr Asp Ile Ser Trp Leu Thr Gly Glu Glu Leu His Val Glu
            420                 425                 430

Val Leu Glu Asn Val Pro Leu Thr Thr His Asn Phe Val Cys Thr Glu
        435                 440                 445

Asn Val Phe Thr Leu Ala Phe Cys Asp Phe Cys Arg Lys Leu Leu Phe
```

```
    450                 455                 460

Gln Gly Phe Arg Cys Gln Thr Cys Gly Tyr Lys Phe His Gln Arg Cys
465                 470                 475                 480

Ser Thr Glu Val Pro Leu Met Cys Val Asn Tyr Asp Gln Leu Asp Leu
                485                 490                 495

Leu Phe Val Ser Lys Phe Phe Glu His His Pro Ile Pro Gln Glu Glu
            500                 505                 510

Ala Ser Ile Ala Glu Thr Ala Leu Thr Ser Gly Ser Ser Pro Ser Ala
        515                 520                 525

Pro Pro Ser Asp Ser Thr Gly Pro Gln Ile Leu Thr Ser Pro Ser Pro
    530                 535                 540

Ser Lys Ser Ile Pro Ile Pro Gln Pro Phe Arg Pro Ala Asp Glu Asp
545                 550                 555                 560

His Arg Asn Gln Phe Gly Gln Arg Asp Arg Ser Ser Ser Ala Pro Asn
                565                 570                 575

Val His Ile Asn Thr Ile Glu Pro Val Asn Ile Asp Asp Leu Ile Arg
            580                 585                 590

Asp Gln Gly Phe Arg Ser Asp Gly Gly Ser Thr Thr Gly Leu Ser Ala
        595                 600                 605

Thr Pro Pro Ala Ser Leu Pro Gly Ser Leu Thr Asn Val Lys Ala Leu
    610                 615                 620

Gln Lys Ser Pro Gly Pro Gln Arg Glu Arg Lys Ser Ser Ser Ser Ser
625                 630                 635                 640

Glu Asp Arg Asn Arg Met Lys Thr Leu Gly Arg Arg Asp Ser Ser Asp
                645                 650                 655

Asp Trp Glu Ile Pro Asp Gly Gln Ile Thr Val Gly Gln Arg Ile Gly
            660                 665                 670

Ser Gly Ser Phe Gly Thr Val Tyr Lys Gly Lys Trp His Gly Asp Val
        675                 680                 685

Ala Val Lys Met Leu Asn Val Thr Ala Pro Thr Pro Gln Gln Leu Gln
    690                 695                 700

Ala Phe Lys Asn Glu Val Gly Val Leu Arg Lys Thr Arg His Val Asn
705                 710                 715                 720

Ile Leu Leu Phe Met Gly Tyr Ser Thr Lys Pro Gln Leu Ala Ile Val
                725                 730                 735

Thr Gln Trp Cys Glu Gly Ser Ser Leu Tyr His His Leu His Ile Ile
            740                 745                 750

Glu Thr Lys Phe Glu Met Ile Lys Leu Ile Asp Ile Ala Arg Gln Thr
        755                 760                 765

Ala Gln Gly Met Asp Tyr Leu His Ala Lys Ser Ile Ile His Arg Asp
    770                 775                 780

Leu Lys Ser Asn Asn Ile Phe Leu His Glu Asp Leu Thr Val Lys Ile
785                 790                 795                 800

Gly Asp Phe Gly Leu Ala Thr Val Lys Ser Arg Trp Ser Gly Ser His
                805                 810                 815

Gln Phe Glu Gln Leu Ser Gly Ser Ile Leu Trp Met Ala Pro Glu Val
            820                 825                 830

Ile Arg Met Gln Asp Lys Asn Pro Tyr Ser Phe Gln Ser Asp Val Tyr
        835                 840                 845

Ala Phe Gly Ile Val Leu Tyr Glu Leu Met Thr Gly Gln Leu Pro Tyr
    850                 855                 860

Ser Asn Ile Asn Asn Arg Asp Gln Ile Ile Phe Met Val Gly Arg Gly
865                 870                 875                 880
```

```
Tyr Leu Ser Pro Asp Leu Ser Lys Val Arg Ser Asn Cys Pro Lys Ala
                885                 890                 895

Met Lys Arg Leu Met Ala Glu Cys Leu Lys Lys Lys Arg Asp Glu Arg
            900                 905                 910

Pro Leu Phe Pro Gln Ile Leu Ala Ser Ile Glu Leu Leu Ala Arg Ser
        915                 920                 925

Leu Pro Lys Ile His Arg Ser Ala Ser Glu Pro Ser Leu Asn Arg Ala
    930                 935                 940

Gly Phe Gln Thr Glu Asp Phe Ser Leu Tyr Ala Cys Ala Ser Pro Lys
945                 950                 955                 960

Thr Pro Ile Gln Ala Gly Gly Tyr Gly Ala Phe Pro Val His
                965                 970
```

<210> SEQ ID NO 17
<211> LENGTH: 3853
<212> TYPE: DNA
<213> ORGANISM: Bos taurus

<400> SEQUENCE: 17

```
ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc    960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac taccctttcca tgtggctcat   1140

ccccttctgc accccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacacccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560
```

-continued

```
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
caggggggata tggtacgttt cctgttcact gaaacaaacc gagtgagtga cagcatgtag   2520
gagggtaggg acaaaagaaa gtgaacaaat gtttgcttat atatttgtta aattgaatag   2580
gattttcttt ttctttaaag gtgaacaaga gaacatgtgt gtttttaaag tttggatata   2640
gttttcttcc cagtctaaaa cccatagtta gcattacatt ttcaacatcg aatttttttt   2700
taattcatag acattgctga aaatttataa tacctttttcc agaggcttta cttcccattc   2760
caagtttgtt ttgtttactt ggttagtcta atcattaaac tttaaacttt ccccacctac   2820
cttttgctgt tagctatccc gcatccatta ggggctccaa gaacagcact gtctgcgtgt   2880
gtgtgttggc aggtgggaag ctgatggtaa gttaggctgt gttagtgaag gtaaactgac   2940
caggtctaat taggagtcac tagaattgaa taagcttatt tttattaata tttttttctta   3000
taactatttc tttttgtaat aatttagaaa atataattgt tctttattcc cttacagcag   3060
tataaattat tggtgcaggt aaccaaagat attactgagg agtggcatgt ttgacatgag   3120
tgacatggtt taactttgga tttttagtta atatttcttt atatattaag gatgtcttac   3180
acattataga agtcaaattt actgacaaag gtattgcctc ctcttcctcc ccaaaaacac   3240
agcaaaattc tctgggaact cgtagcattg ttggttttct tttggatgac tatggttgcc   3300
aaacaaccaa gtaattgatt ttttttaaat tattattgct ttagattata ctcacctctc   3360
atgatgcctg ttagcaatca cctttatcca tgtgtcttgt aaaatatctt tcctccttat   3420
attctttgcc caacaagagt ctacttgtta tgaatgagta ctattttctt tttttgattc   3480
cccagtataa ttagtatgtt tagtgctttc taggacttcc actttcttat gttaaaaaaa   3540
aaaacaaact aatgtggcag tcagtatatt cttactgtga atcagagtct ttactgggaa   3600
tcaaagtgaa agaagcagct gttctgactt cagagtcagc ctagggacca aaaccagcct   3660
cttaaataca ccttcattta ttcagtttgg atttgtgatg attttcatta tagctgacag   3720
ttcaaggtta ttcagtggca cacagatagc atctgcataa atgcctttct tcttgaaaat   3780
aaaggagaaa attgggaaga ctttacacca atagtttagt ctttaagtac cacagataac   3840
acacaccata aat                                                      3853
```

<210> SEQ ID NO 18
<211> LENGTH: 764
<212> TYPE: PRT
<213> ORGANISM: Bos taurus

<400> SEQUENCE: 18

```
Ala Ala Leu Ser Gly Gly Gly Gly Gly Gly Gly Gly Gly Ala Glu Gln
1               5                   10                  15

Gly Gln Ala Leu Phe Asn Gly Asp Met Glu Pro Glu Ala Gly Ala Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Ser Leu Ser Val
        115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Ile Pro Gln Glu Glu Ala Ser
    290                 295                 300

Leu Ala Glu Thr Thr Leu Pro Cys Gly Ser Ser Pro Ser Ala Pro Pro
305                 310                 315                 320

Ser Asp Ser Ile Gly Pro Pro Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365

Ile Asn Thr Ile Glu Pro Val Asn Ile Asp Asp Leu Ile Arg Asp Gln
    370                 375                 380
```

```
Gly Phe Arg Ser Asp Gly Gly Ser Thr Thr Gly Leu Ser Ala Thr Pro
385                 390                 395                 400

Pro Ala Ser Leu Pro Gly Ser Leu Ser Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
    530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Thr Phe Pro Val His
        755                 760
```

<210> SEQ ID NO 19
<211> LENGTH: 4936
<212> TYPE: DNA
<213> ORGANISM: Bos taurus

<400> SEQUENCE: 19
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttcccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg ggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aactttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc accccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatatttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaagt aggaaagact ctcctaagca 2340

```
agagacaaaa ttcagaagtt atcagggaaa aagataagca gattctcgcc tctattgagc   2400
tgctggcccg ctcattgcca aaaattcacc gcagtgcatc agaaccctcc ttgaatcggg   2460
ctggcttcca aacagaggat tttagtctat atgcttgtgc ttctccaaaa acacccattc   2520
aggcaggggg atatgaagca gatttggctc ttacatcaaa taaaaataga gtagaagttg   2580
ggatttagag atttcctgac atgcaagaag gaataagcaa gaaaaaaagg tttgttttcc   2640
ccaaatcata tctattgtct tttacttcta ttttttctta aatttttgt gatttcagag    2700
acatgtagag ttttattgat acctaaacta tgagttcttt tttttttttt tttttcatta   2760
ttttgatttt tttggccaag aggcatatgg gatcttagct tgagaaagca acaattttct   2820
tgatgtcatt ttgggtgagg gcacatattg ctgtgaacag tgtggtgata gccaccaggg   2880
accaaactca cacccgctgc attgaaaggt gaagtcttaa acactggacc agcagagaaa   2940
ttcctactct atgagttctt tttgtcatcc cctccccgca ccctccaccc ccaacctaaa   3000
gtctgatgat gaaatcaaca actattccat tagaagcagt agattctggt agcatgatct   3060
ttagtttgtt agtaagattt tgtgctttgt ggggttgtgt cgttttaagg ctaatattta   3120
agtttgtcaa atagaatgct gttcagattg taaaaatgag taataaacat ctgaagtttt   3180
ttttaagtta tttttaacat ggtatataca gttgagctta gagtttatca ttttctgata   3240
ttctcttact tagtagatga attctagcca ttttttataa agatttctgt taagcaaatc   3300
ctgttttcac atgggcttcc tttaagggat tttagattct gctggatatg gtgactgctc   3360
ataagactgt tgaaaattac ttttaagatg tattagaata cttctgaaaa aaaatagcaa   3420
ccttaaaacc ataagcaaaa gtagtaaggg tgtttataca tttctagagt ccctgtttag   3480
gtaatagcct cctatgattg tactttaaat gttttgctct ccaaggtttt agtaacttgg   3540
cttttttct aatcagtgcc aaactccccc agttttttta actttaaata tgaggtaata    3600
aatcttttac ccttccttga tcttttgact tataatacct tggtcagttg tttcttaaaa   3660
ggaatcctta aatggaaaga gacaatatca ctgtctgcag ttctgattag tagttttatt   3720
cagaatggaa aaacagatta ttcatttttg aaaattgttc aggggtatgt tcattgttag   3780
gaccttggac tttggagtca gtgcctagct atgcattcca ggtctgccat tttctggctg   3840
tgaaattttg gacaagttac ttaaccactt taaaccccag ctttaagaag taaattaacc   3900
ccagtaaatt aagaagtaat agcagccact tcgtagagtt gttatgaggc tcagatgcag   3960
tgcaaatgtg tataaagtat tcagggagtc acctggtata ctataataga cactagaata   4020
gttgccaata ttatcagcat acaatctgag gattctgtca gccaatcatt agcaatctgt   4080
tgtttgttgg gacatgccag tgttctccag ttgaaatcag tagcaatcta aaaatggata   4140
gattattcct catttaaata gtgtgttcat ataagtgatt gcttggatcc ttatcagaag   4200
ttgctgttac tgaaaaatga taaggctgac taaattgtga tagttgtcag ttactaacca   4260
actcccagaa atgaataaga ggaacctatc tctagttcct agtagaaggt atggacaaaa   4320
tagtaggtga aaaataatgt cttgaacccc caaattaagt aagctttaaa gagtacaata   4380
cctcaaaggg tctttgcggt ttaaaatttg tatgctgaga atgatgttca ttgacatgtg   4440
cctatatgta attttttgat agtttaaaag gtgaaatgaa ctacagatgg gagaggtctg   4500
aattttcttg ccttcagtca aatgtgtaat gtggacatat tatttgacct gtgaatttta   4560
tcttttaaaa aagattaatt cctgcttctt ccttcctaat agttgcatta taataatgaa   4620
aatgagttga taatttgggg ggaaagtatt ctacaaatca accttattat tttaccattg   4680
gtttctgaga aattttgttc atttgaaccg tttatagctt gattagaatc atagcatgta   4740
```

-continued

```
aaacccaact gagggattat ctgcagactt aatgtagtat tatgtaagtt gtcttctttc   4800

atttcgacct tttttgcttt tgttgttgct agatctgtag tatgtagcta gtcacctttc   4860

agcgaggttt cagcgaggct tttctgtgtc tctaggttat ttgagataac ttttttaaaa   4920

ttagctcttg tcctcc                                                    4936


<210> SEQ ID NO 20
<211> LENGTH: 797
<212> TYPE: PRT
<213> ORGANISM: Bos taurus

<400> SEQUENCE: 20

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335
```

-continued

```
Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750
```

-continued

```
Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Glu Ala Asp Leu
    770                 775                 780

Ala Leu Thr Ser Asn Lys Asn Arg Val Glu Val Gly Ile
785                 790                 795
```

```
<210> SEQ ID NO 21
<211> LENGTH: 4154
<212> TYPE: DNA
<213> ORGANISM: Bos taurus

<400> SEQUENCE: 21

ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc     960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac tacccttcca tgtggctcat   1140

ccccttctgc acccccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacaccccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560

tcacagtggg acaaagaatt ggatcagggt catttgggac agtctacaag ggaaagtggc   1620

atggtgatgt ggcagtgaaa atgttgaatg tgacagcacc cacacctcag cagttacagg   1680

ccttcaaaaa tgaagtagga gtactcagga aaacgcgaca tgtgaatatc ctcctcttca   1740

tgggttattc aacaaagcca caactggcta ttgttaccca gtggtgtgag ggctccagtt   1800

tatatcatca tctccacatc attgagacca aattcgagat gatcaaactt atagatattg   1860
```

-continued

```
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaagt aggaaagact ctcctaagca   2340
agagacaaaa ttcagaagtt atcagggaaa aagataagca gattctcgcc tctattgagc   2400
tgctggcccg ctcattgcca aaaattcacc gcagtgcatc agaaccctcc ttgaatcggg   2460
ctggcttcca aacagaggat tttagtctat atgcttgtgc ttctccaaaa acacccattc   2520
aggcaggggg atatggctga gcacattgtc catcacccac aagtggctgg ttctcatcgc   2580
agaatctacg tagggaatcg ggcgtgaaat tcacttaaga gatagagcag aggaagtgtt   2640
ctgtttacag gaatggagat gagagttatg agtaagttgc ttagtcagtt ggctttgttt   2700
tgaaaattat tgtgttatat ttgtgttaac ctacttgtgt tttgacagta tatgtcacat   2760
aggaagaaac ctcagactag cataataaca aagctcagac taggcacaga tgtacacaga   2820
atggaccaaa atgggatggg ggaaggtatg ggaataagtc taggggtagg gaaaaattga   2880
tgtgagggtg ggaaataaac tgtaattacc tgaaataaaa tgtaagagtg caataagtgt   2940
gctttttatt ctaagctgtg aatgggtttt ttaaaaaaag cattccttcc caatgcattt   3000
gcctatgttc catagctgat taaaaccagc tatataaaca tatgcctttt tattcatgtt   3060
aattaccaat ataaatggct aacctttacg tcttatttat cttcatgtta tgttagttta   3120
catacaggga tgtgtgtgtg tgtgtatgct ataaattttc cctccttcgt ttaaaaacgc   3180
gtttgttgga tcctctctgt ttccttaggc catgccacag ctcatagtct cagcttggcc   3240
ttcctgtcac ctgatctgaa ggactatcac agtgacgtag ctcgttcatt ggttgtacac   3300
actctaaccc ttttccttgc tcagcaatta ctgtgtcttc taaaacagga gtgtacaacc   3360
atgagattgc aattaattgt ttgacatatg tccctttgaa ttctatttat tagttatgat   3420
tgattgctct ttggtttgga ccaagaaaaa cgaaatccca cctccccacc ttttcactta   3480
tttcttactt tgaggacaat tctgtaagag agaggaaagg gaactccttc atgttttaac   3540
tgcagcaagt taatggccct ggtttacacc aaacattatg gtgattcaca ttcacattcc   3600
tctcctctct tgctgccaga ggtttgggtt ttgttcagtt ctgctcaagc actgaaaaag   3660
ttttcatgga gtctggagag tgcccagtga aaagatggtt tttaattgtc cacagacctt   3720
tctgttcctg ctttgcaaaa attacaaagg agtaactatt tttaaagctt atttttcaat   3780
tcataaaaaa gacatttatt ttcagtcaga tgatgtctcc ttgtccctta atcctcaatg   3840
tttgcttgaa tcttttttt ttttctgatt ttctcccatc cccacttctt gatacttctt   3900
gagttctctt tcctgctcag gtcctttcat ttgtactttg gagtttttc tcatgtaaat   3960
ttgtacaatg gaaaatattg ttcagtttgg atagaacgca tggagaatta aataaaaaag   4020
atagctgaaa ttcagattga aatttatttg tgtaaagtta tttaaaaact ctgtactata   4080
taaaaggcaa aaaaagttct atgtacttga tgtgaatatg cgaatactgc tataataaag   4140
attgactgca tgga                                                     4154
```

```
<210> SEQ ID NO 22
<211> LENGTH: 781
<212> TYPE: PRT
<213> ORGANISM: Bos taurus

<400> SEQUENCE: 22

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380
```

-continued

```
Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
            740                 745                 750

Leu Asn Arg Ala Gly Phe Gln Thr Glu Asp Phe Ser Leu Tyr Ala Cys
        755                 760                 765

Ala Ser Pro Lys Thr Pro Ile Gln Ala Gly Gly Tyr Gly
    770                 775                 780
```

<210> SEQ ID NO 23
<211> LENGTH: 7914
<212> TYPE: DNA

<213> ORGANISM: Bos taurus

<400> SEQUENCE: 23
ctcagctgcg ccgggtctca caagacggtt cccgaggtgg cccaggcgcc gtcccaccgc 60
cgacgccgcc cgggccgccc gggccgtccc tccccgctgc cccccgtcct ccgcctccgc 120
ctccccccgc cctcagcctc ccttccccct ccccgcccag cagcggtcgc tcgggcccgg 180
ctctcggtta taagatggcg gcgctgagtg gcggcggcgg cggcggcggc ggtggcgcgg 240
agcagggcca ggctctgttc aacggggaca tggagcccga ggccggcgcc gcggcctctt 300
cggctgcgga ccccgccatt cccgaggagg tgtggaatat caaacaaatg attaagttga 360
cacaggagca tatagaggcc ctattggaca aatttggtgg ggagcataat ccaccatcaa 420
tatatctgga ggcctatgaa gaatacacca gcaagctaga tgccctccaa caaagagaac 480
aacagttatt ggaatccctg gggaatggaa ctgatttttc tgtttctagc tctgcatcaa 540
cggacaccgt tacatcttct tcctcttcta gcctttcagt gctgccttca tctctttcag 600
tttttcaaaa tcccacagat gtgtcacgga gcaaccccaa gtcaccacaa aaacctatcg 660
ttagagtctt cctgcccaat aaacagagga cagtggtacc tgcacggtgt ggagtcacag 720
tccgggacag cctgaagaag gcactgatga tgagaggtct aatcccagag tgctgtgctg 780
tttacagaat tcaggatggg gagaagaaac caattggctg ggacactgat atttcctggc 840
ttactggaga ggagttgcat gtagaagtgt tggagaatgt tccacttaca acacacaact 900
ttgtacggaa aacttttttc accttagcat tttgtgactt ctgtagaaag ctgcttttcc 960
agggattccg ctgtcaaaca tgtggttata aatttcacca gcgttgtagt acagaggttc 1020
cactgatgtg tgttaattat gaccaactag atttgctgtt tgtctccaag ttctttgaac 1080
accacccaat accacaggag gaggcctcct tagcagagac tacccttcca tgtggctcat 1140
ccccttctgc acccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacacccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280

-continued

```
taaaaaagaa aagagatgaa agaccactct ttccccaaat tctcgcctct attgagctgc   2340
tggcccgctc attgccaaaa attcaccgca gtgcatcaga accctccttg aatcgggctg   2400
gcttccaaac agaggatttt agtctatatg cttgtgcttc tccaaaaaca cccattcagg   2460
caggggggata tggagaattt gcagccttca agtagccaca ccatcatgac agcatctact   2520
cttatttctt aagtcttgtg ttcgtacaat ttgttaacat caaaacacag ttctgttcct   2580
caactctttt taaagttaaa atttttcagt gcataagctg gtgtggaaca gaaggaaatt   2640
tcccatccaa caaaagaggg aagaatgttt taggaaccag aattctctgc tgccagtgtt   2700
tcttcttcaa cacaaatatc acaagtctgc ccactcccag gaagaaagag gagagaccct   2760
gagttctgac cttttgatgg tcaggcatga tggaaagaaa ctgctgctac agcttgggag   2820
atttgctctg ggaagtctgc cagtcaactt tgcccttcta accaccagat caatatgtgg   2880
ctgatcatct gatggggcag ttgcaatcac caagccttgt tctctttcct gttctgggat   2940
tgtgttgtgg aacccttttc cctagccacc accagttcat ttctgaggga tggaacaaaa   3000
atgcagcatg cccttcctgt gtggtgcatg ttcagtcctt gacaaatttt taccaaaatg   3060
aagctacttt atttaaaagg agggtgagag gtgaggaggt cactttgggt gtggcggaaa   3120
gggaatgctg catctttttc ctgggctgct ggggctctgg ccttggcttg ccagccggaa   3180
gcgctggcac gcatcgcctt cttttcccat tgggtccagc aatgaagacg agtgtttggg   3240
gtttttttttt tctccaccat gtagcaagtt ctcaggaaaa tacaattgat atcttcctcc   3300
taagctcttc caatcagtca ccaagtactt atgtggttac tttgtccagg gcacaaaatg   3360
cctgtatcta attaaaagcc tacaaaactg cttgataaca gttttgaatg tgagacattt   3420
atgtaattta aatgtaaggt acaagtttta atttctgagt ttcttctatt atatttttat   3480
taaaaaaaga aaataatttt cagattgaat tggagtaaaa taatattact tcccactaga   3540
attatatatc ctggaaaatt gtatttttgt tacataagca gcttttaaag aaagatcatt   3600
acccttttct ctacataaat atatggggag tcttagccta atgacaaata tttataattt   3660
ttaaattaat ggtacttgct ggatccatac taacatcttt actaatacct cattgtttct   3720
tccaacttac tcctacacta catcctacat cttcttccta gtcttttatc tagaatatgc   3780
aacctcaaat aaaaatggtg gtgtcctcat tcattctcct ccttcctttt ttcccaagcc   3840
tgatcttcaa aaggttggtt aatttggcag ctgagttcct ccccaggcag agaatagacc   3900
aattttaggt gtattgggac tgagggagga tgtgtaaaga ttaacatcag taaagaaccg   3960
ctgtggagta attaagaact ttgttcttta taactggaga atataaccta accctaacat   4020
ccctcagcct ttactaaagt gtggcgtaaa tcacagtagt agcaaagaaa gtgactctgg   4080
atgtgttcct ggccagtacc tcccttatca tgaatgtaga ctctctcatc aagatttagg   4140
aatataaatc aaatcaaatg tgcccagcca agctatgtag taagggactt gaacaatatt   4200
aggcagaacc tataaaataa atcagggaat tagaaattat ttaaagtttt caaattgtaa   4260
attgccccgg tgtctttcag cctactgcca ttatttttgc tacaatacct acatttcaga   4320
ggagggccta ctgaaaattc catgcaagtg gaaaataatc ctcaagttat taatgagttt   4380
gaaaagcaat gagttcttaa gtctttgtga gtagagcaag atcctacaaa attcagaaat   4440
agtaaaaatg gattcatgct gatttgaaga gcatctgtgt gcataatata atgctgcatc   4500
tcttttaaaa gcagtctatt tttcttttta aatttgtccc catagatgct tttgaacatg   4560
aacatgctta tgttaccttt tccgaggttg ggaagagcca ggagctctca ggcagggccc   4620
```

-continued

```
cctccctcag ctgggcagga gctgctcagg aggagctagt tatagaggaa gcttagcgtt   4680
ggcattttca aaattcaagg tgataacgct ttcttcttcc tttctgtttt agaatagatt   4740
gctgtctgat ttgaaaaagg gaaatagatt tgatctcaaa tgaatctgtg cccagaagcc   4800
aggctcaggg tattcagaga tttgtatagt gccctcaaaa aataacaaaa ttttagcttt   4860
ccttttttct tcttttctcc atcaaattct tttttctcta gtttacaaat gacatggaaa   4920
aggaatttcc cctgagtttt gtatgccttt ttttttttgg cttagactat agataggcgt   4980
gttgagctcc taagaaaata caaggaggaa ctctttgttg tgcagagcac tttatgagta   5040
gtttgtgtgg ataatatgtg actgcttccc tgacgagctt gtgaggctgt acttatgtct   5100
ttcctgtaag gcagcttcag tgccttctgt agtgtatata aggaaagatt acgccttctg   5160
aaaaatctca gagcaaccat aagattattt taaaatatgt agtatgactg atggactttt   5220
tcatcattaa attagtctag catctaaact tttaccactg aaataatatt gaccaaaaag   5280
caatttataa aaggtatttg tgaatagaaa atacaatgtg atcatttgta cttatgtgca   5340
ccttaaaaga ggaattctgt ctagctgtca aattctggtt ccttaacatc cagtccttga   5400
ttgtgattga gatctggtag gacgtgctgg ggcacgctag cagataaaat cccgtatact   5460
ttaggataga tgttacattt atgtcagtgt tggcaaagag cattgtgtag taataaagaa   5520
ttcaagactt cagcaatgtc aacctgaaac tttgtaaata tttcctagat tgttatttga   5580
tgcagtcaca gctctttatc acacaatgtt gtctttccct catcaggcaa ttttagaact   5640
gctgcacacc cctcctcaga tctcacctgc ccctcctgta cattcacctc tccagccttg   5700
tgcacacctc atttagcttt agtttgaaac acattgcagg gttcaggtga cctcttcaaa   5760
aactacctcc tcagaatgag gtaatgaata gttatttatt ttaaaatatg aaaagtcagg   5820
agctctagaa tatgaagatg atctaagatt ttaactttta tgtatacttg ttgagcactc   5880
tccttttgtc ctaaagggca ttatacattt aagcagtaat actgaaaaat gtagctcaga   5940
gtaactgaat gttgttgaaa gtggtgccag aatctgtttt aggggtacgt atcagaatct   6000
taatcttaaa tcggttacat gaaattaaat agttaatggt aacacttgac taacagatat   6060
aattttaatt ttcggtaggc ttttagcaag acagtaagta catcttcata atgagttagc   6120
cacagcttca tcacatgcac agattttcct gttgagagac tgcccagtta agagggtaga   6180
atgatgaacc atttttcagg attctcttct ttgtccaaac tggcattgtg agtgctagaa   6240
tatcagcact ttcaaactag tgattccaac tattaggcta ttaaaaagca aaacaaacca   6300
aacaaaccat agccagacat gggaagttta ctatgagtat aaacagcaaa tagcttacag   6360
gtcatacatt gaaatggtgt aggtaaggcg ttagaaaaat accttgacaa tttgccaaat   6420
gatcttactg tgccttcatg atgcaataaa aaaaaaaaaa atttagcata aatcagtgat   6480
ttgtgaagag agcagccacc ctggtctaac tcagctgtgt taatattttt tagcgtgcaa   6540
tttagactgc aaagataaat gcactaaaga gtttatagcc aaaatcacat ttaaaaaatg   6600
agagaaaaca caggtaaatt ttcagtgaac aaaattattt ttttaaagta cataatccct   6660
agtatagtca gatatattta tcacatagag caaataggtt gaaatcacaa ttcagtgaca   6720
tttctagaga aactttttct actcccatag gttcttcaaa gcatggaact tttatataac   6780
agaaatgtgt gacggtcatt ttaaattgct gtagtttggg gctgaagtac tgtgtgctgg   6840
gcagcaatca catgtattaa ctagtgagaa aggagaaatt aagatatagg acagaatttg   6900
attttcttgt tcccagatta ctgctgccaa cctagacact gagtttccag aggctgaaac   6960
gtaaacttgc agctcagcaa ctgttttgca aagttagtgg gactgtcctg cttatgctgt   7020
```

-continued tcaaaaatgc tctgagggcc aggtggggcc tccaggggct cctctctgag gggacatcag 7080
actagctaac gacctggcgg gcggatgtga accggacaca ctccatggtg tgcttcttgt 7140
atcggtccct cgccaccctc aagaaaggct tcagcgggtt ctctagacgt ctccactaag 7200
gtgtgttact aacagccatg ggttgttgag cacccgagga gtgcaatagc atctctgcat 7260
gattgtatat tggcccgaag agaatgaagt ggccagtgta ctcatgttcc atgttgctag 7320
ctctggtaaa ctgaaaatac tggtaagatt tttgttttat cagtacacta gagagtaagc 7380
tttgttttgt tgtttttaga taatgttttc acttccattt ggaaagacat ttaaattgag 7440
tttcagtcct aaattttgcc agtcatggta attagcagtt tctatcaggt atttttaagg 7500
tagaagagga tagaaacata agttctaaaa gcttaaggta accgtggttt attttaaaat 7560
gtttaggggt ggttagtctc tacctcaaaa aaagtgagtg aatcttttat ttcagcattc 7620
acaagttcgg ctgttgtttt tgtaatacat ttttttttta accttttgac ccccctttac 7680
ctaagtgtca atgtagtttt attaattact aagtcagttt cattaaaatg tttatttagc 7740
agttttgact aattgcaatg attaatatag ccagttgtgc atgaggacac agccagtgag 7800
tatatctggg tttttttgt gatgcttttt ttcttaagac ttctgtagat ttatgaagta 7860
ctcattgaaa acaactaaaa tacgtttatt cgtgttaata tggaaaaaaa aaaa 7914

<210> SEQ ID NO 24
<211> LENGTH: 766
<212> TYPE: PRT
<213> ORGANISM: Bos taurus

<400> SEQUENCE: 24

Met Ala Ala Leu Ser Gly Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser
130 135 140

Arg Ser Asn Pro Lys Ser Pro Gln Lys Pro Ile Val Arg Val Phe Leu
145 150 155 160

Pro Asn Lys Gln Arg Thr Val Val Pro Ala Arg Cys Gly Val Thr Val
165 170 175

Arg Asp Ser Leu Lys Lys Ala Leu Met Met Arg Gly Leu Ile Pro Glu
180 185 190

Cys Cys Ala Val Tyr Arg Ile Gln Asp Gly Glu Lys Lys Pro Ile Gly
195 200 205

Trp Asp Thr Asp Ile Ser Trp Leu Thr Gly Glu Glu Leu His Val Glu

-continued

```
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640
```

```
Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Glu Phe Ala Ala Phe Lys
        755                 760                 765


<210> SEQ ID NO 25
<211> LENGTH: 4670
<212> TYPE: DNA
<213> ORGANISM: Bos taurus

<400> SEQUENCE: 25

ggtgtgtcat agtgcagcag attgaatgca gaagatatga aaattcagat gtcttctgtt      60

aaggtgtgga atatcaaaca aatgattaag ttgacacagg agcatataga ggccctattg     120

gacaaatttg gtggggagca taatccacca tcaatatatc tggaggccta tgaagaatac     180

accagcaagc tagatgccct ccaacaaaga gaacaacagt tattggaatc cctggggaat     240

ggaactgatt tttctgtttc tagctctgca tcaacggaca ccgttacatc ttcttcctct     300

tctagccttt cagtgctgcc ttcatctctt tcagtttttc aaaatcccac agatgtgtca     360

cggagcaacc ccaagtcacc acaaaaacct atcgttagag tcttcctgcc caataaacag     420

aggacagtgg tacctgcacg gtgtggagtc acagtccggg acagcctgaa gaaggcactg     480

atgatgagag gtctaatccc agagtgctgt gctgtttaca gaattcagga tggggagaag     540

aaaccaattg gctgggacac tgatatttcc tggcttactg gagaggagtt gcatgtagaa     600

gtgttggaga atgttccact tacaacacac aactttgtac ggaaaacttt tttcacctta     660

gcattttgtg acttctgtag aaagctgctt ttccagggat tccgctgtca aacatgtggt     720

tataaatttc accagcgttg tagtacagag gttccactga tgtgtgttaa ttatgaccaa     780

ctagatttgc tgtttgtctc caagttcttt gaacaccacc caataccaca ggaggaggcc     840

tccttagcag agactaccct tccatgtggc tcatcccctt ctgcaccccc ctccgattct     900

attgggcccc caattctcac cagtccatct ccttcaaaat ccattccaat tccacagcct     960

ttccgaccag cagatgaaga tcatcgaaat cagtttggac aacgagaccg gtcctcatca    1020

gctccaaatg tgcatataaa cacaatagaa cccgtcaata ttgatgactt gattagagac    1080

caagggtttc gtagtgatgg aggatcaacc acaggtttat ccgccacacc ccctgcctca    1140

ttacctggct cactctctaa tgtgaaagca ttgcagaaat ctccaggacc tcagcgagaa    1200

agaaagtcct cttcatcctc agaagacagg aatcgaatga aaacgcttgg tagacgggat    1260

tcaagtgacg attgggagat tcctgatgga cagatcacag tgggacaaag aattggatca    1320

gggtcatttg ggacagtcta caagggaaag tggcatggtg atgtggcagt gaaaatgttg    1380
```

-continued

```
aatgtgacag cacccacacc tcagcagtta caggccttca aaaatgaagt aggagtactc   1440
aggaaaacgc gacatgtgaa tatcctcctc ttcatgggtt attcaacaaa gccacaactg   1500
gctattgtta cccagtggtg tgagggctcc agtttatatc atcatctcca catcattgag   1560
accaaattcg agatgatcaa acttatagat attgcacggc agactgcaca gggcatggat   1620
tacttacacg ccaagtcaat catccacaga gacctcaaga gtaataatat ttttcttcat   1680
gaagacctca cagtaaaaat aggtgatttt ggtctagcca cagtgaaatc tcgatggagt   1740
gggtcccatc agtttgaaca gttgtctgga tccattttgt ggatggcacc agaagtaatc   1800
agaatgcaag ataaaaaccc atatagcttt cagtcagatg tatatgcatt tgggattgtt   1860
ctgtatgaat tgatgaccgg acagttacct tattcaaata tcaacaacag ggaccagata   1920
atttttatgg tgggacgagg atatctgtct ccagatctca gtaaggtacg gagtaactgt   1980
ccaaaagcca tgaagagatt aatggcagag tgcctaaaaa agaaaagaga tgaaagacca   2040
ctctttcccc aagtaggaaa gactctccta agcaagagac aaaattcaga agttatcagg   2100
gaaaaagata agcagattct cgcctctatt gagctgctgg cccgctcatt gccaaaaatt   2160
caccgcagtg catcagaacc ctccttgaat cgggctggct tccaaacaga ggattttagt   2220
ctatatgctt gtgcttctcc aaaaacaccc attcaggcag gggatatga agcagatttg   2280
gctcttacat caaataaaaa tagagtagaa gttgggattt agagatttcc tgacatgcaa   2340
gaaggaataa gcaagaaaaa aaggtttgtt ttccccaaat catatctatt gtcttttact   2400
tctatttttt cttaaatttt ttgtgatttc agagacatgt agagttttat tgatacctaa   2460
actatgagtt cttttttttt tttttttttc attattttga tttttttggc caagaggcat   2520
atgggatctt agcttgagaa agcaacaatt ttcttgatgt cattttgggt gagggcacat   2580
attgctgtga acagtgtggt gatagccacc agggaccaaa ctcacacccg ctgcattgaa   2640
aggtgaagtc ttaaacactg gaccagcaga gaaattccta ctctatgagt tctttttgtc   2700
atcccctccc cgcaccctcc acccccaacc taaagtctga tgatgaaatc aacaactatt   2760
ccattagaag cagtagattc tggtagcatg atctttagtt tgttagtaag attttgtgct   2820
ttgtggggtt gtgtcgtttt aaggctaata tttaagtttg tcaaatagaa tgctgttcag   2880
attgtaaaaa tgagtaataa acatctgaag tttttttaa gttattttta acatggtata   2940
tacagttgag cttagagttt atcattttct gatattctct tacttagtag atgaattcta   3000
gccatttttt ataaagattt ctgttaagca aatcctgttt tcacatgggc ttcctttaag   3060
ggattttaga ttctgctgga tatggtgact gctcataaga ctgttgaaaa ttacttttaa   3120
gatgtattag aatacttctg aaaaaaaata gcaaccttaa aaccataagc aaaagtagta   3180
agggtgttta tacatttcta gagtccctgt ttaggtaata gcctcctatg attgtacttt   3240
aaatgttttg ctctccaagg ttttagtaac ttggcttttt ttctaatcag tgccaaactc   3300
ccccagtttt tttaacttta aatatgaggt aataaatctt ttacccttcc ttgatctttt   3360
gacttataat accttggtca gttgtttctt aaaaggaatc cttaaatgga aagagacaat   3420
atcactgtct gcagttctga ttagtagttt tattcagaat ggaaaaacag attattcatt   3480
tttgaaaatt gttcaggggt atgttcattg ttaggacctt ggactttgga gtcagtgcct   3540
agctatgcat tccaggtctg ccattttctg gctgtgaaat tttggacaag ttacttaacc   3600
actttaaacc ccagctttaa gaagtaaatt aaccccagta aattaagaag taatagcagc   3660
cacttcgtag agttgttatg aggctcagat gcagtgcaaa tgtgtataaa gtattcaggg   3720
agtcacctgg tatactataa tagacactag aatagttgcc aatattatca gcatacaatc   3780
```

-continued

```
tgaggattct gtcagccaat cattagcaat ctgttgtttg ttgggacatg ccagtgttct   3840

ccagttgaaa tcagtagcaa tctaaaaatg gatagattat tcctcattta aatagtgtgt   3900

tcatataagt gattgcttgg atccttatca gaagttgctg ttactgaaaa atgataaggc   3960

tgactaaatt gtgatagttg tcagttacta accaactccc agaaatgaat aagaggaacc   4020

tatctctagt tcctagtaga aggtatggac aaaatagtag gtgaaaaata atgtcttgaa   4080

cccccaaatt aagtaagctt taaagagtac aatacctcaa agggtctttg cggtttaaaa   4140

tttgtatgct gagaatgatg ttcattgaca tgtgcctata tgtaattttt tgatagttta   4200

aaaggtgaaa tgaactacag atgggagagg tctgaatttt cttgccttca gtcaaatgtg   4260

taatgtggac atattatttg acctgtgaat tttatctttt aaaaaagatt aattcctgct   4320

tcttccttcc taatagttgc attataataa tgaaaatgag ttgataattt ggggggaaag   4380

tattctacaa atcaacctta ttattttacc attggtttct gagaaatttt gttcatttga   4440

accgtttata gcttgattag aatcatagca tgtaaaaccc aactgaggga ttatctgcag   4500

acttaatgta gtattatgta agttgtcttc tttcatttcg acctttttg cttttgttgt   4560

tgctagatct gtagtatgta gctagtcacc tttcagcgag gtttcagcga ggcttttctg   4620

tgtctctagg ttatttgaga taactttttt aaaattagct cttgtcctcc              4670
```

<210> SEQ ID NO 26
<211> LENGTH: 761
<212> TYPE: PRT
<213> ORGANISM: Bos taurus

<400> SEQUENCE: 26

```
Met Lys Ile Gln Met Ser Ser Val Lys Val Trp Asn Ile Lys Gln Met
1               5                   10                  15

Ile Lys Leu Thr Gln Glu His Ile Glu Ala Leu Leu Asp Lys Phe Gly
            20                  25                  30

Gly Glu His Asn Pro Pro Ser Ile Tyr Leu Glu Ala Tyr Glu Glu Tyr
        35                  40                  45

Thr Ser Lys Leu Asp Ala Leu Gln Gln Arg Glu Gln Gln Leu Leu Glu
    50                  55                  60

Ser Leu Gly Asn Gly Thr Asp Phe Ser Val Ser Ser Ser Ala Ser Thr
65                  70                  75                  80

Asp Thr Val Thr Ser Ser Ser Ser Ser Ser Leu Ser Val Leu Pro Ser
                85                  90                  95

Ser Leu Ser Val Phe Gln Asn Pro Thr Asp Val Ser Arg Ser Asn Pro
            100                 105                 110

Lys Ser Pro Gln Lys Pro Ile Val Arg Val Phe Leu Pro Asn Lys Gln
        115                 120                 125

Arg Thr Val Val Pro Ala Arg Cys Gly Val Thr Val Arg Asp Ser Leu
    130                 135                 140

Lys Lys Ala Leu Met Met Arg Gly Leu Ile Pro Glu Cys Cys Ala Val
145                 150                 155                 160

Tyr Arg Ile Gln Asp Gly Glu Lys Lys Pro Ile Gly Trp Asp Thr Asp
                165                 170                 175

Ile Ser Trp Leu Thr Gly Glu Glu Leu His Val Glu Val Leu Glu Asn
            180                 185                 190

Val Pro Leu Thr Thr His Asn Phe Val Arg Lys Thr Phe Phe Thr Leu
        195                 200                 205

Ala Phe Cys Asp Phe Cys Arg Lys Leu Leu Phe Gln Gly Phe Arg Cys
```

```
    210                 215                 220

Gln Thr Cys Gly Tyr Lys Phe His Gln Arg Cys Ser Thr Glu Val Pro
225                 230                 235                 240

Leu Met Cys Val Asn Tyr Asp Gln Leu Asp Leu Leu Phe Val Ser Lys
                245                 250                 255

Phe Phe Glu His His Pro Ile Pro Gln Glu Glu Ala Ser Leu Ala Glu
            260                 265                 270

Thr Thr Leu Pro Cys Gly Ser Ser Pro Ser Ala Pro Pro Ser Asp Ser
        275                 280                 285

Ile Gly Pro Pro Ile Leu Thr Ser Pro Ser Pro Ser Lys Ser Ile Pro
    290                 295                 300

Ile Pro Gln Pro Phe Arg Pro Ala Asp Glu Asp His Arg Asn Gln Phe
305                 310                 315                 320

Gly Gln Arg Asp Arg Ser Ser Ser Ala Pro Asn Val His Ile Asn Thr
                325                 330                 335

Ile Glu Pro Val Asn Ile Asp Asp Leu Ile Arg Asp Gln Gly Phe Arg
            340                 345                 350

Ser Asp Gly Gly Ser Thr Thr Gly Leu Ser Ala Thr Pro Pro Ala Ser
        355                 360                 365

Leu Pro Gly Ser Leu Ser Asn Val Lys Ala Leu Gln Lys Ser Pro Gly
    370                 375                 380

Pro Gln Arg Glu Arg Lys Ser Ser Ser Ser Ser Glu Asp Arg Asn Arg
385                 390                 395                 400

Met Lys Thr Leu Gly Arg Arg Asp Ser Ser Asp Asp Trp Glu Ile Pro
                405                 410                 415

Asp Gly Gln Ile Thr Val Gly Gln Arg Ile Gly Ser Gly Ser Phe Gly
            420                 425                 430

Thr Val Tyr Lys Gly Lys Trp His Gly Asp Val Ala Val Lys Met Leu
        435                 440                 445

Asn Val Thr Ala Pro Thr Pro Gln Gln Leu Gln Ala Phe Lys Asn Glu
    450                 455                 460

Val Gly Val Leu Arg Lys Thr Arg His Val Asn Ile Leu Leu Phe Met
465                 470                 475                 480

Gly Tyr Ser Thr Lys Pro Gln Leu Ala Ile Val Thr Gln Trp Cys Glu
                485                 490                 495

Gly Ser Ser Leu Tyr His His Leu His Ile Ile Glu Thr Lys Phe Glu
            500                 505                 510

Met Ile Lys Leu Ile Asp Ile Ala Arg Gln Thr Ala Gln Gly Met Asp
        515                 520                 525

Tyr Leu His Ala Lys Ser Ile Ile His Arg Asp Leu Lys Ser Asn Asn
    530                 535                 540

Ile Phe Leu His Glu Asp Leu Thr Val Lys Ile Gly Asp Phe Gly Leu
545                 550                 555                 560

Ala Thr Val Lys Ser Arg Trp Ser Gly Ser His Gln Phe Glu Gln Leu
                565                 570                 575

Ser Gly Ser Ile Leu Trp Met Ala Pro Glu Val Ile Arg Met Gln Asp
            580                 585                 590

Lys Asn Pro Tyr Ser Phe Gln Ser Asp Val Tyr Ala Phe Gly Ile Val
        595                 600                 605

Leu Tyr Glu Leu Met Thr Gly Gln Leu Pro Tyr Ser Asn Ile Asn Asn
    610                 615                 620

Arg Asp Gln Ile Ile Phe Met Val Gly Arg Gly Tyr Leu Ser Pro Asp
625                 630                 635                 640
```

-continued

```
Leu Ser Lys Val Arg Ser Asn Cys Pro Lys Ala Met Lys Arg Leu Met
                645                 650                 655

Ala Glu Cys Leu Lys Lys Lys Arg Asp Glu Arg Pro Leu Phe Pro Gln
            660                 665                 670

Val Gly Lys Thr Leu Leu Ser Lys Arg Gln Asn Ser Glu Val Ile Arg
        675                 680                 685

Glu Lys Asp Lys Gln Ile Leu Ala Ser Ile Glu Leu Leu Ala Arg Ser
    690                 695                 700

Leu Pro Lys Ile His Arg Ser Ala Ser Glu Pro Ser Leu Asn Arg Ala
705                 710                 715                 720

Gly Phe Gln Thr Glu Asp Phe Ser Leu Tyr Ala Cys Ala Ser Pro Lys
                725                 730                 735

Thr Pro Ile Gln Ala Gly Gly Tyr Glu Ala Asp Leu Ala Leu Thr Ser
            740                 745                 750

Asn Lys Asn Arg Val Glu Val Gly Ile
        755                 760
```

<210> SEQ ID NO 27
<211> LENGTH: 4816
<212> TYPE: DNA
<213> ORGANISM: Bos taurus

<400> SEQUENCE: 27

```
ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctccccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc    960

agggattccg ctgtcaaaca tgtggttata aatttcacca gcgttgtagt acagaggttc   1020

cactgatgtg tgttaattat gaccaactag agcccccaat tctcaccagt ccatctcctt   1080

caaaatccat tccaattcca cagcctttcc gaccagcaga tgaagatcat cgaaatcagt   1140

ttggacaacg agaccggtcc tcatcagctc caaatgtgca tataaacaca atagaacccg   1200

tcaatattga tgacttgatt agagaccaag ggtttcgtag tgatggagga tcaaccacag   1260

gtttatccgc cacacccct gcctcattac ctggctcact ctctaatgtg aaagcattgc   1320

agaaatctcc aggacctcag cgagaaagaa agtcctcttc atcctcagaa gacaggaatc   1380
```

```
gaatgaaaac gcttggtaga cgggattcaa gtgacgattg ggagattcct gatggacaga   1440
tcacagtggg acaaagaatt ggatcagggt catttgggac agtctacaag ggaaagtggc   1500
atggtgatgt ggcagtgaaa atgttgaatg tgacagcacc cacacctcag cagttacagg   1560
ccttcaaaaa tgaagtagga gtactcagga aaacgcgaca tgtgaatatc ctcctcttca   1620
tgggttattc aacaaagcca caactggcta ttgttaccca gtggtgtgag ggctccagtt   1680
tatatcatca tctccacatc attgagacca aattcgagat gatcaaactt atagatattg   1740
cacggcagac tgcacagggc atggattact tacacgccaa gtcaatcatc cacagagacc   1800
tcaagagtaa taatattttt cttcatgaag acctcacagt aaaaataggt gattttggtc   1860
tagccacagt gaaatctcga tggagtgggt cccatcagtt tgaacagttg tctggatcca   1920
ttttgtggat ggcaccagaa gtaatcagaa tgcaagataa aaacccatat agctttcagt   1980
cagatgtata tgcatttggg attgttctgt atgaattgat gaccggacag ttaccttatt   2040
caaatatcaa caacagggac cagataattt ttatggtggg acgaggatat ctgtctccag   2100
atctcagtaa ggtacggagt aactgtccaa aagccatgaa gagattaatg gcagagtgcc   2160
taaaaaagaa aagagatgaa agaccactct ttccccaagt aggaaagact ctcctaagca   2220
agagacaaaa ttcagaagtt atcagggaaa aagataagca gattctcgcc tctattgagc   2280
tgctggcccg ctcattgcca aaaattcacc gcagtgcatc agaaccctcc ttgaatcggg   2340
ctggcttcca aacagaggat tttagtctat atgcttgtgc ttctccaaaa acacccattc   2400
aggcaggggg atatgaagca gatttggctc ttacatcaaa taaaaataga gtagaagttg   2460
ggatttagag atttcctgac atgcaagaag gaataagcaa gaaaaaaagg tttgttttcc   2520
ccaaatcata tctattgtct tttacttcta tttttttctta aatttttttgt gatttcagag   2580
acatgtagag ttttattgat acctaaacta tgagttcttt tttttttttt tttttcatta   2640
ttttgatttt tttggccaag aggcatatgg gatcttagct tgagaaagca acaattttct   2700
tgatgtcatt ttgggtgagg gcacatattg ctgtgaacag tgtggtgata gccaccaggg   2760
accaaactca cacccgctgc attgaaaggt gaagtcttaa acactggacc agcagagaaa   2820
ttcctactct atgagttctt tttgtcatcc cctccccgca ccctccaccc ccaacctaaa   2880
gtctgatgat gaaatcaaca actattccat tagaagcagt agattctggt agcatgatct   2940
ttagtttgtt agtaagattt tgtgctttgt ggggttgtgt cgttttaagg ctaatattta   3000
agtttgtcaa atagaatgct gttcagattg taaaaatgag taataaacat ctgaagtttt   3060
ttttaagtta tttttaacat ggtatataca gttgagctta gagtttatca ttttctgata   3120
ttctcttact tagtagatga attctagcca tttttttataa agatttctgt taagcaaatc   3180
ctgttttcac atgggcttcc tttaagggat tttagattct gctggatatg gtgactgctc   3240
ataagactgt tgaaaattac ttttaagatg tattagaata cttctgaaaa aaaatagcaa   3300
ccttaaaacc ataagcaaaa gtagtaaggg tgtttataca tttctagagt ccctgtttag   3360
gtaatagcct cctatgattg tactttaaat gttttgctct ccaaggtttt agtaacttgg   3420
cttttttttct aatcagtgcc aaactccccc agttttttta actttaaata tgaggtaata   3480
aatcttttac ccttccttga tcttttgact tataatacct tggtcagttg tttcttaaaa   3540
ggaatcctta aatggaaaga gacaatatca ctgtctgcag ttctgattag tagttttatt   3600
cagaatggaa aaacagatta ttcatttttg aaaattgttc aggggtatgt tcattgttag   3660
gaccttggac tttggagtca gtgcctagct atgcattcca ggtctgccat tttctggctg   3720
tgaaattttg gacaagttac ttaaccactt taaaccccag ctttaagaag taaattaacc   3780
```

```
ccagtaaatt aagaagtaat agcagccact tcgtagagtt gttatgaggc tcagatgcag   3840

tgcaaatgtg tataaagtat tcagggagtc acctggtata ctataataga cactagaata   3900

gttgccaata ttatcagcat acaatctgag gattctgtca gccaatcatt agcaatctgt   3960

tgtttgttgg gacatgccag tgttctccag ttgaaatcag tagcaatcta aaaatggata   4020

gattattcct catttaaata gtgtgttcat ataagtgatt gcttggatcc ttatcagaag   4080

ttgctgttac tgaaaaatga taaggctgac taaattgtga tagttgtcag ttactaacca   4140

actcccagaa atgaataaga ggaacctatc tctagttcct agtagaaggt atggacaaaa   4200

tagtaggtga aaaataatgt cttgaacccc caaattaagt aagctttaaa gagtacaata   4260

cctcaaaggg tctttgcggt ttaaaatttg tatgctgaga atgatgttca ttgacatgtg   4320

cctatatgta attttttgat agtttaaaag gtgaaatgaa ctacagatgg gagaggtctg   4380

aattttcttg ccttcagtca aatgtgtaat gtggacatat tatttgacct gtgaatttta   4440

tcttttaaaa aagattaatt cctgcttctt ccttcctaat agttgcatta taataatgaa   4500

aatgagttga taatttgggg ggaaagtatt ctacaaatca accttattat tttaccattg   4560

gtttctgaga aattttgttc atttgaaccg tttatagctt gattagaatc atagcatgta   4620

aaacccaact gagggattat ctgcagactt aatgtagtat tatgtaagtt gtcttctttc   4680

atttcgacct tttttgcttt tgttgttgct agatctgtag tatgtagcta gtcacctttc   4740

agcgaggttt cagcgaggct tttctgtgtc tctaggttat ttgagataac ttttttaaaa   4800

ttagctcttg tcctcc                                                   4816
```

```
<210> SEQ ID NO 28
<211> LENGTH: 757
<212> TYPE: PRT
<213> ORGANISM: Bos taurus

<400> SEQUENCE: 28

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
```

```
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Glu Pro Pro
        275                 280                 285

Ile Leu Thr Ser Pro Ser Pro Ser Lys Ser Ile Pro Ile Pro Gln Pro
    290                 295                 300

Phe Arg Pro Ala Asp Glu Asp His Arg Asn Gln Phe Gly Gln Arg Asp
305                 310                 315                 320

Arg Ser Ser Ser Ala Pro Asn Val His Ile Asn Thr Ile Glu Pro Val
                325                 330                 335

Asn Ile Asp Asp Leu Ile Arg Asp Gln Gly Phe Arg Ser Asp Gly Gly
            340                 345                 350

Ser Thr Thr Gly Leu Ser Ala Thr Pro Pro Ala Ser Leu Pro Gly Ser
        355                 360                 365

Leu Ser Asn Val Lys Ala Leu Gln Lys Ser Pro Gly Pro Gln Arg Glu
    370                 375                 380

Arg Lys Ser Ser Ser Ser Ser Glu Asp Arg Asn Arg Met Lys Thr Leu
385                 390                 395                 400

Gly Arg Arg Asp Ser Ser Asp Asp Trp Glu Ile Pro Asp Gly Gln Ile
                405                 410                 415

Thr Val Gly Gln Arg Ile Gly Ser Gly Ser Phe Gly Thr Val Tyr Lys
            420                 425                 430

Gly Lys Trp His Gly Asp Val Ala Val Lys Met Leu Asn Val Thr Ala
        435                 440                 445

Pro Thr Pro Gln Gln Leu Gln Ala Phe Lys Asn Glu Val Gly Val Leu
    450                 455                 460

Arg Lys Thr Arg His Val Asn Ile Leu Leu Phe Met Gly Tyr Ser Thr
465                 470                 475                 480

Lys Pro Gln Leu Ala Ile Val Thr Gln Trp Cys Glu Gly Ser Ser Leu
                485                 490                 495

Tyr His His Leu His Ile Ile Glu Thr Lys Phe Glu Met Ile Lys Leu
            500                 505                 510

Ile Asp Ile Ala Arg Gln Thr Ala Gln Gly Met Asp Tyr Leu His Ala
        515                 520                 525

Lys Ser Ile Ile His Arg Asp Leu Lys Ser Asn Asn Ile Phe Leu His
    530                 535                 540

Glu Asp Leu Thr Val Lys Ile Gly Asp Phe Gly Leu Ala Thr Val Lys
545                 550                 555                 560

Ser Arg Trp Ser Gly Ser His Gln Phe Glu Gln Leu Ser Gly Ser Ile
                565                 570                 575

Leu Trp Met Ala Pro Glu Val Ile Arg Met Gln Asp Lys Asn Pro Tyr
            580                 585                 590

Ser Phe Gln Ser Asp Val Tyr Ala Phe Gly Ile Val Leu Tyr Glu Leu
        595                 600                 605
```

-continued

```
Met Thr Gly Gln Leu Pro Tyr Ser Asn Ile Asn Asn Arg Asp Gln Ile
    610                 615                 620

Ile Phe Met Val Gly Arg Gly Tyr Leu Ser Pro Asp Leu Ser Lys Val
625                 630                 635                 640

Arg Ser Asn Cys Pro Lys Ala Met Lys Arg Leu Met Ala Glu Cys Leu
                645                 650                 655

Lys Lys Lys Arg Asp Glu Arg Pro Leu Phe Pro Gln Val Gly Lys Thr
            660                 665                 670

Leu Leu Ser Lys Arg Gln Asn Ser Glu Val Ile Arg Glu Lys Asp Lys
        675                 680                 685

Gln Ile Leu Ala Ser Ile Glu Leu Leu Ala Arg Ser Leu Pro Lys Ile
    690                 695                 700

His Arg Ser Ala Ser Glu Pro Ser Leu Asn Arg Ala Gly Phe Gln Thr
705                 710                 715                 720

Glu Asp Phe Ser Leu Tyr Ala Cys Ala Ser Pro Lys Thr Pro Ile Gln
                725                 730                 735

Ala Gly Gly Tyr Glu Ala Asp Leu Ala Leu Thr Ser Asn Lys Asn Arg
            740                 745                 750

Val Glu Val Gly Ile
        755
```

<210> SEQ ID NO 29
<211> LENGTH: 2499
<212> TYPE: DNA
<213> ORGANISM: Bos taurus

<400> SEQUENCE: 29

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg gggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780

tttacagaat tcaggatggg gagaagaaac caattggctg ggacactgat atttcctggc     840

ttactggaga ggagttgcat gtagaagtgt tggagaatgt tccacttaca acacacaact     900

ttgtacggaa aactttttc accttagcat tttgtgactt ctgtagaaag ctgcttttcc      960

agggattccg ctgtcaaaca tgtggttata aatttcacca gcgttgtagt acagaggttc    1020

cactgatgtg tgttaattat gaccaactag atttgctgtt tgtctccaag ttctttgaac    1080

accacccaat accacaggag gaggcctcct tagcagagac taccottcca tgtggctcat    1140

ccccttctgc accccctcc gattctattg ggcccccaat tctcaccagt ccatctcctt     1200
```

```
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccct gcctcattac ctggctcact ctctaatgtg aaagcattgc   1440
agaaatctcc aggacctcag cgagaaagaa agtcctcttc atcctcagaa gacaggaatc   1500
gaatgaaaac gcttggtaga cggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact tacacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaaagaa aagagatgaa agaccactct ttccccaagt aggaaagact ctcctaagca   2340
agagacaaaa ttcagaagtt atcagggaaa aagataagca ggaaaagtat gtttctttag   2400
tacattccag gcatttggga ttacagtaaa aacaatattc tcgcctctat tgagctgctg   2460
gcccgctcat tgccaaaaat tcaccgcagt gcatcagaa                          2499
```

```
<210> SEQ ID NO 30
<211> LENGTH: 744
<212> TYPE: PRT
<213> ORGANISM: Bos taurus

<400> SEQUENCE: 30

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140
```

-continued

```
Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
```

-continued

```
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Glu Lys Tyr Val Ser Leu Val
                725                 730                 735

His Ser Arg His Leu Gly Leu Gln
            740
```

<210> SEQ ID NO 31
<211> LENGTH: 2404
<212> TYPE: DNA
<213> ORGANISM: Bos taurus

<400> SEQUENCE: 31

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttcccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg ggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780

tttacagaat tcaggatggg gagaagaaac caattggctg ggacactgat atttcctggc     840

ttactggaga ggagttgcat gtagaagtgt tggagaatgt tccacttaca acacacaact     900

ttgtacggaa aactttttttc accttagcat tttgtgactt ctgtagaaag ctgcttttcc     960

agggattccg ctgtcaaaca tgtggttata aatttcacca gcgttgtagt acagaggttc    1020

cactgatgtg tgttaattat gaccaactag atttgctgtt tgtctccaag ttctttgaac    1080
```

accacccaat accacaggag gaggcctcct tagcagagac taccettcca tgtggctcat 1140 ccccttctgc accccccctcc gattctattg ggcccccaat tctcaccagt ccatctcctt 1200
caaaatccat tccaattcca cagcctttcc gaccagcaga tgaagatcat cgaaatcagt 1260
ttggacaacg agaccggtcc tcatcagctc caaatgtgca tataaacaca atagaacccg 1320
tcaatattga tgacttgatt agagaccaag ggtttcgtag tgatggagga tcaaccacag 1380
gtttatccgc cacaccccct gcctcattac ctggctcact ctctaatgtg aaagcattgc 1440
agaaatctcc aggacctcag cgagaaagaa agtcctcttc atcctcagaa gacaggaatc 1500
gaatgaaaac gcttggtaga cgggattcaa gtgacgattg ggagattcct gatggacaga 1560
tcacagtggg acaaagaatt ggatcagggt catttgggac agtctacaag ggaaagtggc 1620
atggtgatgt ggcagtgaaa atgttgaatg tgacagcacc cacacctcag cagttacagg 1680
ccttcaaaaa tgaagtagga gtactcagga aaacgcgaca tgtgaatatc ctcctcttca 1740
tgggttattc aacaaagcca caactggcta ttgttaccca gtggtgtgag ggctccagtt 1800
tatatcatca tctccacatc attgagacca aattcgagat gatcaaactt atagatattg 1860
cacggcagac tgcacagggc atggattact tacacgccaa gtcaatcatc cacagagacc 1920
tcaagagtaa taatattttt cttcatgaag acctcacagt aaaaataggt gattttggtc 1980
tagccacagt gaaatctcga tggagtgggt cccatcagtt tgaacagttg tctggatcca 2040
ttttgtggat ggcaccagaa gtaatcagaa tgcaagataa aaacccatat agctttcagt 2100
cagatgtata tgcatttggg attgttctgt atgaattgat gaccggacag ttaccttatt 2160
caaatatcaa caacagggac cagataattt ttatggtggg acgaggatat ctgtctccag 2220
atctcagtaa ggtacggagt aactgtccaa aagccatgaa gagattaatg gcagagtgcc 2280
taaaaaagaa aagagatgaa agaccactct ttccccaaga tctctcttcc caccatagac 2340
acaaaaattt cagatggcta caggtttaca tgtaaaaaac agaattataa caaatgattt 2400
ttat 2404

<210> SEQ ID NO 32
<211> LENGTH: 726
<212> TYPE: PRT
<213> ORGANISM: Bos taurus

<400> SEQUENCE: 32

Met Ala Ala Leu Ser Gly Gly Gly Gly Gly Gly Gly Gly Ala Glu
1 5 10 15

Gln Gly Gln Ala Leu Phe Asn Gly Asp Met Glu Pro Glu Ala Gly Ala
20 25 30

Ala Ala Ser Ser Ala Ala Asp Pro Ala Ile Pro Glu Glu Val Trp Asn
35 40 45

Ile Lys Gln Met Ile Lys Leu Thr Gln Glu His Ile Glu Ala Leu Leu
50 55 60

Asp Lys Phe Gly Gly Glu His Asn Pro Pro Ser Ile Tyr Leu Glu Ala
65 70 75 80

Tyr Glu Glu Tyr Thr Ser Lys Leu Asp Ala Leu Gln Gln Arg Glu Gln
85 90 95

Gln Leu Leu Glu Ser Leu Gly Asn Gly Thr Asp Phe Ser Val Ser Ser
100 105 110

Ser Ala Ser Thr Asp Thr Val Thr Ser Ser Ser Ser Ser Ser Leu Ser
115 120 125

Val Leu Pro Ser Ser Leu Ser Val Phe Gln Asn Pro Thr Asp Val Ser

```
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560
```

```
Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
    690                 695                 700

Leu Phe Pro Gln Asp Leu Ser Ser His His Arg His Lys Asn Phe Arg
705                 710                 715                 720

Trp Leu Gln Val Tyr Met
                725
```

<210> SEQ ID NO 33
<211> LENGTH: 2331
<212> TYPE: DNA
<213> ORGANISM: Bos taurus

<400> SEQUENCE: 33

```
ctcagctgcg ccgggtctca caagacggtt cccgaggtgg cccaggcgcc gtcccaccgc      60

cgacgccgcc cgggccgccc gggccgtccc tccccgctgc cccccgtcct ccgcctccgc     120

ctccccccgc cctcagcctc ccttccccct ccccgcccag cagcggtcgc tcgggcccgg     180

ctctcggtta taagatggcg gcgctgagtg gcggcggcgg cggcggcggc ggtggcgcgg     240

agcagggcca ggctctgttc aacggggaca tggagcccga ggccggcgcc gcggcctctt     300

cggctgcgga ccccgccatt cccgaggagg tgtggaatat caaacaaatg attaagttga     360

cacaggagca tatagaggcc ctattggaca aatttggtgg ggagcataat ccaccatcaa     420

tatatctgga ggcctatgaa gaatacacca gcaagctaga tgccctccaa caaagagaac     480

aacagttatt ggaatccctg gggaatggaa ctgatttttc tgtttctagc tctgcatcaa     540

cggacaccgt tacatcttct tcctcttcta gcctttcagt gctgccttca tctctttcag     600

tttttcaaaa tcccacagat gtgtcacgga gcaaccccaa gtcaccacaa aaacctatcg     660

ttagagtctt cctgcccaat aaacagagga cagtggtacc tgcacggtgt ggagtcacag     720

tccgggacag cctgaagaag gcactgatga tgagaggtct aatcccagag tgctgtgctg     780

tttacagaat tcaggatggg gagaagaaac caattggctg ggacactgat atttcctggc     840

ttactggaga ggagttgcat gtagaagtgt tggagaatgt tccacttaca acacacaact     900

ttgtacggaa aactttttc accttagcat tttgtgactt ctgtagaaag ctgcttttcc     960

agggattccg ctgtcaaaca tgtggttata aatttcacca gcgttgtagt acagaggttc    1020

cactgatgtg tgttaattat gaccaactag atttgctgtt tgtctccaag ttctttgaac    1080

accacccaat accacaggag gaggcctcct tagcagagac taccottcca tgtggctcat    1140
```

-continued

```
ccccttctgc accccccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacacccccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560

tcacagtggg acaaagaatt ggatcagggt catttgggac agtctacaag ggaaagtggc   1620

atggtgatgt ggcagtgaaa atgttgaatg tgacagcacc cacacctcag cagttacagg   1680

ccttcaaaaa tgaagtagga gtactcagga aaacgcgaca tgtgaatatc ctcctcttca   1740

tgggttattc aacaaagcca caactggcta ttgttaccca gtggtgtgag ggctccagtt   1800

tatatcatca tctccacatc attgagacca aattcgagat gatcaaactt atagatattg   1860

cacggcagac tgcacagggc atggattact tacacgccaa gtcaatcatc cacagagacc   1920

tcaagagtaa taatattttt cttcatgaag acctcacagt aaaaataggt gattttggtc   1980

tagccacagt gaaatctcga tggagtgggt cccatcagtt tgaacagttg tctggatcca   2040

ttttgtggat ggcaccagaa gtaatcagaa tgcaagataa aaacccatat agctttcagt   2100

cagatgtata tgcatttggg attgttctgt atgaattgat gaccggacag ttaccttatt   2160

caaatatcaa caacagggac caggtgcttt gtcctccatg ggagtgtaat aaatgctgtg   2220

caagggctta cttcccatga gagaagtgag tgaccaacag aaggataatt tttatggtgg   2280

gacgaggata tctgtctcca gatctcagta aggtacggag taactgtcca a            2331
```

<210> SEQ ID NO 34
<211> LENGTH: 681
<212> TYPE: PRT
<213> ORGANISM: Bos taurus

<400> SEQUENCE: 34

```
Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160
```

-continued

```
Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
```

-continued

```
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680


<210> SEQ ID NO 35
<211> LENGTH: 2319
<212> TYPE: DNA
<213> ORGANISM: Bos taurus

<400> SEQUENCE: 35

ctcagctgcg ccgggtctca caagacggtt cccgaggtgg cccaggcgcc gtcccaccgc     60

cgacgccgcc cgggccgccc gggccgtccc tccccgctgc cccccgtcct ccgcctccgc    120

ctcccccgc cctcagcctc ccttccccct ccccgcccag cagcggtcgc tcgggcccgg    180

ctctcggtta taagatggcg gcgctgagtg gcggcggcgg cggcggcggc ggtggcgcgg    240

agcagggcca ggctctgttc aacggggaca tggagcccga ggccggcgcc gcggcctctt    300

cggctgcgga ccccgccatt cccgaggagg tgtggaatat caaacaaatg attaagttga    360

cacaggagca tatagaggcc ctattggaca aatttggtgg ggagcataat ccaccatcaa    420

tatatctgga ggcctatgaa gaatacacca gcaagctaga tgccctccaa caaagagaac    480

aacagttatt ggaatccctg gggaatggaa ctgatttttc tgtttctagc tctgcatcaa    540

cggacaccgt tacatcttct tcctcttcta gcctttcagt gctgccttca tctctttcag    600

tttttcaaaa tcccacagat gtgtcacgga gcaaccccaa gtcaccacaa aaacctatcg    660

ttagagtctt cctgcccaat aaacagagga cagtggtacc tgcacggtgt ggagtcacag    720

tccgggacag cctgaagaag gcactgatga tgagaggtct aatcccagag tgctgtgctg    780

tttacagaat tcaggatggg gagaagaaac caattggctg ggacactgat atttcctggc    840

ttactggaga ggagttgcat gtagaagtgt tggagaatgt tccacttaca acacacaact    900

ttgtacggaa aactttttc accttagcat tttgtgactt ctgtagaaag ctgcttttcc    960

agggattccg ctgtcaaaca tgtggttata aatttcacca gcgttgtagt acagaggttc   1020

cactgatgtg tgttaattat gaccaactag atttgctgtt tgtctccaag ttctttgaac   1080

accacccaat accacaggag gaggcctcct tagcagagac taccettcca tgtggctcat   1140

ccccttctgc accccctcc gattctattg ggcccccaat tctcaccagt ccatctcctt   1200

caaaatccat tccaattcca cagcctttcc gaccagcaga tgaagatcat cgaaatcagt   1260

ttggacaacg agaccggtcc tcatcagctc caaatgtgca tataaacaca atagaacccg   1320

tcaatattga tgacttgatt agagaccaag ggtttcgtag tgatggagga tcaaccacag   1380

gtttatccgc cacacccct gcctcattac ctggctcact ctctaatgtg aaagcattgc   1440

agaaatctcc aggacctcag cgagaaagaa agtcctcttc atcctcagaa gacaggaatc   1500

gaatgaaaac gcttggtaga cgggattcaa gtgacgattg ggagattcct gatggacaga   1560
```

```
tcacagtggg acaaagaatt ggatcagggt catttgggac agtctacaag ggaaagtggc   1620

atggtgatgt ggcagtgaaa atgttgaatg tgacagcacc cacacctcag cagttacagg   1680

ccttcaaaaa tgaagtagga gtactcagga aaacgcgaca tgtgaatatc ctcctcttca   1740

tgggttattc aacaaagcca caactggcta ttgttaccca gtggtgtgag ggctccagtt   1800

tatatcatca tctccacatc attgagacca aattcgagat gatcaaactt atagatattg   1860

cacggcagac tgcacagggc atggattact tacacgccaa gtcaatcatc cacagagacc   1920

tcaagagtaa taatattttt cttcatgaag acctcacagt aaaaataggt gattttggtc   1980

tagccacagt gaaatctcga tggagtgggt cccatcagtt tgaacagttg tctggatcca   2040

ttttgtggat ggcaccagaa gtaatcagaa tgcaagataa aaacccatat agctttcagt   2100

cagatgtata tgcatttggg attgttctgt atgaattgat gaccggacag ttaccttatt   2160

caaatatcaa caacagggac caggtgcttt gtcctccatg ggagtgtaat aaatgctgtg   2220

caagggctta cttcccatga gagaagtgag tgaccaacag aaggtctgtg caaggaaaag   2280

agacaaagcc acggatcaga agcacatggc cataactga                          2319
```

```
<210> SEQ ID NO 36
<211> LENGTH: 681
<212> TYPE: PRT
<213> ORGANISM: Bos taurus

<400> SEQUENCE: 36

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240
```

-continued

```
Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655
```

-continued

```
Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680


<210> SEQ ID NO 37
<211> LENGTH: 2661
<212> TYPE: DNA
<213> ORGANISM: Bos taurus

<400> SEQUENCE: 37

tcagctgcgc cgggtctcac aagacggttc ccgaggtggc ccaggcgccg tcccaccgcc     60

gacgccgccc gggccgcccg ggccgtccct ccccgctgcc ccccgtcctc cgcctccgcc    120

tccccccgcc ctcagcctcc cttccccctc cccgcccagc agcggtcgct cgggcccggc    180

tctcggttat aagatggcgg cgctgagtgg cggcggcggc ggcggcggcg gtggcgcgga    240

gcagggccag gctctgttca acggggacat ggagcccgag gccggcgccg cggcctcttc    300

ggctgcggac cccgccattc ccgaggaggt gtggaatatc aaacaaatga ttaagttgac    360

acaggagcat atagaggccc tattggacaa atttggtggg gagcataatc caccatcaat    420

atatctggag gcctatgaag aatacaccag caagctagat gccctccaac aaagagaaca    480

acagttattg gaatccctgg ggaatggaac tgatttttct gtttctagct ctgcatcaac    540

ggacaccgtt acatcttctt cctcttctag cctttcagtg ctgccttcat ctctttcagt    600

ttttcaaaat cccacagatg tgtcacggag caaccccaag tcaccacaaa aacctatcgt    660

tagagtcttc ctgcccaata aacagaggac agtggtacct gcacggtgtg gagtcacagt    720

ccgggacagc ctgaagaagg cactgatgat gagaggtcta atcccagagt gctgtgctgt    780

ttacagaatt caggatgggg agaagaaacc aattggctgg gacactgata tttcctggct    840

tactggagag gagttgcatg tagaagtgtt ggagaatgtt ccacttacaa cacacaactt    900

tgtacggaaa actttttttca ccttagcatt ttgtgacttc tgtagaaagc tgcttttcca    960

gggattccgc tgtcaaacat gtggttataa atttcaccag cgttgtagta cagaggttcc   1020

actgatgtgt gttaattatg accaactaga tttgctgttt gtctccaagt tctttgaaca   1080

ccacccaata ccacaggagg aggcctcctt agcagagact acccttccat gtggctcatc   1140

cccttctgca cccccctccg attctattgg gcccccaatt ctcaccagtc catctccttc   1200

aaaatccatt ccaattccac agcctttccg accagcagat gaagatcatc gaaatcagtt   1260

tggacaacga gaccggtcct catcagctcc aaatgtgcat ataaacacaa tagaacccgt   1320

caatattgat gacttgatta gagaccaagg gtttcgtagt gatggaggat caaccacagg   1380

tttatccgcc acaccccctg cctcattacc tggctcactc tctaatgtga aagcattgca   1440

gaaatctcca ggacctcagc gagaaagaaa gtcctcttca tcctcagaag acaggaatcg   1500

aatgaaaacg cttggtagac gggattcaag tgacgattgg gagattcctg atggacagat   1560

cacagtggga caaagaattg gatcagggtc atttgggaca gtctacaagg gaaagtggca   1620

tggtgatgtg gcagtgaaaa tgttgaatgt gacagcaccc acacctcagc agttacaggc   1680

cttcaaaaat gaagtaggag tactcaggaa aacgcgacat gtgaatatcc tcctcttcat   1740

gggttattca acaaagccac aactggctat tgttacccag tggtgtgagg gctccagttt   1800

atatcatcat ctccacatca ttgagaccaa attcgagatg atcaaactta tagatattgc   1860

acggcagact gcacagggca tggattactt acacgccaag tcaatcatcc acagagacct   1920

caagagtaat aatatttttc ttcatgaaga cctcacagta aaaataggtg attttggtct   1980
```

-continued

```
agccacagtg aaatctcgat ggagtgggtc ccatcagttt gaacagttgt ctggatccat   2040

tttgtggatg gcaccagaag taatcagaat gcaagataaa aacccatata gctttcagtc   2100

agatgtatat gcatttggga ttgttctgta tgaattgatg accggacagt taccttattc   2160

aaatatcaac aacagggacc agtctgtgca aggaaaagag acaaagccac ggatcagaag   2220

cacatggcca taactgaaga ttttgtgaac tctcacaagg aaaaaatttg ctctttgaac   2280

aataagaagg aactcactaa aatgtaactg agaactgttc aacaggttga aagctgaaag   2340

atgccattgg aactgacaaa atgtttctta aacataaatg atgaaacagt gaaactacat   2400

aatatctcct ctggctgaaa cattcaagaa gtttaaaatg cttaagttaa aaataaaatc   2460

ctagtaaaca atggacttac tgtgcaacat agagaatatc ttacgataac ctgtaatgga   2520

aaagaatctg aaaaagaatg tatataactg aatcactttg ctgtaaacta gaatctgaca   2580

caacactgta aatcactaca cttttctgtt gcatgccaaa gattatttaa taacgtcatt   2640

aaaaaattat tttaataatt a                                              2661
```

<210> SEQ ID NO 38
<211> LENGTH: 679
<212> TYPE: PRT
<213> ORGANISM: Bos taurus

<400> SEQUENCE: 38

```
Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
```

-continued

```
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ser Val Gln Gly Lys Glu Thr Lys Pro
            660                 665                 670
```

```
Arg Ile Arg Ser Thr Trp Pro
        675


<210> SEQ ID NO 39
<211> LENGTH: 7434
<212> TYPE: DNA
<213> ORGANISM: Bos taurus

<400> SEQUENCE: 39

acaccgttac atcttcttcc tcttctagcc tttcagtgct gccttcatct ctttcagttt      60

ttcaaaatcc cacagatgtg tcacggagca accccaagtc accacaaaaa cctatcgtta     120

gagtcttcct gcccaataaa cagaggacag tggtacctgc acggtgtgga gtcacagtcc     180

gggacagcct gaagaaggca ctgatgatga gaggtctaat cccagagtgc tgtgctgttt     240

acagaattca ggatggggag aagaaaccaa ttggctggga cactgatatt tcctggctta     300

ctggagagga gttgcatgta gaagtgttgg agaatgttcc acttacaaca cacaactttg     360

tacggaaaac ttttttcacc ttagcatttt gtgacttctg tagaaagctg cttttccagg     420

gattccgctg tcaaacatgt ggttataaat ttcaccagcg ttgtagtaca gaggttccac     480

tgatgtgtgt taattatgac caactagatt tgctgtttgt ctccaagttc tttgaacacc     540

acccaatacc acaggaggag gcctccttag cagagactac ccttccatgt ggctcatccc     600

cttctgcacc cccctccgat tctattgggc cccaattcct caccagtcca tctccttcaa     660

aatccattcc aattccacag cctttccgac cagcagatga agatcatcga aatcagtttg     720

gacaacgaga ccggtcctca tcagctccaa atgtgcatat aaacacaata gaacccgtca     780

atattgatga cttgattaga gaccaagggt ttcgtagtga tggaggatca accacaggtt     840

tatccgccac accccctgcc tcattacctg gctcactctc taatgtgaaa gcattgcaga     900

aatctccagg acctcagcga gaaagaaagt cctcttcatc ctcagaagac aggaatcgaa     960

tgaaaacgct tggtagacgg gattcaagtg acgattggga gattcctgat ggacagatca    1020

cagtgggaca aagaattgga tcagggtcat ttgggacagt ctacaaggga aagtggcatg    1080

gtgatgtggc agtgaaaatg ttgaatgtga cagcacccac acctcagcag ttacaggcct    1140

tcaaaaatga agtaggagta ctcaggaaaa cgcgacatgt gaatatcctc ctcttcatgg    1200

gttattcaac aaagccacaa ctggctattg ttacccagtg gtgtgagggc tccagtttat    1260

atcatcatct ccacatcatt gagaccaaat tcgagatgat caaacttata gatattgcac    1320

ggcagactgc acagggcatg gattacttac acgccaagtc aatcatccac agagacctca    1380

agagtaataa tatttttctt catgaagacc tcacagtaaa aataggtgat tttggtctag    1440

ccacagtgaa atctcgatgg agtgggtccc atcagtttga acagttgtct ggatccattt    1500

tgtggatggc accagaagta atcagaatgc aagataaaaa cccatatagc tttcagtcag    1560

atgtatatgc atttgggatt gttctgtatg aattgatgac cggacagtta ccttattcaa    1620

atatcaacaa cagggaccag ataattttta tggtgggacg aggatatctg tctccagatc    1680

tcagtaaggt acggagtaac tgtccaaaag ccatgaagag attaatggca gagtgcctaa    1740

aaaagaaaag agatgaaaga ccactctttc cccaagtagg aaagactctc ctaagcaaga    1800

gacaaaattc agaagttatc agggaaaaag ataagcagat tctcgcctct attgagctgc    1860

tggcccgctc attgccaaaa attcaccgca gtgcatcaga accctccttg aatcgggctg    1920

gcttccaaac agaggatttt agtctatatg cttgtgcttc tccaaaaaca cccattcagg    1980

cagggggata tggagaattt gcagccttca agtagccaca ccatcatgac agcatctact    2040
```

-continued

```
cttatttctt aagtcttgtg ttcgtacaat ttgttaacat caaaacacag ttctgttcct   2100
caactctttt taaagttaaa atttttcagt gcataagctg gtgtggaaca gaaggaaatt   2160
tcccatccaa caaaagaggg aagaatgttt taggaaccag aattctctgc tgccagtgtt   2220
tcttcttcaa cacaaatatc acaagtctgc ccactcccag gaagaaagag gagagaccct   2280
gagttctgac cttttgatgg tcaggcatga tggaaagaaa ctgctgctac agcttgggag   2340
atttgctctg ggaagtctgc cagtcaactt tgcccttcta accaccagat caatatgtgg   2400
ctgatcatct gatggggcag ttgcaatcac caagccttgt tctctttcct gttctgggat   2460
tgtgttgtgg aacccttttc cctagccacc accagttcat ttctgaggga tggaacaaaa   2520
atgcagcatg cccttcctgt gtggtgcatg ttcagtcctt gacaaatttt taccaaaatg   2580
aagctacttt atttaaaagg agggtgagag gtgaggaggt cactttgggt gtggcggaaa   2640
gggaatgctg catctttttc ctgggctgct ggggctctgg ccttggcttg ccagccggaa   2700
gcgctggcac gcatcgcctt cttttcccat tgggtccagc aatgaagacg agtgtttggg   2760
gttttttttt tctccaccat gtagcaagtt ctcaggaaaa tacaattgat atcttcctcc   2820
taagctcttc caatcagtca ccaagtactt atgtggttac tttgtccagg gcacaaaatg   2880
cctgtatcta attaaaagcc tacaaaactg cttgataaca gttttgaatg tgagacattt   2940
atgtaattta aatgtaaggt acaagtttta atttctgagt ttcttctatt atatttttat   3000
taaaaaaaga aaataatttt cagattgaat tggagtaaaa taatattact tcccactaga   3060
attatatatc ctggaaaatt gtatttttgt tacataagca gcttttaaag aaagatcatt   3120
acccttttct ctacataaat atatggggag tcttagccta atgacaaata tttataattt   3180
ttaaattaat ggtacttgct ggatccatac taacatcttt actaatacct cattgtttct   3240
tccaacttac tcctacacta catcctacat cttcttccta gtcttttatc tagaatatgc   3300
aacctcaaat aaaaatggtg gtgtcctcat tcattctcct ccttcctttt ttcccaagcc   3360
tgatcttcaa aaggttggtt aatttggcag ctgagttcct ccccaggcag agaatagacc   3420
aattttaggt gtattgggac tgagggagga tgtgtaaaga ttaacatcag taaagaaccg   3480
ctgtggagta attaagaact ttgttcttta taactggaga atataaccta accctaacat   3540
ccctcagcct ttactaaagt gtggcgtaaa tcacagtagt agcaaagaaa gtgactctgg   3600
atgtgttcct ggccagtacc tcccttatca tgaatgtaga ctctctcatc aagatttagg   3660
aatataaatc aaatcaaatg tgcccagcca agctatgtag taagggactt gaacaatatt   3720
aggcagaacc tataaaataa atcagggaat tagaaattat ttaaagtttt caaattgtaa   3780
attgccccgg tgtctttcag cctactgcca ttatttttgc tacaatacct acatttcaga   3840
ggagggccta ctgaaaattc catgcaagtg gaaaataatc ctcaagttat taatgagttt   3900
gaaaagcaat gagttcttaa gtctttgtga gtagagcaag atcctacaaa attcagaaat   3960
agtaaaaatg gattcatgct gatttgaaga gcatctgtgt gcataatata atgctgcatc   4020
tcttttaaaa gcagtctatt tttcttttta aatttgtccc catagatgct tttgaacatg   4080
aacatgctta tgttaccttt tccgaggttg ggaagagcca ggagctctca ggcagggccc   4140
cctccctcag ctgggcagga gctgctcagg aggagctagt tatagaggaa gcttagcgtt   4200
ggcattttca aaattcaagg tgataacgct ttcttcttcc tttctgtttt agaatagatt   4260
gctgtctgat ttgaaaaagg gaaatagatt tgatctcaaa tgaatctgtg cccagaagcc   4320
aggctcaggg tattcagaga tttgtatagt gccctcaaaa aataacaaaa ttttagcttt   4380
```

-continued

```
cctttttct tcttttctcc atcaaattct tttttctcta gtttacaaat gacatggaaa   4440
aggaatttcc cctgagtttt gtatgccttt tttttttgg cttagactat agataggcgt   4500
gttgagctcc taagaaaata caaggaggaa ctctttgttg tgcagagcac tttatgagta   4560
gtttgtgtgg ataatatgtg actgcttccc tgacgagctt gtgaggctgt acttatgtct   4620
ttcctgtaag gcagcttcag tgccttctgt agtgtatata aggaaagatt acgccttctg   4680
aaaaatctca gagcaaccat aagattattt taaaatatgt agtatgactg atggactttt   4740
tcatcattaa attagtctag catctaaact tttaccactg aaataatatt gaccaaaaag   4800
caatttataa aaggtatttg tgaatagaaa atacaatgtg atcatttgta cttatgtgca   4860
ccttaaaaga ggaattctgt ctagctgtca aattctggtt ccttaacatc cagtccttga   4920
ttgtgattga gatctggtag gacgtgctgg ggcacgctag cagataaaat cccgtatact   4980
ttaggataga tgttacattt atgtcagtgt tggcaaagag cattgtgtag taataaagaa   5040
ttcaagactt cagcaatgtc aacctgaaac tttgtaaata tttcctagat tgttatttga   5100
tgcagtcaca gctctttatc acacaatgtt gtctttccct catcaggcaa ttttagaact   5160
gctgcacacc cctcctcaga tctcacctgc ccctcctgta cattcacctc tccagccttg   5220
tgcacacctc atttagcttt agtttgaaac acattgcagg gttcaggtga cctcttcaaa   5280
aactacctcc tcagaatgag gtaatgaata gttatttatt ttaaaatatg aaaagtcagg   5340
agctctagaa tatgaagatg atctaagatt ttaactttta tgtatacttg ttgagcactc   5400
tcctttgtc ctaaagggca ttatacattt aagcagtaat actgaaaaat gtagctcaga   5460
gtaactgaat gttgttgaaa gtggtgccag aatctgtttt aggggtacgt atcagaatct   5520
taatcttaaa tcggttacat gaaattaaat agttaatggt aacacttgac taacagatat   5580
aattttaatt ttcggtaggc ttttagcaag acagtaagta catcttcata atgagttagc   5640
cacagcttca tcacatgcac agattttcct gttgagagac tgcccagtta agagggtaga   5700
atgatgaacc atttttcagg attctcttct ttgtccaaac tggcattgtg agtgctagaa   5760
tatcagcact ttcaaactag tgattccaac tattaggcta ttaaaaagca aaacaaacca   5820
aacaaaccat agccagacat gggaagttta ctatgagtat aaacagcaaa tagcttacag   5880
gtcatacatt gaaatggtgt aggtaaggcg ttagaaaaat accttgacaa tttgccaaat   5940
gatcttactg tgccttcatg atgcaataaa aaaaaaaaaa atttagcata aatcagtgat   6000
ttgtgaagag agcagccacc ctggtctaac tcagctgtgt taatattttt tagcgtgcaa   6060
tttagactgc aaagataaat gcactaaaga gtttatagcc aaaatcacat ttaaaaaatg   6120
agagaaaaca caggtaaatt ttcagtgaac aaaattattt ttttaaagta cataatccct   6180
agtatagtca gatatattta tcacatagag caaataggtt gaaatcacaa ttcagtgaca   6240
tttctagaga aactttttct actcccatag gttcttcaaa gcatggaact tttatataac   6300
agaaatgtgt gacggtcatt ttaaattgct gtagtttggg gctgaagtac tgtgtgctgg   6360
gcagcaatca catgtattaa ctagtgagaa aggagaaatt aagatatagg acagaatttg   6420
attttcttgt tcccagatta ctgctgccaa cctagacact gagtttccag aggctgaaac   6480
gtaaacttgc agctcagcaa ctgttttgca aagttagtgg gactgtcctg cttatgctgt   6540
tcaaaaatgc tctgagggcc aggtggggcc tccaggggct cctctctgag gggacatcag   6600
actagctaac gacctggcgg gcggatgtga accggacaca ctccatggtg tgcttcttgt   6660
atcggtccct cgccaccctc aagaaaggct tcagcgggtt ctctagacgt ctccactaag   6720
gtgtgttact aacagccatg ggttgttgag cacccgagga gtgcaatagc atctctgcat   6780
```

```
gattgtatat tggcccgaag agaatgaagt ggccagtgta ctcatgttcc atgttgctag   6840

ctctggtaaa ctgaaaatac tggtaagatt tttgttttat cagtacacta gagagtaagc   6900

tttgttttgt tgtttttaga taatgttttc acttccattt ggaaagacat ttaaattgag   6960

tttcagtcct aaattttgcc agtcatggta attagcagtt tctatcaggt atttttaagg   7020

tagaagagga tagaaacata agttctaaaa gcttaaggta accgtggttt attttaaaat   7080

gtttaggggt ggttagtctc tacctcaaaa aaagtgagtg aatcttttat ttcagcattc   7140

acaagttcgg ctgttgtttt tgtaatacat ttttttttta accttttgac ccccctttac   7200

ctaagtgtca atgtagtttt attaattact aagtcagttt cattaaaatg tttatttagc   7260

agttttgact aattgcaatg attaatatag ccagttgtgc atgaggacac agccagtgag   7320

tatatctggg ttttttttgt gatgcttttt ttcttaagac ttctgtagat ttatgaagta   7380

ctcattgaaa acaactaaaa tacgtttatt cgtgttaata tggaaaaaaa aaaa         7434
```

<210> SEQ ID NO 40
<211> LENGTH: 603
<212> TYPE: PRT
<213> ORGANISM: Bos taurus

<400> SEQUENCE: 40

```
Met Met Arg Gly Leu Ile Pro Glu Cys Cys Ala Val Tyr Arg Ile Gln
1               5                   10                  15

Asp Gly Glu Lys Lys Pro Ile Gly Trp Asp Thr Asp Ile Ser Trp Leu
            20                  25                  30

Thr Gly Glu Glu Leu His Val Glu Val Leu Glu Asn Val Pro Leu Thr
        35                  40                  45

Thr His Asn Phe Val Arg Lys Thr Phe Phe Thr Leu Ala Phe Cys Asp
    50                  55                  60

Phe Cys Arg Lys Leu Leu Phe Gln Gly Phe Arg Cys Gln Thr Cys Gly
65                  70                  75                  80

Tyr Lys Phe His Gln Arg Cys Ser Thr Glu Val Pro Leu Met Cys Val
                85                  90                  95

Asn Tyr Asp Gln Leu Asp Leu Leu Phe Val Ser Lys Phe Phe Glu His
            100                 105                 110

His Pro Ile Pro Gln Glu Glu Ala Ser Leu Ala Glu Thr Thr Leu Pro
        115                 120                 125

Cys Gly Ser Ser Pro Ser Ala Pro Pro Ser Asp Ser Ile Gly Pro Pro
    130                 135                 140

Ile Leu Thr Ser Pro Ser Pro Ser Lys Ser Ile Pro Ile Pro Gln Pro
145                 150                 155                 160

Phe Arg Pro Ala Asp Glu Asp His Arg Asn Gln Phe Gly Gln Arg Asp
                165                 170                 175

Arg Ser Ser Ser Ala Pro Asn Val His Ile Asn Thr Ile Glu Pro Val
            180                 185                 190

Asn Ile Asp Asp Leu Ile Arg Asp Gln Gly Phe Arg Ser Asp Gly Gly
        195                 200                 205

Ser Thr Thr Gly Leu Ser Ala Thr Pro Pro Ala Ser Leu Pro Gly Ser
    210                 215                 220

Leu Ser Asn Val Lys Ala Leu Gln Lys Ser Pro Gly Pro Gln Arg Glu
225                 230                 235                 240

Arg Lys Ser Ser Ser Ser Ser Glu Asp Arg Asn Arg Met Lys Thr Leu
                245                 250                 255
```

```
Gly Arg Arg Asp Ser Ser Asp Asp Trp Glu Ile Pro Asp Gly Gln Ile
            260                 265                 270

Thr Val Gly Gln Arg Ile Gly Ser Gly Ser Phe Gly Thr Val Tyr Lys
        275                 280                 285

Gly Lys Trp His Gly Asp Val Ala Val Lys Met Leu Asn Val Thr Ala
    290                 295                 300

Pro Thr Pro Gln Gln Leu Gln Ala Phe Lys Asn Glu Val Gly Val Leu
305                 310                 315                 320

Arg Lys Thr Arg His Val Asn Ile Leu Leu Phe Met Gly Tyr Ser Thr
                325                 330                 335

Lys Pro Gln Leu Ala Ile Val Thr Gln Trp Cys Glu Gly Ser Ser Leu
            340                 345                 350

Tyr His His Leu His Ile Ile Glu Thr Lys Phe Glu Met Ile Lys Leu
        355                 360                 365

Ile Asp Ile Ala Arg Gln Thr Ala Gln Gly Met Asp Tyr Leu His Ala
    370                 375                 380

Lys Ser Ile Ile His Arg Asp Leu Lys Ser Asn Asn Ile Phe Leu His
385                 390                 395                 400

Glu Asp Leu Thr Val Lys Ile Gly Asp Phe Gly Leu Ala Thr Val Lys
                405                 410                 415

Ser Arg Trp Ser Gly Ser His Gln Phe Glu Gln Leu Ser Gly Ser Ile
            420                 425                 430

Leu Trp Met Ala Pro Glu Val Ile Arg Met Gln Asp Lys Asn Pro Tyr
        435                 440                 445

Ser Phe Gln Ser Asp Val Tyr Ala Phe Gly Ile Val Leu Tyr Glu Leu
    450                 455                 460

Met Thr Gly Gln Leu Pro Tyr Ser Asn Ile Asn Asn Arg Asp Gln Ile
465                 470                 475                 480

Ile Phe Met Val Gly Arg Gly Tyr Leu Ser Pro Asp Leu Ser Lys Val
                485                 490                 495

Arg Ser Asn Cys Pro Lys Ala Met Lys Arg Leu Met Ala Glu Cys Leu
            500                 505                 510

Lys Lys Lys Arg Asp Glu Arg Pro Leu Phe Pro Gln Val Gly Lys Thr
        515                 520                 525

Leu Leu Ser Lys Arg Gln Asn Ser Glu Val Ile Arg Glu Lys Asp Lys
    530                 535                 540

Gln Ile Leu Ala Ser Ile Glu Leu Leu Ala Arg Ser Leu Pro Lys Ile
545                 550                 555                 560

His Arg Ser Ala Ser Glu Pro Ser Leu Asn Arg Ala Gly Phe Gln Thr
                565                 570                 575

Glu Asp Phe Ser Leu Tyr Ala Cys Ala Ser Pro Lys Thr Pro Ile Gln
            580                 585                 590

Ala Gly Gly Tyr Gly Glu Phe Ala Ala Phe Lys
        595                 600


<210> SEQ ID NO 41
<211> LENGTH: 2295
<212> TYPE: DNA
<213> ORGANISM: Equus caballus
<220> FEATURE:
<221> NAME/KEY: misc_feature
<222> LOCATION: (79)..(79)
<223> OTHER INFORMATION: n is a, c, g, or t

<400> SEQUENCE: 41

atgaagacgc tgagcggcgg cggcggcggc gcggagcagg gccaggctct gttcaacggg      60
```

```
gacatggaac ccggaggcnc cgcgccggcg cccgcggcct cgtcggccgc ggaccctgcc    120
attcccgagg aggtatggaa tatcaaacaa atgattaaat tgacacagga acatatagag    180
gccctattgg acaaatttgg tggggagcat aatccaccat caatatatct ggaggcctat    240
gaagaataca ccagcaagct agatgccctc caacaaagag aacaacagtt attggaatcc    300
ctggggaatg gaactgattt ttctgtttct agttctgcat caacggacac cgttacatct    360
tcttcctctt ctagcctttc agtgctacct tcatctcttt cagtttttca aaatcccaca    420
gatgtgtcac ggagcaaccc taagtcacca caaaaaccta tcgttagagt cttcctgccc    480
aacaaacaga ggacagtggt acctgcaagg tgtggcgtta cagtccggga cagtctaaag    540
aaagcactga tgatgagagg tctaatccca gagtgctgtg ctgtttacag aattcaggat    600
ggagagaaga aaccaattgg ctgggacact gatatttcct ggctcactgg agaggaattg    660
catgtagaag tgttggagaa tgttccactt acaacacaca actttgtacg gaaaactttt    720
ttcaccttag cattttgtga cttttgtcga aagctgcttt tccagggttt ccgctgtcaa    780
acatgtggtt ataaatttca ccagcgttgt agtacagagg ttccactgat gtgtgttaat    840
tatgaccaac ttgatttgct gtttgtctcc aagttctttg aacaccaccc agtatcacag    900
gaggaggcct ccttagcaga gactgccctt acatctggat catccccttc tgcacccccc    960
tccgattcca ttgggcccca aattctcacc agtccatctc cttcaaaatc cattccaatt   1020
ccacagcctt tccgaccagc agatgaagat catcgaaatc agtttggaca acgagaccgg   1080
tcctcatcag ctccaaatgt acatataaac acaatagaac ctgtcaatat tgatgacttg   1140
attagagacc aagggtttcg tagtgatgga ggatcaacca caggtttatc tgccaccccc   1200
cctgcctcat tacctggctc actcactaat gtgaaggcat tacagaaatc tccaggacct   1260
caacgggaaa ggaaatcatc ttcatcctca gaagacagga atcgaatgaa aactcttggt   1320
agacgggatt caagtgacga ttgggagatt cctgatgggc agatcacagt gggacaaaga   1380
attggatctg ggtcatttgg gacagtctac aagggaaagt ggcatggtga tgtggcagtg   1440
aaaatgttga atgtgacagc acccacacct cagcagttac aggccttcaa aaatgaagta   1500
ggagtactca ggaaaactcg acatgtgaat atcctactct tcatgggcta ttcaacaaag   1560
ccacaactgg ctattgttac ccagtggtgt gagggctcca gcttatatca ccatctccac   1620
atcattgaga ccaaatttga gatgatcaaa cttatagata ttgctcggca aactgcacag   1680
ggcatggatt acttacacgc caagtcaatc atccacagag acctcaagag taataatatt   1740
tttcttcatg aagacctcac agtaaaaata ggtgattttg gtctagccac agtgaaatct   1800
cgatggagtg ggtcccatca gtttgaacag ttgtctggat ccattttgtg gatggcacca   1860
gaagtaatca gaatgcaaga taaaaacccg tatagctttc aatcagatgt atatgccttt   1920
gggattgttc tgtatgaatt gatgactgga cagttacctt attcaaacat caacaacagg   1980
gaccagataa tttttatggt gggaagagga tatctatctc cagatctcag taaggtacgg   2040
agtaactgtc caaaagccat gaagagatta atggcagagt gcctaaaaaa gaaaagagac   2100
gagagaccac tcttccccca aattctcgcc tctattgagc tgctggcccg ctcattgcca   2160
aaaattcacc gcagtgcatc agagccctcc ttgaatcggg ctggcttcca gacagaggat   2220
tttagtctat atgcttgtgc ttctccgaaa acacccatcc aggcaggggg atatggtgcg   2280
tttcctgtcc actga                                                    2295
```

<210> SEQ ID NO 42

<211> LENGTH: 764
<212> TYPE: PRT
<213> ORGANISM: Equus caballus
<220> FEATURE:
<221> NAME/KEY: misc_feature
<222> LOCATION: (27)..(27)
<223> OTHER INFORMATION: Xaa can be any naturally occurring amino acid

<400> SEQUENCE: 42

```
Met Lys Thr Leu Ser Gly Gly Gly Gly Gly Ala Glu Gln Gly Gln Ala
1               5                   10                  15

Leu Phe Asn Gly Asp Met Glu Pro Gly Gly Xaa Ala Pro Ala Pro Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Ser Ser Leu Ser Val
        115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
        195                 200                 205

Asp Thr Asp Ile Ser Trp Leu Thr Gly Glu Glu Leu His Val Glu Val
    210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
            260                 265                 270

Glu Val Pro Leu Met Cys Val Asn Tyr Asp Gln Leu Asp Leu Leu Phe
        275                 280                 285

Val Ser Lys Phe Phe Glu His His Pro Val Ser Gln Glu Glu Ala Ser
    290                 295                 300

Leu Ala Glu Thr Ala Leu Thr Ser Gly Ser Ser Pro Ser Ala Pro Pro
305                 310                 315                 320

Ser Asp Ser Ile Gly Pro Gln Ile Leu Thr Ser Pro Ser Pro Ser Lys
                325                 330                 335

Ser Ile Pro Ile Pro Gln Pro Phe Arg Pro Ala Asp Glu Asp His Arg
            340                 345                 350

Asn Gln Phe Gly Gln Arg Asp Arg Ser Ser Ser Ala Pro Asn Val His
        355                 360                 365
```

-continued

```
Ile Asn Thr Ile Glu Pro Val Asn Ile Asp Asp Leu Ile Arg Asp Gln
    370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Thr Asn Val Lys Ala Leu Gln Lys
                405                 410                 415

Ser Pro Gly Pro Gln Arg Glu Arg Lys Ser Ser Ser Ser Ser Glu Asp
            420                 425                 430

Arg Asn Arg Met Lys Thr Leu Gly Arg Arg Asp Ser Ser Asp Asp Trp
        435                 440                 445

Glu Ile Pro Asp Gly Gln Ile Thr Val Gly Gln Arg Ile Gly Ser Gly
    450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
            500                 505                 510

Leu Phe Met Gly Tyr Ser Thr Lys Pro Gln Leu Ala Ile Val Thr Gln
        515                 520                 525

Trp Cys Glu Gly Ser Ser Leu Tyr His His Leu His Ile Ile Glu Thr
    530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
            580                 585                 590

Phe Gly Leu Ala Thr Val Lys Ser Arg Trp Ser Gly Ser His Gln Phe
        595                 600                 605

Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Ala Phe Pro Val His
        755                 760
```

<210> SEQ ID NO 43
<211> LENGTH: 2678
<212> TYPE: DNA

<213> ORGANISM: Gallus gallus

<400> SEQUENCE: 43

```
tcccctccc tcgccccagc gcttcgatcc aagatggcgg cgctgagcag cggcagcagc      60
gccgaggggg cctcgctctt caacggggac atggagcccg agccgccgcc gcccgtgctg     120
ggcgcctgct acgccgggag cggcggcggc gacccggcca tcccggagga ggtgtggaat     180
atcaaacaga tgattaaatt aacacaagaa catatagaag cgctgttaga caagtttgga     240
ggagagcata acccaccatc aatatattta gaggcctatg aggagtacac cagcaaacta     300
gatgctctac agcagagaga acagcagtta ttggaatcca tgggaaatgg aactgatttc     360
tctgtttcca gttcagcttc aacggacaca gttgcatcat cttcctcctc tagcctctct     420
gtagcacctt catccctttc agtttatcaa aatcctactg atatgtcgcg gaataaccct     480
aagtctccac agaagcctat tgttagagtc ttcctgccca acaagcaaag gactgtggtt     540
ccggcaagat gtggggtgac agtccgagac agcctgaaga aagctctgat gatgagaggt     600
cttattccag aatgctgtgc tgtttacaga atacaggatg gagagaagaa gccaattggc     660
tgggacactg acatttcctg gctaaccgga gaggagttac acgtggaggt cttggagaat     720
gtgccactca caacacacaa ttttgtacga aaaacattct tcacgttagc gttctgcgac     780
ttctgtcgaa agctgctttt ccagggattc cgatgccaga catgtggcta caaatttcac     840
cagcgctgta gcacagaagt gccactgatg tgtgttaact acgaccaact cgatttgctg     900
tttgtctcca agttctttga acatcacccc atatcgcagg aggagaccac cttaggagag     960
accaccccgg catcgggatc gtacccctca gtgcccccat cagattctgt tggaccacca    1020
attctcccta gtccttctcc ttcaaaatcc attccaatcc cacagccctt ccgaccagca    1080
gatgaagacc atcggaatca gtttgggcaa cgcgaccgat cctcttcagc tcccaatgtt    1140
cacatcaata caattgagcc agtcaatatt gatgacttga ttagagacca gggtgtacga    1200
ggagagggag ccccttttgaa ccagctgatg cgctgtcttc ggaaatacca atcccggact    1260
cccagtcccc tccttcattc tgtccccagt gaaatagtgt ttgattttga gcctggccca    1320
gtgttcagag gttcaactgc aggtttgtct gcaacacctc ctgcatcttt gcctgggtca    1380
cttaccaatg tgaaagcatt acagaaatca ccaggccccc aacgggaaag gaaatcatcc    1440
tcatcctcag aagacagaaa taggatgaaa acccttggtc gacgagattc aagtgatgat    1500
tgggaaatac cagatgggca gatcacagtt ggacaaagga taggatctgg atcatttgga    1560
acagtctaca aaggaaagtg gcatggtgac gtggcagtga aaatgttgaa tgttacagca    1620
cccacacctc aacagttaca ggctttcaaa aatgaagtag gagtgctcag gaaaacacgg    1680
catgtgaata tcctactttt tatgggttat tcaacaaaac ctcagttggc tattgttaca    1740
cagtggtgtg aggggtccag cttatatcac catctgcaca taattgagac caagtttgaa    1800
atgatcaaac taattgatat tgcacgacag actgcacaag gcatggatta tttgcatgcc    1860
aagtcaatca tccacagaga cctcaagagt aataatattt ttcttcatga agacctcaca    1920
gtaaaaatag gtgacttcgg tctggctaca gtgaaatcac gatggagtgg atctcatcaa    1980
tttgaacagt tatctggatc aattctatgg atggcaccgg aagtgatcag gatgcaagac    2040
aaaaacccat atagctttca gtcagatgtg tatgcattcg ggattgtgct ttatgaactg    2100
atgactggac agttaccata ctcaaacatc aacaacaggg accagataat ttttatggtg    2160
ggacgaggat atctatctcc agacctcagt aaagtaagaa gtaactgtcc aaaagctatg    2220
aagagactaa tggcagaatg cttgaaaaag aaaagagatg agagacctct tttccacag     2280
```

```
attcttgcct ccattgagct tctggcccgg tcgttgccaa aaattcaccg cagtgcatct   2340

gagccgtcac taaaccgggc tggcttccag accgaggatt tcagtctgta tgcttgtgct   2400

tctccaaaaa cgcccatcca agcaggggga tacggtgggt ttccagtaca ctgaaaagaa   2460

atgtgaaagc gtgtgcctgt ttgctcatgt gctggtgtgt tcctgtgtgt gcaacgcata   2520

cgtacgttct cagttcctac cagcgacttt ttaaggttta ctgagggaat gaagactcat   2580

ttcctaacat ggggcattga acgtcctgag cacaagtcag tgctggtaag gaatgtcttg   2640

ggaacagctg gcaagaagaa ttagaaggta cttaaagg                           2678


<210> SEQ ID NO 44
<211> LENGTH: 806
<212> TYPE: PRT
<213> ORGANISM: Gallus gallus

<400> SEQUENCE: 44

Met Ala Ala Leu Ser Ser Gly Ser Ser Ala Glu Gly Ala Ser Leu Phe
1               5                   10                  15

Asn Gly Asp Met Glu Pro Glu Pro Pro Pro Val Leu Gly Ala Cys
            20                  25                  30

Tyr Ala Gly Ser Gly Gly Gly Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Met Gly Asn Gly Thr Asp Phe Ser Val Ser
            100                 105                 110

Ser Ser Ala Ser Thr Asp Thr Val Ala Ser Ser Ser Ser Ser Ser Leu
        115                 120                 125

Ser Val Ala Pro Ser Ser Leu Ser Val Tyr Gln Asn Pro Thr Asp Met
    130                 135                 140

Ser Arg Asn Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Ser Gln Glu Glu
    290                 295                 300
```

```
Thr Thr Leu Gly Glu Thr Thr Pro Ala Ser Gly Ser Tyr Pro Ser Val
305                 310                 315                 320

Pro Pro Ser Asp Ser Val Gly Pro Pro Ile Leu Pro Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Val Arg Gly Glu Gly Ala Pro Leu Asn Gln Leu Met Arg
385                 390                 395                 400

Cys Leu Arg Lys Tyr Gln Ser Arg Thr Pro Ser Pro Leu Leu His Ser
                405                 410                 415

Val Pro Ser Glu Ile Val Phe Asp Phe Glu Pro Gly Pro Val Phe Arg
            420                 425                 430

Gly Ser Thr Ala Gly Leu Ser Ala Thr Pro Pro Ala Ser Leu Pro Gly
        435                 440                 445

Ser Leu Thr Asn Val Lys Ala Leu Gln Lys Ser Pro Gly Pro Gln Arg
    450                 455                 460

Glu Arg Lys Ser Ser Ser Ser Ser Glu Asp Arg Asn Arg Met Lys Thr
465                 470                 475                 480

Leu Gly Arg Arg Asp Ser Ser Asp Asp Trp Glu Ile Pro Asp Gly Gln
                485                 490                 495

Ile Thr Val Gly Gln Arg Ile Gly Ser Gly Ser Phe Gly Thr Val Tyr
            500                 505                 510

Lys Gly Lys Trp His Gly Asp Val Ala Val Lys Met Leu Asn Val Thr
        515                 520                 525

Ala Pro Thr Pro Gln Gln Leu Gln Ala Phe Lys Asn Glu Val Gly Val
    530                 535                 540

Leu Arg Lys Thr Arg His Val Asn Ile Leu Leu Phe Met Gly Tyr Ser
545                 550                 555                 560

Thr Lys Pro Gln Leu Ala Ile Val Thr Gln Trp Cys Glu Gly Ser Ser
                565                 570                 575

Leu Tyr His His Leu His Ile Ile Glu Thr Lys Phe Glu Met Ile Lys
            580                 585                 590

Leu Ile Asp Ile Ala Arg Gln Thr Ala Gln Gly Met Asp Tyr Leu His
        595                 600                 605

Ala Lys Ser Ile Ile His Arg Asp Leu Lys Ser Asn Asn Ile Phe Leu
    610                 615                 620

His Glu Asp Leu Thr Val Lys Ile Gly Asp Phe Gly Leu Ala Thr Val
625                 630                 635                 640

Lys Ser Arg Trp Ser Gly Ser His Gln Phe Glu Gln Leu Ser Gly Ser
                645                 650                 655

Ile Leu Trp Met Ala Pro Glu Val Ile Arg Met Gln Asp Lys Asn Pro
            660                 665                 670

Tyr Ser Phe Gln Ser Asp Val Tyr Ala Phe Gly Ile Val Leu Tyr Glu
        675                 680                 685

Leu Met Thr Gly Gln Leu Pro Tyr Ser Asn Ile Asn Asn Arg Asp Gln
    690                 695                 700

Ile Ile Phe Met Val Gly Arg Gly Tyr Leu Ser Pro Asp Leu Ser Lys
705                 710                 715                 720
```

-continued

```
Val Arg Ser Asn Cys Pro Lys Ala Met Lys Arg Leu Met Ala Glu Cys
                725                 730                 735

Leu Lys Lys Lys Arg Asp Glu Arg Pro Leu Phe Pro Gln Ile Leu Ala
            740                 745                 750

Ser Ile Glu Leu Leu Ala Arg Ser Leu Pro Lys Ile His Arg Ser Ala
        755                 760                 765

Ser Glu Pro Ser Leu Asn Arg Ala Gly Phe Gln Thr Glu Asp Phe Ser
    770                 775                 780

Leu Tyr Ala Cys Ala Ser Pro Lys Thr Pro Ile Gln Ala Gly Gly Tyr
785                 790                 795                 800

Gly Gly Phe Pro Val His
                805
```